United States Patent
Mills

(10) Patent No.: US 7,689,367 B2
(45) Date of Patent: Mar. 30, 2010

(54) METHOD AND SYSTEM OF COMPUTING AND RENDERING THE NATURE OF THE EXCITED ELECTRONIC STATES OF ATOMS AND ATOMIC IONS

(75) Inventor: Randell L. Mills, Princeton, NJ (US)

(73) Assignee: Blacklight Power, Inc., Cranbury, NJ (US)

( * ) Notice: Subject to any disclaimer, the term of this patent is extended or adjusted under 35 U.S.C. 154(b) by 240 days.

(21) Appl. No.: 11/596,218

(22) PCT Filed: May 17, 2005

(86) PCT No.: PCT/US2005/017216

§ 371 (c)(1),
(2), (4) Date: Nov. 14, 2006

(87) PCT Pub. No.: WO2005/116630

PCT Pub. Date: Dec. 8, 2005

(65) Prior Publication Data

US 2008/0034287 A1    Feb. 7, 2008

(51) Int. Cl.
*G01N 31/00* (2006.01)

(52) U.S. Cl. .............................. 702/22; 702/19; 702/23; 372/19; 372/69; 436/173

(58) Field of Classification Search ................... 702/19, 702/22, 23; 372/19, 69; 436/173
See application file for complete search history.

(56) References Cited

U.S. PATENT DOCUMENTS

| | | | |
|---|---|---|---|
| 1,001,589 | A | 8/1911 | Hatfield |
| 2,708,656 | A | 5/1955 | Fermi |
| 3,253,884 | A | 5/1966 | Jung et al. |
| 3,297,484 | A | 1/1967 | Niedrach |

(Continued)

FOREIGN PATENT DOCUMENTS

EP        0 392 325 A3    10/1990

(Continued)

OTHER PUBLICATIONS

Abdallah, et. al. "The Behavior of Nitrogen Excited in an Inductively Coupled Argon Plasma." *J. Appl. Phys.*, vol. 88, No. 1, Jul. 2000, pp. 20-33.

(Continued)

*Primary Examiner*—Carol S Tsai
(74) *Attorney, Agent, or Firm*—Finnegan, Henderson, Farabow, Garrett & Dunner L.L.P.

(57) ABSTRACT

A method and system of physically solving the charge, mass, and current density functions of excited-state atoms and atomic ions using Maxwell's equations and computing and rendering the nature of excited-state electrons using the solutions. The results can be displayed on visual or graphical media. The display can be static or dynamic such that electron spin and rotation motion can be displayed in an embodiment. The displayed information is useful to anticipate reactivity and physical properties. The insight into the nature of excited-state electrons can permit the solution and display of those of other atoms and atomic ions and provide utility to anticipate their reactivity and physical properties as well as spectral absorption and emission to lead to new optical materials and light sources.

97 Claims, 7 Drawing Sheets

U.S. PATENT DOCUMENTS

| | | | |
|---|---|---|---|
| 3,300,345 A | 1/1967 | Lyons | |
| 3,359,422 A | 12/1967 | Pollock | |
| 3,377,265 A | 4/1968 | Caeser | |
| 3,448,035 A | 6/1969 | Serfass | |
| 3,462,622 A | 8/1969 | Cann et al. | |
| 3,669,745 A | 6/1972 | Beccu | |
| 3,701,632 A | 10/1972 | Lovelock | |
| 3,755,128 A | 8/1973 | Herwig | |
| 3,816,192 A | 6/1974 | Brower | |
| 3,835,019 A | 9/1974 | Lovelock | |
| 3,917,520 A | 11/1975 | Katz | |
| 4,000,036 A * | 12/1976 | Ensley | 376/123 |
| 4,095,118 A | 6/1978 | Rathbun | |
| 4,149,931 A * | 4/1979 | Christensen | 376/134 |
| 4,155,712 A | 5/1979 | Taschek | |
| 4,202,004 A | 5/1980 | Andersen | |
| 4,265,720 A | 5/1981 | Winstel | |
| 4,274,938 A | 6/1981 | Schulten | |
| 4,327,071 A | 4/1982 | Chiu et al. | |
| 4,337,126 A | 6/1982 | Gilligan, III et al. | |
| 4,353,871 A | 10/1982 | Bartlit et al. | |
| 4,464,990 A | 8/1984 | Bendler | |
| 4,487,670 A | 12/1984 | Bellanger | |
| 4,488,490 A | 12/1984 | Betts | |
| 4,512,966 A | 4/1985 | Nelson | |
| 4,568,568 A | 2/1986 | Asano | |
| 4,664,904 A | 5/1987 | Wolfrum | |
| 4,694,755 A | 9/1987 | Ibarra | |
| 4,702,894 A | 10/1987 | Cornish | |
| 4,737,249 A | 4/1988 | Shepard, Jr. | |
| 4,774,065 A | 9/1988 | Penzhorn | |
| 4,792,725 A * | 12/1988 | Levy et al. | 315/39 |
| 4,808,286 A | 2/1989 | Angelo, II | |
| 4,905,118 A | 2/1990 | Sakich | |
| 4,923,770 A | 5/1990 | Grasselli | |
| 4,957,727 A | 9/1990 | Bogdanovic | |
| 4,968,395 A | 11/1990 | Pavelle | |
| 4,986,887 A | 1/1991 | Gupta | |
| 5,215,729 A | 6/1993 | Buxbaum | |
| 5,273,635 A | 12/1993 | Gernert | |
| 5,318,675 A | 6/1994 | Patterson | |
| 5,372,688 A | 12/1994 | Patterson | |
| 5,449,434 A * | 9/1995 | Hooke et al. | 216/70 |
| 5,577,090 A * | 11/1996 | Moses | 378/64 |
| 5,593,640 A | 1/1997 | Long et al. | |
| 5,669,975 A * | 9/1997 | Ashtiani | 118/723 I |
| 5,761,481 A * | 6/1998 | Kadoch et al. | 703/2 |
| 5,789,744 A | 8/1998 | Spence et al. | |
| 5,801,971 A * | 9/1998 | Ohta | 703/12 |
| 5,819,073 A | 10/1998 | Nakamura | 716/20 |
| 5,838,760 A * | 11/1998 | Moses | 378/119 |
| 5,864,322 A * | 1/1999 | Pollon et al. | 343/909 |
| 5,883,005 A * | 3/1999 | Minton et al. | 438/707 |
| 5,888,414 A * | 3/1999 | Collins et al. | 216/68 |
| 5,969,470 A * | 10/1999 | Druz et al. | 313/359.1 |
| 6,024,935 A * | 2/2000 | Mills et al. | 423/648.1 |
| 6,064,154 A * | 5/2000 | Crouch et al. | 315/39.57 |
| 6,149,829 A | 11/2000 | Takamatsu et al. | |
| 6,150,755 A * | 11/2000 | Druz et al. | 313/359.1 |
| 6,151,532 A * | 11/2000 | Barone et al. | 700/121 |
| 6,444,137 B1 * | 9/2002 | Collins et al. | 216/79 |
| 6,551,939 B2 | 4/2003 | Takamatsu et al. | |
| 6,579,465 B1 | 6/2003 | Takamatsu et al. | |
| 6,690,705 B2 * | 2/2004 | Maksimov et al. | 372/69 |
| 7,188,033 B2 * | 3/2007 | Mills | 702/22 |
| 2001/0007725 A1 | 7/2001 | Faris et al. | |
| 2001/0008803 A1 | 7/2001 | Takamatsu et al. | |
| 2002/0133326 A1 * | 9/2002 | Chung et al. | 703/18 |

FOREIGN PATENT DOCUMENTS

| | | |
|---|---|---|
| EP | 0 395 066 A2 | 10/1990 |
| GB | 2 343 291 | 5/2000 |
| JP | 53-134792 | 11/1978 |
| JP | 56-136644 | 3/1980 |
| JP | 2002008892 A | 1/2002 |
| JP | 2002008892 A * | 1/2002 |
| WO | WO 90/10935 A1 | 9/1990 |
| WO | WO 90/13126 A1 | 11/1990 |
| WO | WO 90/14668 A2 | 11/1990 |
| WO | WO 91/01036 A1 | 1/1991 |
| WO | WO 91/08573 A1 | 6/1991 |
| WO | WO 92/10838 A1 | 6/1992 |
| WO | WO 93/17437 A1 | 9/1993 |
| WO | WO 94/10688 A1 | 5/1994 |
| WO | WO 94/14163 A1 | 6/1994 |
| WO | WO 94/15342 A1 | 7/1994 |
| WO | WO 94/29873 A2 | 12/1994 |
| WO | WO 95/20816 A1 | 8/1995 |
| WO | WO 96/42085 A2 | 12/1996 |
| WO | WO 99/05735 A1 | 3/1999 |
| WO | WO 99/26078 A1 | 5/1999 |
| WO | WO 99/34322 A1 | 7/1999 |
| WO | WO 99/35698 A3 | 7/1999 |
| WO | WO 00/07931 A1 | 2/2000 |
| WO | WO 00/07932 A2 | 2/2000 |
| WO | WO 00/25320 A1 | 5/2000 |
| WO | WO 01/18948 A1 | 3/2001 |
| WO | WO 01/21300 A2 | 3/2001 |
| WO | WO 01/22472 A2 | 3/2001 |
| WO | WO 01/70627 A3 | 8/2001 |
| WO | WO 01/95944 A2 | 12/2001 |
| WO | WO 02/08787 A2 | 1/2002 |
| WO | WO 02/16956 A1 | 2/2002 |
| WO | WO 02/087291 A2 | 10/2002 |
| WO | WO 02/088020 A2 | 11/2002 |
| WO | WO 03/066516 A2 | 8/2003 |
| WO | WO 03/093173 A2 | 11/2003 |
| WO | WO 2004/092058 A2 | 10/2004 |
| WO | WO 2005/067678 A2 | 7/2005 |
| WO | WO 2005/041368 A2 | 10/2005 |
| WO | WO 2005/116630 A1 | 12/2005 |
| WO | WO 2007/051078 A1 | 5/2007 |
| WO | WO 2007/053486 A1 | 5/2007 |

OTHER PUBLICATIONS

Abelès, Ed. Chapter 9, "Structure of Trapped Electron and Trapped Hole Centers in Alkali Halides 'Color Centers'." *Optical Properties of Solids*, 1972, pp. 718-754.

Abramova, et. al. "Tornado-type closed magnetic trap for an electron cyclotron resonance ion source." *Review of Scientific Instruments*, vol. 71, No. 2, Feb. 2000, pp. 921-923.

Albagli, et. al. "Measurement and Analysis of Neutron and Gamma-Ray Emission Rates, Other Fusion Products, and Power in Electrochemical Cells Having Pd Cathodes." *Journal of Fusion Energy*, vol. 9, No. 2, Jun. 1990, pp. 133-148.

Alber, et. al. "Search for Neutrons from Cold Nuclear Fusion." *Z. Phys. A.—Atomic Nuclei*, vol. 333, 1989, pp. 319-320.

Alessandrello, et. al. "Search for Cold Fusion Induced by Electrolysis in Palladium." *Il Nuovo Cimento*, vol. 103A, No. 11, Nov. 1990, pp. 1617-1638.

Alger et al. "F Centers in Pure and Hydride-Containing Alkali Halide crystals." *Physical Review*, vol. 97, Jan. 15, 1955, pp. 277-287.

Arfken. "Mathematical Methods for Physicists." 2$^{nd}$ Ed. *Academic Press*, New York 1970, pp. 413-415.

S. Aaronson, "Hydrino Theory: Which Overturns Quantum Theory, Is in Turn Overturned by Doofusino Theory," <http://www.scottaaronson.com/writings/doofusino.html>.

Associated Press. "Panel Opposes Cold Fusion Efforts." *The Washington Post*, Jul. 13, 1989, p. A14.

Associated Press. "Pennsylvania Company . . . Cold Fusion Mystery." *Lexis Nexis* Reprint, 1991.
Associated Press. "Physicist: Utah Cold-Fusion Gear Doesn't Work." *The Washington Post*, Mar. 29, 1990, p. A3.
"Atomic Spectroscopy" (internet page) physics.nist.gov/Pubs/AtSpec/node20.html (author and date unknown).
Baard, Erik. "The Empire Strikes Back." *The Village Voice*, Apr. 26-May 2, 2000.
Baard, Erik. "Quantum Leap." *The Village Voice*, Dec. 22-28, 1999.
Baard, Erik. "Researcher Claims Power Tech That Defies Quantum Theory." *Dow Jones Newswires*, Oct. 6, 1999.
Baard, Erik, "Hydrino Theorist Gets Nod From NASA-Funded Investigation Eureka?", *The Village Voice*, Dec. 6, 2002.
Balke, et. al. "Limits on Neutron Emission From 'Cold Fusion' in Metal Hydrides.", *Physical Review C*, vol. 42, No. 1, Jul. 1990, pp. 30-37.
Barmann et. al. "Spatially and Temporally Resolved Studies of the Electron Density in Liquid Streamers by Emission Spectroscopy" (Internet page) atompc2.fysiclth.se/AFDOCS/Progrep956/5al.htm (Atomic Physics Progress Report) (1995-1996).
Barth, "Bigger Than Fire?", Gale Group Magazine DB, The Gale Group, 2003, Skeptic, vol. 8, No. 4, (2001).
Barton, et al, "Investigating Radio Frequency Plasmas Used for the modification of Polymer Surfaces." *J. Phys. Chem. B*, vol. 103, 1999, pp. 4423-4430.
R. W. Bass, "Email from Bob Bass to Randell Mills," Aug. 6, 2000.
Bäuerle et al. "Infared Vinrational Absorption by U-Centers in NaI." *Phys. Stat. Sol.*, vol. 24, 1967, pp. 207-215.
Beiser, A. *Concepts of Modern Physics*, Fourth Edition, McGraw-Hill Book Company, New York, 1978, p. 407.
Benetskii, et. al. "An Attempt to Observe Cold Thermonuclear Fusion in a Condensed Medium." *Nuclear Research Institute*, AS USSR, May 1989, pp. 75-78.
Besenbacher, et. al. "Search for Cold Fusion in Plasma-Charged Pd-D and Ti-D Systems." *Journal of Fusion Energy*, vol. 9, No. 3, Sep. 1990, pp. 315-317.
Best, Ben. "The Copenhagen Interpretation of Quantum Mechanics." (internet page) www.benbest.com/science/quantum.html. (no date listed).
Bethe, et. al. "Quantum Mechanics of One and Two-Electron Atoms." *Cornell University*, Plenum Publishing Com., NY, 1977, pp. 2, 9-12, 47, 83-84, 92, 107.
"The Biggest Venture Capital Conference of the Year is Quickly Approaching," Special to Evening Bullitin Sep. 29, 2006, <http://www.theeveningbulletin.com/site/news.cfm?newsid=17263371&BRD=2737&PAG=461&dept_id=57636&rfi=6.
Bishop. "It ain't over til it's over . . . Cold Fusion." *Popular Science*, Aug. 1993, pp. 47-51.
Bishop. "More Labs Report Cold Fusion Results." *Wall Street Journal*, Oct. 19, 1992.
Bjorken et al., "Relativistische Quantenmechanik", *Die Dirac-Gleichung*, pp. 22-25, 1964.
"Blacklight Power—do they have something significant?" (internet page) www.phact.org/e/b1p.htm (author and date unknown).
BlackLight Power, "Executive Summary," Jan. 11, 1999, pp. 1-6.
Backlight Power, Inc., "Second Shareholder Newsletter '97" <http://web.archive.org/web/19980212141859/blacklightpower.com/sharenews2.html>.
Blochinzew, Grundlagen Der Quantenmechanik, Veb Deutscher Verlag Der Wissenschaften, 1967.
Blue. "Cold Fusion Lies 6." *Deja News on the Internet*, Apr. 13, 1997, pp. 1-2, available at http://x7.dejanew/us.com.
Blue. "Randell Mills' Sells Pot Shards." *Deja News on the Internet*, Apr. 30, 1997, pp. 1-2, available at http://x7.dejanew/us.com.
Bogaerts, et al. "Effects of adding hydrogen to an argon glow discharge: overview of relevant processes and some qualitative explanations." *Journal of Analytical Atomic Spectrometry*, Mar. 2000.
Boniface, et al. "Calorimetry for a Ni/$K_2CO_3$ Cell." AECL Research, Jun. 1994.
Bosch, et. al. "Electrochemical Cold Fusion Trials at IPP Garching." *Journal of Fusion Energy*, vol. 9, No. 2, Jun. 1990, pp. 165-186.
Boston Globe., "Successful nuclear fusion experiment by the Italians." Wednesday, Apr. 19, 1989.

Braaten. "Ridiculously Easy Test Yields Claim of Energy Triumph." *The Washington Times*, Mar. 24, 1989, p. A5.
Bradford. "A Calorimetric Investigation of the Reaction of Hydrogen with Sample PSU #1." A Confidential Report submitted to Hydrocatalysis Power Corporation, Sep. 1994.
Briars. "Critique of New Energy, New Physics." 7 segments, *Deja News on the Internet*, Mar. 9, 1989, pp. 1-9, available at http://x7.dejanew/us.com.
Brewer, Shelby T. Book review of "The grand Unified Theory of Classical Quantum Mechanics (Hardcover) by Randell L., Dr. Mills." (internet page) http://www.amazon.com/gp/product/product-description/0963517139/ref=dp_proddesc_0/103-5711659-8507030 (date unknown).
Broad. "2 Teams Put New Life in Cold Fusion Theory." *New York Times*, Apr. 26, 1991, p. A18.
Broad. "Cold-Fusion Claim is Faulted on Ethics as Well as Science." *The New York Times*, Mar. 17, 1991, pp. 1 and 30.
Brodowsky, "Solubility and diffusion of hydrogen an deuterium in Palladium and Palladium Alloys," Tech. Bulletin, England Indust., vol. 7, No. 1-2 (1966), pp. 41-50.
Browne. "Fusion Claims is Greeted With Scorn by Physicists." *The New York Times*, May 3, 1989, pp. A1 and A22.
Browne. "Physicists Put Atom in 2 Places at Once." *The New York Times*.
Bush. "A Light Water Excess Heat Reaction Suggests That 'Cold Fusion' May Be 'Alkali-Hydrogen Fusion'." *Fusion Technology*, vol. 22, Sep. 1992, pp. 301-322.
Bush, et. al. "Helium Production During the Electrolysis . . . Experiments." *J. Electroanal Chem.*, vol. 304, 1991, pp. 271-278.
Bush, et. al. "Helium Production During the Electrolysis . . . Experiments." *Preliminary Note, Univ. of Texas*, pp. 1-12.
Bush, et. al. "Power in a Jar: the Debate Heats Up." 88 Bus. Week, *Science & Technology*, Oct. 26, 1992.
Carolina, et al. "Effect of Dielectric Constant, Cavities in Series and Cavities in Parallel on the Product Distribution of the Oligomerization of Methane via Microwave Plasmas." *J. Phys. Chem.*, vol. 100, 1996, pp. 17866-17872.
Catlett, et. al. "Hydrogen transport in lithium hydride as a function of pressure." *The Journal of Chemical Physics*, vol. 58, No. 8, Apr. 1978, pp. 3432-3438 (Apr. 1978).
Chapline. "Cold Confusion." *UCRL-101583*, Jul. 1989, pp. 1-9.
Chemistry Course Listings in MIT OpenCourseWare. MIT 2005. http://ocw.mit.edu/Ocw/Web/Chemistry/index.htm.
"The Chemistry of Halogens," http://chemed.chem.purdue.edu/genchem/topicreview/bp/ch10/group7.html.
Chien, et. al. "On an Electrode . . . Tritium and Helium." *J. Electroanal Chem.*, 1992, pp. 189-212.
CiteSeer, "Citations: Observation of Extreme Ultraviolet Hydrogen Emission from Incandescently Heated Hydrogen Gas with Strontium that Produced an Anomalous Optically Measured Power Balance," Int. J. Hydrogen Energy 26 (4) 2001, p. 309-326 <http://citeseer.ist.psu.edu/comntext/1749692/449101>.
Clark, et. al. "Excess Energy Cell Final Report." Apr. 1995.
Close. "Too Hot to Handle-The Race for Cold Fusion." *Princeton University Press*, 1989.
Collins, "Selling the Free Lunch," Scientific American, (Nov. 2002).
Condon, et. al. "The Theory of Atomic Spectra." MacMillan Company: New York. 1935. pp. 44-78, 112-146.
Conrads, et. al. "Emission in the Deep Vacuum Ultraviolet from an Incandescently Driven Plasma in a Potassium Carbonate Cell", *Plasma Sources Science and Technology*, submitted.
Conversion Table cgs/Si-Units. www.plasmaphysics.org.uk/convers.htm.
Cooke. "ORNL/FTR-3341." Jul. 31, 1989, pp. 2-15.
Cribier, et. al. "Conventional Sources of Fast Neutrons in Cold Fusion Experiments." *Physics Letters B*, vol. 228, No. 1, Sep. 7, 1989, pp. 163-166.
Criddle. "The Roles of Solution . . . Excess Heating." *Electrochemical Science & Technology Centre*, Univ. of Ottawa.
Cvetanovic et. al. "Excessive Balmer line broadening in a plane cathode abnormal glow discharge in hydrogen." *Journal of Applied Physics* 97. Jan. 18, 2005.

Datz, et al. "Molecular Association in Alkali Halide Vapors." Journal of Chemical Physics, vol. 34, No. 5, Feb. 1961, pp. 558-564.

Dagani. "Cold Fusion believer turns skeptic crusades for more rigorous research." C&EN Washington, Jun. 5, 1995, pp. 34-45.

Dagani "Cold Fusion-Utah Pressures Pons, Fleischmann." C&EN, Jan. 14, 1991, pp. 4-5.

Dagani. "Latest Cold Fusion Results Fail to Win Over Skeptics." C&EN, Jun. 14, 1993, pp. 38-40.

Dagani. "New Evidence Claimed for Nuclear Process in 'Cold Fusion'." C&EN Washington, Apr. 1991, pp. 31-33.

Delbecq et al. "Pragmatic Resonance Investigation of Irradiated KCI Crystals Containing U-Centers." Phys. Rev., vol. 104, Nov. 1, 1956, pp. 599-604.

Dennis "Hidden Variables and Relativistic Tachyons" (Internet page) www.objectivescience.com/articles/ed_tachy.htm (Date unknown).

Dery et. al. "Effect of Dielectric constant, Cavities in Series, and Cavities in Parallel on the Product Description of the Oligomerization of Methane via Microwave Plasmas." Journal of Physical Chemistry 1996, vol. 100. Jul. 8, 1996. pp. 17866-17872.

Directory: Blacklight Power, From PESWiki "A Top 100 Energy Technology," <http://peswiki.com/index.php/Directory:Blacklight_Power>.

Dötsch et al. "Localized Vibrations of H$^-$ and D$^-$ Ions in NaF and LiF." Solid States Communications, vol. 3, 1965, pp. 297-298.

Dufour, et. al. "Interaction of Palladium/Hydrogen and Palladium/Deuterium to Measure the Excess Energy Per Atom for Each Isotope." Fusion Technology, vol. 31, Mar. 1997, pp. 198-209.

Durr, et. al. "Origin of quantum-mechanical complementarity probed by a 'which-way' experiment in an atom interferometer." Nature, vol. 395, Sep. 3, 1998, pp. 33-37.

"Earth Tech's Campaign to Replicate one of BlackLight Power Excess Heat Results." Dec. 20, 1997 available at www.eden.com/~little/blp/prelim.html, pp. 1-41.

EarthTech Reports, http://www.earthtech.org/experiments/b1p/prelim.html.

EarthTech Reports, http://www.earthtech.org/experiments/mills/mills1.html "Attempt to Observe Excess Heat in a Ni-H$^2$O-K$^2$CO$^3$ Electrolysis System-9OCT97".

Evans, et. al. "Time-of-Flight Secondary Ion Mass Spectroscopy (TOF-SIMS) Surface Analysis Report," CE & A Number 40150, Mar. 1994, available at http://www.cea.com/inst.htm#esca2.

Evans Analytical Group, http://www.cca.com/tech.htm#esca1.

Evans, et. al. "XPS/ESCA Results." CE & A No. 44545, Nov. 1994.

Evans Analytical Group. Product Descriptions: Time-of-Flight Secondary Mass Spectrometry (TOF-SIMS) and X-Ray Photoelectron Spectroscopy (XPS) Electron Spectroscopy for Chemical Anaylsis (ESCA). (no date or author listed).

Dr. Ess, "History and Philosophy of Science," www.drury.edu/ess/philsci/bell.html.

E-mail to Examiner Wayner from Jeffrey A. Simenauer, dated.

Ewing, et. al. "A sensitive multi-detector neutron counter used to monitor cold fusion experiments in an underground laboratory; negative results and positive artifacts." IEE Transactions on Nuclear Science, vol. 37, No. 3, Jun. 1990, pp. 1165-1170.

"Experimental Verification by Idaho National Engineering Laboratory." pp. 13-25.

Faller, et. al. "Investigation of Cold Fusion in Heavy Water." J. Radioanal. Nucl. Chem. Letter, vol. 137, No. 1, Aug. 21, 1989, pp. 9-16.

Fan et al., "X-ray photoelectron spectroscopy studies of CVD diamond films", Surface and Interface Analysis, 34:703-707, 2002.

Feynman, et al. "The Feynman Lectures of Physics vol. III: Quantum Mechanics." Adison-Wesley Publishing Co., 1965 pp. 1-9, 206, 19-1 through 19-18.

Fine, Arthur. "The Shaky Game: Einstein Realism and the Quantum Theory." 2$^{nd}$ Ed. The University of Chicago Press, 1986, pp. 64-85.

Fischer. "Die optische Absorption der U$_2$-Zentren in Alkalihalogenidkristallen", Zeitschrift für Physik, vol. 131, 1952, pp. 488-504.

Fischer et al. "Sh$^-$ S$^-$ Und S$^-$ Zentren in KC1-Kristallen." Physics Letters, vol. 13, Oct. 27, 1964, pp. 113-114.

Fischer. "Die optische Absorption der U$_2$-Zentren in Alkalihalogeniden des BaCI-Typs," Zeitschrift für Physik, vol. 204, 1967, pp. 351-374.

Fitzpatrick, "The Linear Stark Effect," University of Texas Leture, http://farside.ph.utexas.edu/teachinp/om/pertubation/node8.html.

J. Flemming, et. al. "Calorimetric Studies of Electrochemical Incorporation of Hydrogen Isotopes into Palladium," J. of Fusion Energy, vol. 9, No. 4 (Dec. 1990), pp. 517-524.

Fozza, et. al. "Vacuum ultraviolet to visible emission from hydrogen plasma: Effect of excitation frequency." Journal of Applied Physics, vol. 88, No. 1, Jul. 2000, pp. 20-33.

Fried et al. "Solution for the Two-Electron Correlation Function in a Plasma." The Physical Review, vol. 122, Apr. 1, 1961, pp. 1-8.

Fritz. " Anionlücken und Zwischengitterionen in Alkalihalogenid-Alkalihydrid-Mischkristallen." J. Phys. Chem. Solids, vol. 23, 1962, pp. 375-394.

Fritz, "Infrared Absorption and Anharmonicity of the U-Centre Local Mode," Phys. Stat. Sol., vol. 11, (1965) pp. 231-239.

M. Fowler, "The Lorentz Transformation," UVa Physics 252, <http://galileo.phys.virginia.edu/classes/252/lorentztrans.html>.

Fuchs and Peres. "Quantum Theory Needs No 'Interpretation'." Physics Today, Mar. 2000, p. 70.

Fujimoto, et. al."Ratio of Balmer line intensities resulting from dissociative excitation of molecular hydrogen in an ionizing plasma." J. Appl. Phys., vol. 66, No. 6, Sep. 1989, pp. 2315-2319.

Fusion Digest, "Cold Nuclear Fusion Bibliography," 1993.

Fusion Digest, "Heat? Neutrons? Charged Particles?," 1993.

Gernert, et. al. "Anomalous Heat From Atomic Hydrogen in Contact with Potassium Carbonate." Thermacore, Inc.

Gottfried, "Quantum electrodynamics: Matter all in the mind", (internet page) www.nature.com/cgi-taf/DynaPage.t...e/journal/v419/n6903/full/419117a_r.html, 2002.

Gulyaev "Gigantic Atoms in Space" (internet page) www.astronomy.org.nz/events/month...reviews/2001/gigantic_atoms_in_space.htm (date unknown).

Hadfield. "Lukewarm reception for Japanese cold fusion." New Scientist, Oct. 31, 1992, p. 10.

Hajdas, et. al. "Search for Cold-Fusion Events." Solid State Communications, vol. 72, No. 4, 1989, pp. 309-313.

Hansen, et. al. "A response to hydrogen +oxygen recombination and related heat generation in undivided electrolysis cells." J. of Electroanalytical Chemistry, vol. 447, 1998, pp. 225-226. (Paper III).

Hansen, et. al. "Faradaic efficiencies less than 100% during electrolysis of water can account for excess heat in 'cold fusion' cells," J. of Physical Chem., vol. 99, No. 18 (1997) pp. 6973-6979 (Paper I).

Hansen, et. al. "An assessment of claims to 'excess heat' in 'cold fusion' calorimetry," Thermochimica Acta, vol. 297 (1998) pp. 7-15 (Paper II).

Hardy, et. al. "The Volatility of Nitrates and Nitrites of the Alkali Metals." Journal of the Chemical Society, 1963, pp. 5130-5134.

The Harvard Crimson News: Academics Question the Science Behind Blacklight Power, Inc. <http://www.the_crimson.com/printerfriendly.aspx?ref=100939>.

Haus. "On the radiation from point charges." American Journal of Physics, vol. 54, No. 12, Dec. 1986. pp. 1126-1129.

Hayashi, Shigenobu. "Accurate determination of $^1$H Knight shifts in Mg$_2$NiFl$_x$ and MgH$_x$ by means of high-speed magic angle spinning." Journal of Alloys and Compounds, vol. 248, 1997, pp. 66-69 (Paper A).

Hayashi, et. al. "$^1$H NMR and magnetization measurements of a nanostructured composite material of the Mg$_2$Ni-H system synthesized by reactive mechanical grinding." Journal of Alloys and Compounds, vol. 256, 1997, pp. 159-165. (Paper B).

Hayashi, et. al. "Local structures and hydrogen dynamics in amorphous and nanostructured Mg-Ni-H systems as studied by $^1$H and $^2$H nuclear magnetic resonance," J. of Alloys and Compounds, vol. 261, (1997), pp. 145-149 (Paper C).

He-II in Solar Spectrum.

Heisenberg, W. "Über den anschaulichen Inhalt der quantentheoretischen Kinematik und Mechanik." Zeitschrift für Physik, vol. 43, 1927, pp. 172-198.

Heitler, W. "The Quantum Theory of Radiation." 3$^{rd}$ Ed., University of Zürich, Dover Publications Inc., NY, 1984, pp. 104.

Henderson, et. at. "More Searches for Cold Fusion." *Journal of Fusion Energy*, vol. 9, No. 4, Dec. 1990, pp. 475-477.

Hilsch. "Eine neue Lichtabsorption in Alkalihalogenidkristalle." *Fachgruppe II*, pp. 322-328.

Hilsch. "Über die Diffusion und Reaktion von Wassestoff in KBr-Kristallen." *Annalen der Physik*, vol. 40, 1937, pp. 407-720.

Hilts. "Significant Errors Reported in Utah Fusion Experts." *The Washington Post*, May 2, 1989, pp. A1 and A7.

Hines, "Scientific Mistakes: N-rays and Polywater", *Pseudoscience and the Paranormal*, Prometheus Books, 1988, pp. 8-13.

Hodoroaba, et. al."Investigations of the effect of hydrogen in an argon glow discharge." *J. of Analytical Atomic Spectrometry*, www.rsc.org/ej/ja/2000/B0023671/ (1 of 14), Aug. 4, 2000.

Hollander, et. al. "Vacuum ultraviolet emission from microwave plasmas of hydrogen and its mixtures with helium and oxygen." *J. Vac. Sci. Technol.*, A12 (3), May/Jun. 1994, pp. 879-882.

Horanyi. "Some Basic Electrochemistry and the Cold Nuclear Fusion of Deuterium." *J. Radioanal. Nucl. Chem. Letters*, vol. 137, No. 1, Aug. 21, 1989, pp. 23-28.

http://omm.hut.fi/optics/1_o/2004/luennot/spectroscopy.pdf.

http:/hyperphisics.phy-ast.gsu.edu/hbase/kinetic/molke.htm.

Huizenga. "Abstract from 'New developments in the cold fusion saga'." *Abstracts of papers of the American Chemical Society*, vol. 207, Mar. 13, 1994, p. 6.

Huizenga. "Cold Fusion." *C & EN*, vol. 70, Jul. 20, 1992, p. 3.

Huizenga. "Cold Fusion Labeled Fiasco of the Century." *Forum for Applied Research and Public Policy*, vol. 7, No. 4, pp. 78-83.

Huizenga. "Cold Fusion-The Scientific Fiasco of the Century." *Oxford University Press*, 1993.

"Hydrino Theory," <http://en.wikipedia.org/wiki/hydrino_theory>.

"The Hydrogen Atom," <http://www.physics.nmt.edu/~raymond/classes/ph13xbook/node208.html>.

Hydrogen News 1999 <http://www.ch2bc.org/bulletin/bulletin19991112.htm>.

INRS-Energie at Materiaux XPS facility, http://goliath.inrs-ener.uquebec.ca/tour/.

The Internet Encyclopedia of Philosophy, "Logical Positivism," http://iep.utm.edu/logpos.htm.

Jackson, John David. "Classical Electrodynamics." $2^{nd}$ Ed., *University of California*, Berkley, John Wiley and Sons, 1975, Ch. 14.

Jacox, et. al. "INEL XPS Report." Idaho National Engineering Laboratory, EG &G Idaho, Inc., Nov. 1993.

Jansson. "Hydrocatalysis:: A New Energy Paradigm for the $21^{st}$ Century." A Thesis, Master of Science in Engineering Degree in the Graduate Division of Rowan University, May 1997.

Jeffreys, et al. "Methods of Mathematical Physics." Cambridge, England, 1950, pp. 618.

Johansson, et. al. "A Model for the origin of the anomalous and very bright UV lines of FE II in gaseous condensations of the star η Carinae" *Astronomy & Astrophysics*. vol. 378 (2001) pp. 266-278.

Jones. "Current Issues in Cold Fusion . . . Particles." *Surface and Coatings Technology*, vol. 51, 1992, pp. 283-289.

Jones, et. al. "Examination of Claims of Miles . . . Experiments." *J. Phys. Chem.*, 1995, pp. 6966-6972.

Jones, et. al. "Faradaic Efficiencies . . . Cells." *J. Phys. Chem.*, 1995, pp. 6973-6979.

Jones, et. al. "Serious Flaws in Patterson (SOFE '95)Demo on Cold Fusion." available at http//x7.dejanews.com, Oct. 1995.

Joyce, et. al. "Ion Distribution functions in an Ar-CI ECR Discharge." *Plasma Sources Sci. Technol.*, vol. 9, 2000, pp. 429-436.

Judge, "SHE-2 Latest Solar EUV Measurements"(internet page) www.usc.edu/dept/space_science/seh2data.htm, Aug. 18, 1997.

Ivanco, et. al. "Calorimetry for a $Ni/K_2CO_3$ Cell." *AECL Research*, Jun. 1994.

Kahn. "Confusion in a Jar," *Nova*, 1991.

Karabut, et. al. "Nuclear Product . . . Deuterium." *Physics Letters A170*, 1992, pp. 265-272.

Karplus and Porter. *Atoms and Molecules: An Introduction for Students of Physical Chemistry*, The Benjamin/Cummings Publishing Company, Menlo Park, California, 1970, p. 3, 118-123.

Karplus and Porter. *Atoms and Molecules: An Introduction for Students of Physical Chemistry*, The Benjamin/Cummings Publishing Company, Menlo Park, California, 1970, p. 567.

Kawai, et. al. "Electron temperature, density, and metastable-atom density of argon electron-cyclotron-resonance plasma discharged by 7.0, 8.0, and 9.4 Ghz microwaves." *J. Vac. Sci. Technol. A*, vol. 18, No. 5, Sep./Oct. 2000, pp. 2207-2212.

Keefer, Ph.D., "Interim Report on BlackLight Power Technology: Its Apparent Scientific Basis, State of Development and Suitability for Commercialization by Liebert Corporation.".

Kerkhoff. "Zum photochemischen Verhalten sauerstoffhaltiger Komplexe in Alkalihalogenidkristalle." *Zeitschrift für Physik*, vol. 158, 1960, pp. 595-606.

Kerkhoff et al. "Elektronenspin-Resonanz und Photochemie des $U_2$-Zentrums in Alkalihalogenid-Kristallen." *Zeitschrift für Physik*, vol. 173, 1963, pp. 184-202.

Klein. "Attachments to Report of Cold Fusion Testing." *Cold Fusion*, No. 9, pp. 16-19.

Kleinschrod. "Photochemische Zersetzung von KH und KD in KBr-Kristallen." *Ausgegeban*, Jan. 5, 1939, pp. 143-148.

Kleppner, et. al. "One Hundred Years of Quantum Physics." *Science*, vol. 289, Aug. 2000, pp. 893-898.

Kline-Anderson, Inc. "Review of Schedule and Resource Requirements to Develop a Hydrocatalysis Functional Prototype Unit." Final Report for Technology Insights, Oct. 1996.

Kolos, et. al. "Accurate Adiabatic Treatment of the Ground State of the Hydrogen Molecule*." *Journal of Chemical Physics*, vol. 41, No. 12, Dec. 1964, pp. 3663-3673 (Paper I).

Kolos, et. al. "Accurate Electronic Wave Functions for the $H_2$ Molecule*." *Reviews of Modern Physics*, vol. 32, No. 2, Apr. 1960, pp. 219-232.

Kolos, et. al. "Improved Theoretical Ground-State Energy of the Hydrogen Molecule*." *Journal of Chemical Physics*, vol. 49, No. 1, Jul. 1968, pp. 404-410 (Paper II).

Kovacevic et. al. "The Dynamic Response of the Plasma on the Dust Formation in $Ar/C_2H_2$ RF Discharges." *International Conference on Phenomena in Ionized Gases* available at http://www.iopig.uni-greifswald.de/proceedings/data/kovacevic_1. (no date listed).

Kreig "Hydrinos: A state below the ground state" (internet page) www.phact.org/e/x/hydrino.htm and http://ww.freeenergies.org/b1/bwt/z/hydrino/hydrino.htm (date unknown).

Kreysa, et. al. "A Critical Analysis of Electrochemical Nuclear Fusion Experiments." *J. Electroanal. Chem.*, vol. 266, 1989, pp. 437-450.

Kuhn, H.G. "Atomic Spectra." Academic Press: NewYork. 1962. pp. 114-117.

Kuraica, et. al."Line Shapes of Atomic Hydrogen in a Plane-Cathode abnormal glow discharge."*Physical Review A*, Bol. 46. No. 7, Oct. 1992, pp. 4429-4432.

Kurunczi, et. al."Excimer formation in high-pressure micro hollow cathode discharge plasmas in helium initiated by low-energy electron collisions." *International Journal of Mass Spectrometry*, vol. 205, 2001, pp. 277-283.

Kurunczi, et. al."Hydrogen Lyman-α and Lyman-β emissions from high-pressure micro hollow cathode discharges in Ne-H2 mixtures" *J. Phys. B: At. Mol. Opt. Phys.*, vol. 32, 1999, pp. L651-L658.

Kurtz, et. al. "Report on Calometric Investigations of Gas-Phase Catalyzed Hydrino Formation."Hydrocatalysis Power Corp. Report, Dec. 1996.

http://omm.hut.fi/optics/I_o/2004/luennot/spectroscopv.pdf.

http://hyperphysics.phy-astrgsu.edu/hbase/kinetic/molke.html.

Labov. "Spectral Observations . . . Background." *The Astrophysical Journal*, vol. 371, Apr. 20, 1991, pp. 810-819.

F. Laloe, "Do we really understand quantum mechanics?" Am. J. Phys., vol. 69(6), (Jun. 2001), pp. 655-701.

Leggett, et. al. "Exact Upper Bound . . . 'Cold Fusion'." *Physical Review Letters*, vol. 63, No. 2, Jul. 1989, pp. 190-194.

"Lehigh X-Ray Photoelectron Spectroscopy Report." Dec. 8, 1993.

Lewis, et. al.,"Searches for Low-Temperature Nuclear Fusion of Deuterium in Palladium." *Nature*, vol. 340, Aug. 17, 1989, pp. 525-530.

Luggenholscher et al., "Investigations on Electric Field Distributions in a Microwave Discharge in Hyrdogen", available at http://www.phys.tue.nl/fltdd/luooenhoelscher.pdf (date unknown).

Lüpke. "Über Sensibilisierung der photochemischen Wirkung in Alkalihalogenidkristallen." *Annalen der Physik*, vol. 21, 1934, pp. 1-14.
Luque et. al. "Experimental research into the influence of ion dynamics when measuring the electron density from the Stark broadening of the Hα and Hβ lines." *Journal of Physics B: Atomic, Molecular, and Optical Physics*, vol. 36. 2003. pp. 1573-1584.
Lüty. "Über Die Natur Der $V_3$-Zentren in Strahlungsverfäbtem KCCl." *J. Phys. Chem. Solids*, vol. 23, 1962, pp. 677-681.
Maly, et. al. "Electron Transitions on Deep Dirac Levels I." *ANS Reprint, Fusion Technology*, vol. 24, Nov. 1993, pp. 307-318.
Marchese et. al. "The BlackLight Rocket Engine." Phase I Final Report, Rowan University: Glassboror, NJ. May 1-Nov. 30, 2002, available at www.niac.usra.edu/files/studies/finalreport. also available at http://engineering.rowan.edu/~marchese/.
Margenau, et. al. "The Mathematics of Physics and Chemistry." D. Van Nostrand *Yale University*, 1943, pp. 77-79.
Martiensen. "Photochemische Vorgänge in Alkalihalogenidkristallen." *Zeitschrift für Physik*, vol. 131, 1952, pp. 488-504.
"Material Hardness," http://www.calce.umd.edu/general/facilities/hardness_ad_htm.
Mayo, et. al. "On the Potential of Direct and MHD Conversion of Power from a Novel Plasma Source to Electricity for Micro distributed Power Applications", *IEEE Transactions on Plasma Science*, submitted.
McNally. "On the Possibility of a Nuclear Mass-Energy Resonance in D + D Reactions at Low Energy." *Fusion Technology*, vol. 16, No. 2, Sep. 1989, pp. 237-239.
McQuarrie. "Quantum Chemistry" University Science Books: Sausalito, CA. 1983 Sections 4-3, 6-4-6-9, 8-5-8-6 and pp. 221-222.
Merriaman, et. al., "An attempted replication of the CETI Cold Fusion Experiment." published on the Internet, May 1, 1997, available at www.math.ucla.edu/~barry/CF/Cetix.html, pp. 1-17.
Merzbacher, Eugen." Quantum Mechanics." 1961, p. 198.
Messiah, Albert. "Quantum Mechanics." *Rutgers-The State University*, vol. 1, 1958; p. 130.
Meulenbroeks, et. al. "The argon-hydrogen expanding plasma: model and experiments." *Plasma Sources Sci Technol.*, vol. 4, 1995, pp. 74-85.
Meulenbroeks, et. al. "Influence of molecular processes on the hydrogen atomic system in an expanding argon-hydrogen plasma." *Phys. Plasmas*, vol. 2, No. 3, Mar. 1995, pp. 1002-1008.
Miles et. al. "Correlation of Excess . . . Palladium Cathodes." *J. Electronl. Chem.*, 1993, pp. 99-117.
Miles et. al. "Electrochemical . . . Palladium Deuterium System." *J. Electroanal Chem.*, 1990, pp. 241-254.
Miles et. al. "Heat and Helium . . . Experiments." *Conference Proceedings*, vol. 33, 1991, pp. 363-372.
Miles, et. al. "Search for Anomalous Effects . . . Palladium Cathodes." *Naval Air Warfare Center Weapons Division, Proceedings of 3rd Int. Conf. on Cold Fusion*, Nagoya, Japan, Oct. 1992, pp. 21-25.
Miller. "Memo from Bennett Miller to Dr. Robert W. Bass." Oct. 9, 1997, pp. 1-10.
Miskelly, et. al. "Analysis of the Published Calorimetric Evidence for Electrochemical Fusion of Deuterium in Palladium." *Science*, vol. 246, No. 4931, Nov. 10, 1989, pp. 793-796.
Monroe, et. al. "A Schrodinger Cat Superposition State of an Atom." *Science*, vol. 272, May 24, 1996, pp. 1131-1101.
Morrison. "Cold Fusion Update No. 12, ICCPG." Jan. 17, 1997, available online at "www.skypoint.com".
Morrison. "Comments on claims of excess enthalpy by Fleischmann and Pons using simple cells made to boil." *Physics Letter A*, vol. 185, Feb. 28, 1994, pp. 498-502.
Morrison. "Review of Progress in Cold Fusion." *Transactions of Fusion Technology*, vol. 26, Dec. 1994, pp. 48-55.
Morrison, "Review of Cold Fusion," Sov. Phys. Usp. 34, Dec. 1991, pp. 1055-1060.
Morrison, "Cold Fusion Update No. 10," dated Apr. 1, 1995, available at http://www.skypoint.com/members/slogaianffiles/morrison.txt, pp. 1-8.

Morse, et. al. "Methods of Theoretical Physics," Part I, McGraw-Hill Book Co., Massachusetts Institute of Technology, Part 1: Chapters 1-8, 1953, pp. 808-903.
Myers, et. al. "Search for Cold Fusion at D/Pd > 1 Using Ion Implantation." *Journal of Fusion Energy*, vol. 9, No. 3, pp. 30-37, 1990.
Nakhmanson. "The Ghostly Solution of the Quantum Paradoxes and its Experimental Verification." *Frontiers of Fundamental Physics*. Plenum Press: New York. 1994. pp. 591-596, http://arxiv.org/ftp/physics/papers/0103/0103006.pdf.
Neynaber, et. al. "Formation of $HeH^+$ from Low-Energy Collisions of Metastable Helium and Molecular Hydrogen." *Journal of Chemical Physics*, vol. 57, No. 12, Dec. 16, 1972, pp. 5128-5137.
Niedra. "Replication of the Apparent Excess Heat Effect in Light Water . . . Cell." *NASA Technical Memorandum* 107167, Feb. 1996.
Nieminen. "Hydrogen atoms band together." *Nature*, vol. 356, Mar. 26, 1992, pp. 289-291.
NIST, "Atomic Spectroscopy—Spectral Line Shapes, etc.," available at: http://physics.nist. oov/Pubs/At Spec/node20html/.
NIST's Physical Reference Datasheet, "Energy Levels of Hydrogen and Deuterium," <URL http://physics.nist.gov/PhysRefData/HDEL/index.html>.
Noninski. "Excess Heat During the Electrolysis of a Light Water. . . Nickel Cathode." *Fusion Technology*, vol. 21, Mar. 1992, pp. 163-167.
Noninski, et. al. "Determination . . . Heavy Water." *Fusion Technology*, vol. 19, 1990, pp. 365-367.
Notoya. "Cold Fusion . . . Nickel Electrode." *Fusion Technology*, vol. 24, 1993, pp. 202-204.
Notoya. "Tritium Generation . . . Nickel Electrodes." *Fusion Technology*, vol. 26,1994, pp. 179-183.
Notoya, et. al. "Excess Heat Production in Electrolysis . . . Electrodes." *Proceedings of the Int. Conf. on Cold Fusion*, Oct. 21-25, 1992, Tokyo, Japan.
Odenthal et al., "The Zeeman Splitting of the 5876 Å Helium Line Studied by Means of a Turnable Dye Laser",*Physica*, pp. 203-216, 1982.
Ohashi, et. al. "Decoding of Thermal Data in Fleischmann & Pons Paper." *J. of Nucl. Sci.. & Tech.*, vol. 26, No. 7, Jul. 1989, pp. 729-732.
Ohmori, et. al. "Excess Heat Evolution . . . Tin Cathodes." *Fusion Technology*, vol. 24, 1993, pp. 293-295.
Oka, et. al. "$D_2O$-fueled fusion power reactor using electromagnetically induced $D-D_n$, $D-D_p$, and Deuterium-tritium reactions-preliminary design of a reactor system." *Fusion Technology*, vol. 16, No. 2, Sep. 1989, pp. 263-267.
Park, Robert L. "Perpetual Motion: Still Going Around." *Washington Post*, Jan. 12, 2000, p. H03.
Park, "Patent Nonsense, Court Denies BlackLight Power Appeal," What's New, Sep. 6, 2002, available at www.aps.org.wn/wn02/wn090602.html.
Park, What's New, Friday Mar. 17, 2006.
Park, What's New, Friday Jan. 13, 2006.
Park, What's New, Friday Apr. 26, 1991.
Pauling, et. al. "Introduction to Quantum Mechanics with Applications to Chemistry." Dover Publications, Inc., *Harvard University*, 1985, pp. 121-140.
Peterson. "Evaluation of Heat Production from Light Water Electrolysis Cell of Hydrocatalysis Power Corporation." Draft, *Westinghouse STC*, Feb 1994.
Phillips, et. al. "Additional Calorimetric Examples of Anomalous Heat From Physical Mixture of K/Carbon and PD/Carbon." Consulting Report, Jan. 1996.
Plasmaphysics.org. Conversion Table: cgs/SI- units. (internet page) www.plasmaphysics.org.uk/convers.htm. (no author or date listed).
Platt, Charles. "Testing the Current." *Washington Post*. Jun. 25, 2000, p. X05.
Physics 200-04 course, "Pauli Spin Matrices," http://axion.physics.ubc.ca/200-04/pauli-spin.pdf.
Physics Web Aug. 5, 2005, "Hydrogen results causes controversy".
Popov. "Electrochemical Characterization of BlackLight Power, Inc. MH as Electrodes for Li-ion Batteries." Department of Chemical Engineering University of South Carolina, Feb. 2000.
Powell et al. *Quantum Mechanics*, Addison-Weskey Publishing Co., Inc., pp. 205-229 and 478-482, 1961.

Price, et. al. "Search for Energetic-Charged Particle Emission from Deuterated Ti and Pd Foils." *Physical Review Letters*, vol. 63, No. 18, Oct. 30, 1989, pp. 1926-1929.

Quantum Physics 301, "Paradoxes and Interpretation," http://www.teach.phy.bris.ac.uk/leve13/phys30100/coursematerials/paradoxes.pdf.

Radavanov, et. al. "Ion Kinetic-Energy Distributions and Balmer-α Excitation in Ar-$H^2$ Radio-Frequency Discharges." *J. Appl. Phys.*, vol. 78, No. 2, Jul. 15, 1995, pp. 746-756.

Rathke "A Critical Analysis of the Hydrino Model", New Journal of Physics, May 19, 2005, http://www.iop.org/eu/article/1367-2630/7/1/127/nip5_1_127.html.

Rauch et. al. "Some F-Band Optical Oscillator Strengths in Additively Colored Alkali Halides." *Physical Review*, Feb. 1, 1957, vol. 105, pp. 914-920.

Rees. "Cold Fusion . . . What Do We Think?" *Journal of Fusion Energy*, vol. 10, No. 1, 1991, pp. 110-116.

Real Climate, Jan. 20, 2005, "Peer Review: A Necessary But Not Sufficient Condition," <http://www.realclimate.org/index.php?p=109>.

Roberts, et. al. "Hydrogen Balmer alpha line shapes for hydrogen-argon mixtures in a low-pressure rf discharge." J. App. Phys, vol. 74, No. 11, (Dec. 1993).

Rogers, et. al., "Cold Fusion Reaction Products and Their Measurement." *Journal of Fusion Technology*, vol. 9, No. 4, 1990, pp. 483-485.

Rogers. "Isotopic hydrogen fusion in metals." *Fusion Technology*, vol. 16, No. 2, Sep. 1989, pp. 2254-2259.

Rosenblum. "Celebrating Y2K Could Prevent Panic, Ease Transition." Re: (*ise-I*) *Institute for Social Ecology Newsletter*, Dec. 22, 1998.

Rosenblum. "Four Interviews With Dr. Randell Mills on New Energy, New Physics." Re: (*ise-1*) *Institute for Social Ecology Newsletter*, Feb. 2, 1998.

K. L. Ross, "Kantian Quantum Mechanics," http://www.friesian.com/space-2.htm.

Rothwell. "Italy-Cold Fusion & Judge's Verdict." *NEN*, vol. 4, No. 1, Mar. 26, 1996, available at www.padrak.com/ine/CFLIBEL.html, pp. 9-11.

Rousseau. "Case Studies in Pathological Science." *American Scientist*, vol. 80, 1992, pp. 54-63.

Rout, et. al. "Phenomenon of Low Energy Emissions from Hydrogen/Deuterium Loaded Palladium." $3^{rd}$ *Annual Conference on Cold Fusion*, Oct. 21-25, 1992.

Rudd, et. al. "Backward Peak in the Electron Spectrum from Collisions of 70-keV Protons with a Target from a Hydrogen-Atom Source." *Physical Review Letters*, vol. 68, No. 10, Mar. 1992, pp. 1504-1506.

Salamon, et. al. "Limits . . . Electrolytic Cells." *Nature*, vol. 344, Mar. 29, 1990, pp. 401-405.

Schaefer. "Das Ultrarote Spektrum Des U-Zentrums," *Phys. Chem. Solids*, 1960, vol. 12, pp. 233-244, Pergamon Press, Great Britain.

Schearer et al. "Microwave Saturation of Paraelectri-Resonance Transitions of OH⁻ Ions in Kc$\ell$" *Solid State Communications*, vol. 4, 1966, pp. 639-642.

Schiff, Leonard I. "Quantum Mechanics." *Stanford University*, 1968, pp. 1, 7-8, 10-12, 21, 54-57, 60-61, 81-82, 101, 527.

Schrieder, et. al. "Search for Cold Nuclear Fusion in Palladium-Deuterium." *Z. Phys. B-Condensed Matter*, vol. 76, No. 2, 1989, pp. 141-142.

Service. "Cold Fusion: Still Going." *Newsweek Focus*, Jul. 19, 1993.

Shani, et. al. "Evidence for a Background Neutron Enhanced Fusion in Deuterium Absorbed Palladium." *Solid State Communications*, vol. 72, No. 1, 1989, pp. 53-57.

Shaubach, et. al. "Anomalous Heat . . . Carbonate." *Thermacore, Inc.*, pp. 1-10.

Shelton, et. al. "An assessment of claims of 'excess heat' in 'cold fusion' calorimetry." *Elsevier Science B.V., Thermochimica Acta* 297,1997, pp. 7-15.

Shermer, "Baloney Detection", *Scientific American*, Nov. 2001.

Shkedi, et. al. "Calorimetry, Excess Heat, and Faraday Efficiency in Ni-$H_2$O Electrolytic Cells." *Fusion Technology*, vol. 28, Nov. 1995, pp. 1720-1731.

Shook. "A Pragmatically Realistic Philosophy of Science." *Pragmatic Naturalism and Realism*.Prometheus Books: Amherst, NY. 2003, http://www.pragmatism.ort/shook/pragmatic_and_realistic.htm.

Silvera, et. al. "Deuterated palladium at temperatures from 4.3 to 400K and pressures to 105 kbar; Search for cold fusion." *The American Physical Society*, Physical Review B, vol. 42, No. 14, Nov. 15, 1990, pp. 9143-9146.

Souw, Bernard, "Coherent Telescope array with self-homodyne interfermetric detection for optical communications," Opt. Eng. 42(11) 3139-3157 (Nov. 2003).

Souw et al., "Calculation of the Combined Zeeman and translational Stark Effect on the Hα-Multiplet", *Physica*, pp. 353-374, 1983.

E-K Souw, Ph.D. Thesis 1981, University of Dusseldorf, Germany, titled "Investigations of Transport Phenomena in the Wall Region of a Helium Plasma by Means of Spectroscopic Methods."

E.K.Souw, "Plasma Density Measurements in an Imperfect Microwave Cavity," J. Appl. Phys. 61 (1987) p. 1761-1772.

E-K Souw et al., "The Zeeman Splitting of the 5876 A He Line Studied by means of a Tunable Dye Laser," Physica 113c (1982) pp. 203-216.

E-K Souw, "Anomalous Broadening and Splitting of Hel and Arl lines in microwave plasmas," unpublished data, Dec. 1, 2003.

Srianand, et. al. "The cosmic microwave background radiation temperature at a redshift of 2.34." *Nature*, vol. 408, Dec. 2000, pp. 931-935.

Srinivasan, et. al. "Tritium and Excess Heat Generation during Electrolysis of Aqueous Solutions of Alkali Salts with Nickel Cathode." $3^{rd}$ *Annual Conference on Cold Fusion*, Oct. 21-25, 1992.

Stein. "Theory May Explain Cold Fusion Puzzle." *Lexis Reprint, Washington News*, Apr. 25, 1991.

"Stellar Spectra and the Secrets of Starlight" (Internet Pages) www.kingusa.ab.ca/~brian/asto/course/lectures/fall/a200110g.htm (date and author unknown).

Stripp. "Georgia Group Outlines Errors That Led to Withdrawal of Cold Fusion Claims." *The Wall Street Journal*, Apr. 26, 1989, p. B4.

Storms, et. al. "Electrolytic Tritium Production." *Fusion Technology*, vol. 17, Jul. 1990, pp. 680-695.

Suplee. "Two New Theories on Cold Fusion . . . Scientists." *The Washington Post $1^{st}$ Section*, 1991, p. A11.

Taubes. "Bad Science." *Random House*, 1993, pp. 303, 425-481.

Taubes. "Cold Fusion Conundrum at Texas A & M." *Science*, vol. 248, News & Comment, Jun. 15, 1990, pp. 1299-1304.

Taylor, et. al. "Search for neutrons from Deuterated palladium subject to high electrical currents." *Fourth International Conference on Cold Fusion*, Maui Hawaii, L.A-UR 94-970, May 4, 1994, pp. 1-11.

Technology Insights. "Draft: Hydrocatalysis Technical Assessment." PACIFICORP, Aug. 2, 1996.

Tegmark, et. al. "100 Years of Quantum Mysteries." *Scientific American*, Feb. 2001, pp. 68-75.

Thermacore, Inc. "SBIR Phase I Nascent Hydrogen: An Energy Source." Final Report, Mar. 1994.

Thomas. "Zur Photocjemie des KH-KBR-Mischjristalles." *Annalen der Physik*, vol. 38, 1940, pp. 601-608.

Thorne, et. al. "Recombination during the Electrolysis of Light Water in 0.6 M $K_2CO_3$ Can It Account for the Reports of Excess Heat?" *Departments of Physics and Chemistry, Brigham Young University*, Jun. 1993.

Time 2 wake up: "New Power Source that turns physics on its head," Nov. 9, 2005.

Tolman, Richard C. "The Principles of Statistical Mechanics." *California Institute of Technology*, 1979, pp. 180-188.

Turner. "Declaration of Dr. Gary L. Turner." Aug. 24, 2004.

U.S. Department of Commerce, Summary of Ethics Rules, USPTO, 2000; Oct. 15, 2004.

Vaselli et. al. "Screening Effect of Impurities in Metals: A possible Explanation of the Process of Cold Nuclear Fusion." 11 Nuovo Cimento Della Societa Italiana di Fisica, vol. 11D, No. 6, Jun. 1989, Bologna, Italy, pp. 927-932.

Videnovic, et al. "Spectroscopic investigations of a cathode fall region of the Grimm-type glow discharge." *Spectrochimica Acta Part B*, vol. 51, 1996, pp. 1707-1731.

Vigier. "New Hydrogen Energies in Specially Structured Dense Media : Capillary Chemistry and Capillary Fusion." *Proceedings of the Third Annual Conf. on Cold Fusion*, Nagoya, Japan, Oct. 21-25, 1992, H. Ikegami, Ed. Universal Academy Press., pp. 325-334.

Vigier. "New Hydrogen (Deuterium) Bohr Orbits." *Proc. ICCF4*, vol. 4, 1994, p. 7-10.

Welcome to MIT's OpenCourseWare Home Page. MIT 2005. http://oxw.mitedu/index.html.

Weisskopf, V.F. "Recent developments in the theory of the electron." *Reviews of Modern Physics*, vol. 21, No. 2, 1949, pp. 305-315.

Wheeler, et. al. "Quantum Theory and Measurement." English Translation of Heisenburg's Uncertainty Principle Paper, *Zeitschrift für Physik*, 1927, vol. 43, pp. 172-198.

Wikipedia, Chapter 9: "Peer Review and Fraud," <http://en.wikipedia.org/wiki/peer_review#peer_review_and_fraud>.

Williams. "Upper Bounds on Cold Fusion in Electrolytic Cells." *Nature*, vol. 342, Nov. 23, 1989, pp. 375-384.

Wilson, et. al. "Analysis of experiments on the calorimetry of L10D-$D_2O$ electrochemical cells." *Elsevier Sequoia S.A.*, Journal of Electroanalytical Chemistry, vol. 332, Nos. 1 and 2, Aug. 14, 1992, pp. 1-31.

"XPS (EASC)—SAM," http://www.noveonic.com/measurementscience/analyticalservices/xpsescasam.pdf.

Yamaguchi et. al. "Direct Evidence . . . Palladium." *NTT Basic Research Laboratories*, 1992 pp. 1-10.

Ziegler, et. al. "Electrochemical Experiments in Cold Nuclear-Fusion." *Physical Review Letters*, vol. 62, No. 25, Jun. 19, 1989, pp. 2929-2932.

Peter D. Zimmerman, "An Analysis of Theoretical Flaws in So-Called Classical Quantum Mechanics and of Experimental Evidence Against CQM" (2001).

Zweig, "Quark Catalysis of Exothermal Nuclear Reactions", Science, vol. 201, (1978), pp. 973-979.

Critchley et al, "Energy shifts and forbidden transitions in $H_2$ due to electronic g/u symmetry breaking", Molecular Physics, 2003, vol. 101, Nos. 4-5, pp. 651-661, Taylor & Francis Ltd.

Gambus et al., "Spectroscopic Study or Low-Pressure Water Plasmas and Their Reactions with Liquid Hydrocarbons", Energy & Fuels, 2002, 16, pp. 172-176, American Chemical Society.

Akatsuka et al., "Stationary population inversion of hydrogen in an arc-heated magnetically trapped expanding hydrogen-helium plasma jet", Physical Review E, 49, 2, pp. 1534-1544, Feb. 1994, The American Physical Society.

Murakami et al., "Chemisorption of hydrogen into a graphite-potassium intercalation compound $C_8K$ studied by means of position annihilation", J. Chem. Phys., 62 (10), May 15, 1995, American Institute of Physics.

Ahn, "Hydrogen Storage in Metal-Modified Single-Walled Carbon Nanotubes", Division of Engineering and Applied Science, California Institute of Technology, Sep. 15, 2001.

Duan et al., "Numerical calculation of energies of some excited states in a helium atom", Eur. Phys. J., D 19, (2002), pp. 9-12, Societa Italiana di Fisica, Springer-Verlag 2002.

Nixon et al., "Formation and structure of the potassium graphites", Brit. J. Appl. Phys., Ser. 2, vol. 1, pp. 291-299, Great Britain, 2002.

Zellinger, "Experiment and the foundations of quantum physics", Reviews of Modern Physics, vol. 71, No. 2, pp. S288-S297, Centenary 1999, The American Physical Society.

Cotton et al, "Complexes of Cyclic 2-Oxacarbenes, I. A Spontaneous Cyclization to Form a Complex of 2-Oxaclyclopentylidene", Journal of the American Chemical Society, 93:11, pp. 2672-2676, Jun. 2, 1971.

Lindsay et al., "A remeasurement of the 2.4 µm spectrum of J = H2 pairs in a parahydrogen crystal", Journal of Molecular Spectroscopy, 218. pp. 131-133, 2003.

Juarez et al, "Photoelectron angular distributions of rotationally resolved states in para-H2+ : A closer to the dynamics of molecular photoionisation", The University of Manchester Atomic, Molecular & Laser Manipulation Group, pp. 1-5.

Weisstein, "Ortho-Para Hydrogen", http://scienceworld.wolfram.com/physics/Ortho-ParaHydrogen.html.

Smith, "Infrared spectra of B02- in the alkali halides-L. Potassium and rubidium halides", Spectrochimica Acts, vol. 30A, pp. 875-882, Pergamon Press, 1974.

Leitch et al., "Raman Specreoscopy of Hydrogen Molecules in Crystalline Silicon", Physical Review Letters, 81:2, pp. 421-424, Jul. 13, 1998, The American Physical Society.

Chen et al., "Key to Understanding Interstitial H2 in Si", Physical Review Letters, 88:10, pp. 105507-1-105507-4, Mar. 11, 2002, The American Physical Society.

Chen et al., "Rotation of Molecular Hydrogen in Si: Unambiguous Identification of Ortho-H2 and Para-D2", Physical Review Letters, 88:24, pp. 245503-1-245503-4, Jun. 17, 2002, The American Physical Society.

Lavrov et al., "Ortho and Para Interstitial H2 in Silicon", Physical Review Letters, 89:21, pp. 215501-1-215501-4, Nov. 18, 2002, The American Physical Society.

Stavola et al, "Interstitial H2 in Si: are all problems solved?", Physica B, pp. 58-66, 200s Elsevier B.V.

Decius et al, "Force Constants of the Metaborate Ion in Alkali Halides", The Journal of Chemical Physics, 56:10, pp. 5189-5190, May 15, 1972.

Morgan, "Infrared spectra of the metaborate ion in alkali halide solid solution", Research Notes, pp. 600-602.

Smith, "Anharmonic force field of the metaborate ion in alkali halides", The Journal of Chemical physics, 58:11, pp. 4776-4778, Jun. 1, 1973.

Hisatsune et al., "Infrared Spectra of Metaborate Monomer and Trimer Ions", Inorganic Chemistry, pp. 168-174.

Jones et al., "Force Constants of Nickel Carbonyl from Vibrational Spectra of Isotopic Species", The Journal of Chemical Physics, 48:6, pp. 2663-2670, Mar. 15, 1968.

Smith, "Infrared spectra of B02-in the alkali halides-I. Potassium and rubidium halides", Spectrochimica Acta, 30A, pp. 875-882, 1974, Pergamon Press.

Schoenfelder et al., "Kinetics of Thermal Decomposition of TiH2", J. Vac. Sci. Technol., 10:5, pp. 862-870, Sep./Oct. 1973.

Heatwave Labs, "Emission Characteristics for Scandium Type Dispenser Cathodes", HeatWave Labs, Inc., TB-119, May 24, 2001, Spectra-Mat, Inc.

Heatwave Labs, "Emission Characteristics of 'M Type' Dispenser Cathodes", HeatWave Labs, Inc., TB-117, May 24, 2001, Spectra-Mat, Inc.

"Practical Aspects of Modern Dispenser Cathodes", Microwave Journal, Sep. 1979.

Heatwave Labs, "Standard Series Barium Tungsten Dispenser Cathodes", HeatWave Labs, Inc., TB-198, Jul. 29, 2002, Spectra-Mat, Inc.

Abate et al., "Optimization and enhancement of H– ions in a magnetized sheet plasma", Review of Scientific Instruments, 71:10, pp. 3689-3695, Oct. 2000, American Institute of Physics.

Chabert et al., "On the influence of the gas velocity on dissociation degree and gas temperature in a flowing microwave hydrogen discharge", Journal of Applied Physics, 84:1, pp. 161-167, Jul. 1, 2009, American Institute of Physics.

Gordon et al., "Energy coupling efficiency of a hydrogen microwave plasma reactor", Journal of Applied Physics, 89:3, pp. 1544-1549, Feb. 1, 2001, American Institute of Physics.

Radovanov et al., "Time-resolved Balmer-alpha emission from fast hydrogen atoms in low pressure, radio-frequency discharges in hydrogen", Appl. Phys. Lett., 66:20, pp. 2637-2639, May 15, 2995.

Djurovic et al., "Hydrogen Balmer alpha line shapes for hydrogen-argon mixtures in a low-pressure rf discharge", J. Appl. Phys., 74:11, pp. 6558-6565, Dec. 1, 1993, American Institute of Physics.

Konjevic, "Plasma Broadening and Shifting of Non-Hydrogenic Spectral Lines: Present Status and Applications", Physics Reports, 315, pp. 339-401, 1999, Elsevier.

Benesch et al., "Line shapes of atomic hydrogen in hollow-cathode discharges", Optics Letters, 9:8, pp. 338-340, Aug. 1984, Optical Society of America.

Ayers, et al., "Shapes of atomic-hydrogen lines produced at a cathode surface", Physical Review A, 37:1, pp. 194-200, Jan. 1, 1988, The American Physical Society.

Adamov, et al., "Doppler Spectroscopy of Hydrogen and Deuterium Balmer Alpha Line in an Abnormal Glow Discharge", IEEE Transactions on Plasma Science, 31:3, pp. 444-454, Jun. 3, 2003.

Jovicevic et al., "Excessive Balmer line broadcasting in microwave-induced discharges", Journal of Applied Physics, 95:1, pp. 24-29, Jan. 1, 2004, American Institute of Physics.

Djurovic et al., "Hydrogen Balmer alpha line shapes for hydrogen-argon mixtures in a low-pressure rf discharge", J. Appl. Phys., 74:11, pp. 6558-6565, Dec. 1, 1993, American Institute of Physics.

Mayo, "Thermalization and Energy Distribution in Cold Laboratory Plasmas Comments on the Possibility of Mono-Energetic Species", Apr. 20, 2004.

Videnovic et al., "Spectroscopic investigations of a cathode fall region of the Grimm-type glow discharge", Spectrochimica Acta Part B, 51, pp. 1707-1731, 1996.

Barbeau et al., Spectroscopic investigation of energetic atoms in a DC hydrogen flow discharge, pp. 1168-1174, 1990 IOP Publishing Ltd.

Konjevic et al., "Emission Spectroscopy of the Cathode Fall Region of an Analytical Glow", J. Phys. IV France, 7, pp. C4-247-C4-258, Oct. 1997.

Lifshitz et al., "Resonance absorption measurements of atom concentrations in reacting gas mixtures. I. Shapes of H and D Lyman-$\alpha$ lines from microwave sources", J. Chem. Phys., 70:12, pp. 5607-5613, Jun. 15, 1979, American Institute of Physics.

Kuraica et al., "Line shapes of atomic hydrogen in a plane—cathode abnormal glow discharge", Physical Review A, 46:7, pp. 4429-4432, Oct. 1, 1992, The American Physical Society.

Kuraica et al., "On the Atomic Hydrogen Line Shapes in a Plane-Cathode Obstructed Glow Discharge", Physica Scripta., 50, pp. 487-492, 1994.

Olthoff et al., "Studies of Ion Kinetic-Energy Distributions in the Gaseous Electronics Conference RF Reference Cell", Journal of Research of the National Institute of Standards and Technology, 100:4, pp. 383-400, Jul.-Aug. 1995.

Alexeff et al., "Collisionless Ion-Wave Propagation and the Determination of the Compressions Coefficient of Plasma Electrons", Physical Review Letters, 15:7, pp. 286-288, Aug. 16, 1999.

Arata et al., "Reproducible 'Cold' Fusion Reaction Using a Complex Cathode", Fusion Technology, 22, pp. 287-295, Sep. 1992.

Burkholder et al., "Reactions of boron atoms with molecular oxygen. Infrared spectra of BO, BO2, B2O2, B2O3, and BO2 in solid argon", J. Chem. Phys., 95:12, pp. 8697-8709, Dec. 15, 1991.

Spurgin, "Direct Conversion of the Random Thermal Energy of a Plasma Into Electrical Energy", Master's Thesis, The University of South Florida, Jun. 1972.

Technology Insights, "Hydro Catalysis Technical Assessment," (Part of U.S. Appl. No. 09/009,837 paper No. 20050207. This document was submitted by R. Mills on Jul. 17, 2002 in copending U.S. Appl. No. 09/669,877).

Ess, Notes on David Peat, "Einstein's Moon: Bell's Theorem and the Curious Quest for Quantum Reality," History and Philosophy of Science-Fall, 1997-Dr. Ess, <www.drury.edu/ess/philsci/bell.html>.

"Average Molecular Kinetic Energy", <http://hyperphysics.phy-astr.gsu.edu/hbase/kinetic/molke.html>.

K. Akhtar, J. Scharer, R. L. Mills, "Substantial Doppler Broadening of Atomic Hydrogen Lines in DC and Capactively Coupled RF Plasmas," IEEE Transactions on Plasma Science, submitted. (Internet Publication Date: Jun. 6, 2006.).

R.L. Mills, H. Zea, J. He, B. Dhandapani, "Water Bath Calorimetry on a Catalytic Reaction of Atomic Hydrogen," International Journal of Hydrogen Energy, in press. (Internet Publication Date: May 12, 2006).

R.L. Mills, K. Akhtar, B. Dhandapani, "Tests of Features of Field-Acceleration Models for the Extraordinary Selective H Balmer $\alpha$ Broadening in Certain Hydrogen Mixed Plasmas," J. Plasma Phys., submitted. (Internet Publication Date: Jun. 24, 2005.).

R.L. Mills, "Physical Solutions of the Nature of the Atom, Photon, and Their Interactions to Form Excited and Predicted Hydrino States," Physics Essay, in press.. (Internet Publication Date: Jun. 9, 2005).

R. L. Mills, J. He, Y. Lu, Z, M. Nansteel, Chang, B. Dhandapani, "Comprehensive Identification and Potential Applications of New States of Hydrogen," Int. J. Hydrogen Energy, vol. 32, (2007), 2988-3009. (Internet Publication Date: May 9, 2005.).

R. L. Mills, J. He, Z, Chang, W. Good, Y. Lu, B. Dhandapani, "Catalysis of Atomic Hydrogen to Novel Hydrogen Species $H^-$ (1/4) and H2(1/4) as a New Power Source," International Journal of Hydrogen Energy, vol. 32(13), (2007), pp. 2573-2584. (Internet Publication Date: May 6, 2005.).

R. L. Mills, J. He, Z, Chang, W. Good, Y. Lu, B. Dhandapani, "Catalysis of Atomic Hydrogen To Novel Hydrides as a New Power Source," Prepr. Pap.—Am. Chem. Soc., Div. Fuel Chem. 2005, 50(2). (Internet Publication Date: Apr. 22, 2005.).

R. L. Mills, M. Nansteel, J. He, B. Dhandapani, "Low-Voltage EUV and Visible Light Source Due to Catalysis of Atomic Hydrogen," J. Plasma Physics, submitted. (Internet Publication Date: Apr. 15, 2005).

R. L. Mills, J. He, M. Nansteel, B. Dhandapani, "Catalysis of Atomic Hydrogen to New Hydrides as a New Power Source," International Journal of Global Energy Issues (IJGEI). Special Edition in Energy Systems, in press. (Internet Publication Date: Apr. 4, 2005.).

R. L. Mills, "Maxwell's Equations and QED: Which is Fact and Which is Fiction," Physics Essays, in press. (Internet Publication Date: Oct. 28, 2004.).

R. L. Mills, "Exact Classical Quantum Mechanical Solution for Atomic Helium which Predicts Conjugate Parameters from a Unique Solution for the First Time," Physics Essays, submitted (Internet Publication Date: Oct. 28, 2004.).

J. Phillips, C. K. Chen, R. L. Mills, "Evidence of Catalytic Production of Hot Hydrogen in RF-Generated Hydrogen/Argon Plasmas," International Journal of Hydrogen Energy, vol. 32, (2007), 3010-3025. (Internet Publication Date: Sep. 7, 2004.).

R. L. Mills, Y. Lu, M. Nansteel, J. He, A. Voigt, W. Good, B. Dhandapani, "Energetic Catalyst-Hydrogen Plasma Reaction as a Potential New Energy Source," Division of Fuel Chemistry, Session: Advances in Hydrogen Energy, 228th American Chemical Society National Meeting, Aug. 22-26, 2004, Philadelphia, PA.

R. L. Mills, Dhandapani, W. Good, J. He, "New States of Hydrogen Isolated from $K_2CO_3$ Electrolysis Gases," Chemical Engineering Science, submitted. (Internet Publication Date: Apr. 28, 2004.).

R. L. Mills, "Exact Classical Quantum Mechanical Solutions for One- through Twenty-Electron Atoms," Phys. Essays, vol. 18, No. 3(2005), 321-361. (Internet Publication Date: Apr. 22. 2004).

Mills et al. "Energetic Catalyst-Hydrogen Plasma Reaction as a Potential New Energy Source," Division of Fuel Chemistry, Session: Chemistry of Solid, Liquid, and Gaseous Fuels, 227th American Chemical Society National Meeting, Mar. 28-Apr. 1, 2004, Anaheim, CA.

Mills et al., "Highly Stable Amorphous Silicon Hydride from a Helium Plasma Reaction," Materials Chemistry and Physics, 94/2-3, (2005), pp. 298-307. (Internet Publication Date: Nov. 17, 2003).

Mills et al., "Spectral Identification of H2(1/2)," submitted.

R. L. Mills, Y. Lu, J. He, M. Nansteel, P. Ray, X. Chen, A. Voigt, B. Dhandapani, "Spectral Identification of New States of Hydrogen," New Journal of Chemistry, submitted. (Internet Publication Date: Nov. 18, 2003).

Mills et al., "Evidence of an Energy Transfer Reaction Between Atomic Hydrogen and Argon II or Helium II as the Source of Excessively Hot H Atoms in RF Plasmas," Journal of Plasma Physics, vol. 72, Issue 4, (2006), pp. 469-484. (Internet Publication Date: Sep. 26, 2003.).

Mills et al., "Evidence of the Production of Hot Hydrogen Atoms in RF Plasmas by Catalytic Reactions Between Hydrogen and Oxygen Species," J. Plasma Phys., submitted. (Internet Publication Date: Sep. 12, 2003.).

Mills et al., "Excessive Balmer $\alpha$ Line Broadening of Water-Vapor Capacitively-Coupled RF Discharge Plasmas," IEEE Transactions on Plasma Science, submitted. (Internet Publication Date: Aug. 18, 2003.).

Mills, "The Nature of the Chemical Bond Revisited and an Alternative Maxwellian Approach," Physics Essays, vol. 17, (2004), pp. 342-389. (Internet Publication Date: Aug. 6, 2003.).

Mills et al., "Energetic Catalyst-Hydrogen Plasma Reaction Forms a New State of Hydrogen," Doklady Chemisty, submitted.

Mills et al., "Energetic Catalyst-Hydrogen Plasma Reaction as a Potential New Energy Source," Central European Journal of Physics, submitted. (Internet Publication Date: Jun. 6, 2003.).

R. Mills, P. Ray, "New H I Laser Medium Based on Novel Energetic Plasma of Atomic Hydrogen and Certain Group I Catalysts," J. Plasma Physics, submitted.

Mills et al., "Characterization of Energetic Catalyst-Hydrogen Plasma Reaction as a Potential New Energy Source," Am. Chem. Soc. Div. Fuel Chem. Prepr., vol. 48, No. 2, (2003).

Mills et al., "Hydrogen Plasmas Generated Using Certain Group I Catalysts Show Stationary Inverted Lyman Populations and Free-Free and Bound-Free Emission of Lower-Energy State Hydride," Fizika A, submitted.

Mills et al., "Role of Atomic Hydrogen Density and Energy in Low Power CVD Synthesis of Diamond Films," Thin Solid Films, 478, (2005), pp. 77-90. (Internet Publication Date: Dec. 22, 2003.).

Mills et al., "Liquid-Nitrogen-Condensable Molecular Hydrogen Gas Isolated from a Catalytic Plasma Reaction," J. Phys. Chem. B, submitted.

Mills et al., "Novel Spectral Series from Helium-Hydrogen Evenson Microwave Cavity Plasmas that Matched Fractional-Principal-Quantum-Energy-Level Atomic and Molecular Hydrogen," European Journal of Physics, submitted. (Internet Publication Date: Apr. 24, 2003.).

Mills et al., "Highly Pumped Inverted Balmer and Lyman Populations," New Journal of Physics, submitted.

Mills et al., "Comparison of Balmer α Line Broadening and Power Balances of Helium-Hydrogen Plasma Sources," Braz. J. Phys., submitted. (Internet Publication Date: Mar. 12, 2003.).

Mills et al., "Comparison of Water-Plasma Sources of Stationary Inverted Balmer and Lyman Populations for a CW HI Laser," J. Appl. Spectroscopy, in preparation.

Mills et al., "Synthesis and Characterization of Diamond Films from MPCVD of an Energetic Argon-Hydrogen Plasma and Methane," Journal of Materials Science, submitted. (Internet Publication Date: May 7, 2003.).

R. Mills, et. al., "Spectroscopic and NMR Identification of Novel Hydride Ions in Fractional Quantum Energy States Formed by an Exothermic Reaction of Atomic Hydrogen with Certain Catalysts," European Physical Journal: Applied Physics, 28, (2004), pp. 83-104. (Internet Publication Date: Feb. 21, 2003.).

Mills, "The Fallacy of Feynman's Argument on the Stability of the Hydrogen Atom According to Quantum Mechanics," Annales De La Fundation Louis De Broglie, vol. 30, No. 2, (2005), pp. 129-151. (Internet Publication Date: Jan. 27, 2003.).

Mills et al., "Comparison of Catalysts and Microwave Plasma Sources of Vibrational Spectral Emission of Fractional-Rydberg-State Hydrogen Molecular Ion," Canadian Journal of Physics, submitted.

Mills et al., "Vibrational Spectral Emission of Fractional-Principal-Quantum-Energy-Level Molecular Hydrogen", J. of the Physical Society of Japan, submitted. (Internet Publication Date: Sep. 9, 2002.).

Mills et al., "Water Bath Calorimetric Study of Excess Heat in 'Resonant Transfer' Plasmas," Journal of Applied Physics, vol. 96, No. 6, (2004), pp. 3095-3102. (Internet Publication Date: Jun. 16, 2003.).

Mills et al., "Comparison of Catalysts and Microwave Plasma Sources of Spectral Emission of Fractional-Principal-Quantum-Energy-Level Atomic and Molecular Hydrogen," Journal of Applied Spectroscopy, submitted. (Internet Publication Date: Feb. 12, 2002.).

Mills et al., "Novel Liquid-Nitrogen-Condensable Molecular Hydrogen Gas," Acta Physica Polonica A, submitted. (Internet Publication Date: Oct. 29, 2002.).

Mills et al., "Spectroscopic Study of Unique Line Broadening and Inversion in Low Pressure Microwave Generated Water Plasmas," Journal of Plasma Physics, vol. 71, Part 6, (2005), pp. 877-878. (Internet Publication Date: Jun. 18, 2003.).

Mills et al., "Energetic Helium-Hydrogen Plasma Reaction," Aiaa Journal, submitted (Internet Publication Date: Jul. 26, 2002.).

R. L. Mills, M. Nansteel, P. C. Ray, "Bright Hydrogen-Light and Power Source due to a Resonant Energy Transfer with Strontium and Argon Ions," Vacuum, submitted.

Mills et al., "Power Source Based on Helium-Plasma Catalysis of Atomic Hydrogen to Fractional Rydberg States," Contributions to Plasma Physics, submitted.

Mills et al., "Comparison of Catalysts and Plasma Sources of Vibrational Spectral Emission of Fractional-Rydberg-State Hydrogen Molecular Ion," The European Journal of Applied Physics, submitted. (Internet Publication Date: Sep. 2, 2002.).

Mills et al., "Spectroscopic Characterization of the Atomic Hydrogen Energies and Densities and Carbon Species During Helium-Hydrogen-Methane Plasma CVD Synthesis of Diamond Films," Chemistry of Materials, vol. 15, (2003), pp. 1313-1321. (Internet Publication Date: Dec. 31, 2002.).

Mills, et. al. "Stationary Inverted Balmer and Lyman Populations for a CW HI Water-Plasma Laser." IEEE Transactions on Plasma Science, submitted. (Internet Publication Date: Aug. 16, 2002).

Mills et al., "Extreme Ultraviolet Spectroscopy of Helium-Hydrogen Plasma," J. Phys. D, vol. 36, (2003), pp. 1535-1542. (Internet Publication Date: Jul. 17, 2002.).

Mills et al., "Spectroscopic Evidence for a Water-Plasma Laser," Europhysics Letters, submitted. (Internet Publication Date: Sep. 19, 2002.).

Mills et al.,"Spectroscopic Evidence for Highly Pumped Balmer and Lyman Populations in a Water-Plasma," J. of Applied Physics, submitted. (Internet Publication Date: Sep. 18, 2002.).

Mills et al., "Low Power MPCVD of Diamond Films on Silicon Substrates," Journal of Vacuum Science & Technology A, submitted. (Internet Publication Date: Jun. 26, 2002.).

Mills et al., "Plasma Power Source Based on a Catalytic Reaction of Atomic Hydrogen Measured by Water Bath Calorimetry," Thermochimica Acta, vol. 406, Issue 1-2, (2003), pp. 35-53. (Internet Publication Date: Jun. 25, 2002.).

Mills et al., "Synthesis and Spectroscopic Identification of Lithium Chloro Hydride," Inorganica Chimica Acta, submitted.

Mills et al., "Highly Stable Amorphous Silicon Hydride," Solar Energy Materials & Solar Cells, vol. 80, No. 1, (2003), pp. 1-20. (Internet Publication Date: Apr. 15, 2002.).

Mills et al., "Synthesis of HDLC Films from Solid Carbon," Journal of Materials Science, vol. 39, (2004), pp. 3309-3318. (Internet Publication Date: May 3, 2002.).

Mills et al., "The Potential for a Hydrogen Water-Plasma Laser," Applied Physics Letters, vol. 82, No. 11, (2003), pp. 1679-1681. (Internet Publication Date: Jul. 11, 2002.).

Mills, "Classical Quantum Mechanics," Physics Essays, vol. 16, (2003), pp. 433-498 (Internet Publication Date: May 23, 2002.).

Mills, et. al. "Spectroscopic Characterization of Stationary Inverted Lyman Populations and Free-Free and Bound-Free Emission of Lower-Energy State Hydride Ion Formed by a Catalytic Reaction of Atomic Hydrogen and Certain Group I Catalysts, J. of Quantitative Spectroscopy and Radiative Transfer," No. 39, sciencedirect.com, Apr. 17, 2003.

R. M. Mayo, R. Mills, "Direct Plasmadynamic Conversion of Plasma Thermal Power to Electricity for Microdistributed Power Applications," 40th Annual Power Sources Conference, Cherry Hill, NJ, Jun. 10-13, 2002, pp. 1-4. (Internet Publication Date: Mar. 28, 2002.).

Mills et al., "Chemically-Generated Stationary Inverted Lyman Population for a CW HI Laser," European J of Phys. D, submitted. (Internet Publication Date: Apr. 22, 2002.).

Mills et al., "Stationary Inverted Lyman Population Formed from Incandescently Heated Hydrogen Gas with Certain Catalysts," J. Phys. D, Applied Physics, vol. 36, (2003), pp. 1504-1509. (Internet Publication Date: Mar. 20, 2002) also submitted to Chem Phys. Letts.

Mills, "A Maxwellian Approach to Quantum Mechanics Explains the Nature of Free Electrons in Superfluid Helium." Braz. J. Phys, submitted. (Internet Publication Date: Jun. 4, 2002).

Mills et al., "Bright Hydrogen-Light Source due to a Resonant Energy Transfer with Strontium and Argon Ions," New Journal of Physics, vol. 4, (2002), pp. 70.1-70.28. (Internet Publication Date: Oct. 2002).

Mills et al., "CW HI Laser Based on a Stationary Inverted Lyman Population Formed from Incandescently Heated Hydrogen Gas with Certain Group I Catalysts," IEEE Transactions on Plasma Science, vol. 31, No. 2, (2003), pp. 236-247. (Internet Publication Date: Feb. 4, 2002.).

Mills et al., "Spectral Emission of Fractional-Principal-Quantum-Energy-Level Atomic and Molecular Hydrogen," Vibrational Spectroscopy, vol. 31, No. 2, (2003), pp. 195-213.

Mills et al., "Comparison of Excessive Balmer Line Broadening of Inductively and Capacitively Coupled RF, Microwave, and Glow Discharge Hydrogen Plasmas with Certain Catalysts," IEEE Transactions on Plasma Science, vol. 31, No. 3, (2003), pp. 338-355. (Internet Publication Date: Sep. 17, 2002.).

Mills et al., "Direct Plasmadynamic Conversion of Plasma Thermal Power to Electricity," IEEE Transactions on Plasma Science, Oct. 2002, vol. 30, No. 5, pp. 2066-2073. (Internet Publication Date: Mar. 26, 2002.).

H. Conrads, R. Mills, Th. Wrubel, "Emission in the Deep Vacuum Ultraviolet from a Plasma Formed by Incandescently Heating Hydrogen Gas with Trace Amounts of Potassium Carbonate," Plasma Sources Science and Technology, vol. 12, (2003), pp. 389.

Mills et al., "Emission in the Deep Vacuum Ultraviolet from a Plasma Formed by Incandescently Heating Hydrogen Gas with Trace Amounts of Potassium Carbonate," Plasma Sources Science and Technology, vol. 12, (2003), pp. 389-395.

Mills et al., "Synthesis and Characterization of a Highly Stable Amorphous Silicon Hydride as the Product of a Catalytic Helium-Hydrogen Plasma Reaction," Int. J. Hydrogen Energy, vol. 28, No. 12, (2003), pp. 1401-1424. (Internet Publication Date: Apr. 15, 2002.).

Mills, et. al. "Synthesis and Characterization of Lithium Chloro Hydride", International Journal of Hydrogen Energy, submitted. (Internet Publication Date: Jan. 7, 2002.).

Mills et al., "Substantial Changes in the Characteristics of a Microwave Plasma Due to Combining Argon and Hydrogen," New Journal of Physics, www.njp.org, vol. 4, (2002), pp. 22.1-22.17. (Internet Publication Date: Dec. 27, 2001.).

Mills et al., "A Comprehensive Study of Spectra of the Bound-Free Hyperfine Levels of Novel Hydride Ion, Hydrogen, Nitrogen, and Air," Int. J. Hydrogen Energy, vol. 28, No. 8, (2003), pp. 825-871. (Internet Publication Date: Nov. 14, 2001.).

Mills et al., "Novel Alkali and Alkaline Earth Hydrides for High Voltage and High Energy Density Batteries," Proceedings of the 17th Annual Battery Conference on Applications and Advances, California State University, Long Beach, CA, (Jan. 15-18, 2002), pp. 1-6. (Internet Publication Date: Nov. 9, 2001.).

Mills et al., "On the Potential of Direct and MHD Conversion of Power from a Novel Plasma Source to Electricity for Microdistributed Power Applications," IEEE Transactions on Plasma Science, Aug. 2002, vol. 30, No. 4, pp. 1568-1578. (Internet Publication Date: Nov. 12, 2001.).

Mills et al., "Stationary Inverted Lyman Populations and Free-Free and Bound-Free Emission of Lower-Energy State Hydride Ion Formed by an Exothermic Catalytic Reaction of Atomic Hydrogen and Certain Group I Catalysts," J. Phys. Chem. A, submitted. (Internet Publication Date: Nov. 13, 2001.).

Mills et al., "Highly Stable Novel Inorganic Hydrides from Aqueous Electrolysis and Plasma Electrolysis," Electrochimica Acta, vol. 47, No. 24, (2002), pp. 3909-3926. (Internet Publication Date: Jun. 13, 2002.).

Mills et al., "Comparison of Excessive Balmer Line Broadening of Glow Discharge and Microwave Hydrogen Plasmas with Certain Catalysts," J. Of Applied Physics, (2002), vol. 92, No. 12, pp. 7008-7022. (Internet Publication Date: Oct. 9, 2002.).

Mills et al., "Emission Spectroscopic Identification of Fractional Rydberg States of Atomic Hydrogen Formed by a Catalytic Helium-Hydrogen Plasma Reaction," Vacuum, submitted. (Internet Publication Date: Oct. 9, 2001.).

Mills et al., "New Power Source from Fractional Rydberg States of Atomic Hydrogen," Current Appl. Phys., submitted. (Internet Publication Date: Oct. 9, 2001.).

Mills et al., "Spectroscopic Identification of Transitions of Fractional Rydberg States of Atomic Hydrogen," J. of Quantitative Spectroscopy and Radiative Transfer, in press. (Internet Publication Date: Oct. 9, 2001.).

Mills et al., "New Power Source from Fractional Quantum Energy Levels of Atomic Hydrogen that Surpasses Internal Combustion," J Mol. Struct., vol. 643, No. 1-3, (2002), pp. 43-54. (Internet Publication Date: Oct. 10, 2001.).

Mills et al., "Spectroscopic Identification of a Novel Catalytic Reaction of Rubidium Ion with Atomic Hydrogen and the Hydride Ion Product," Int. J. Hydrogen Energy, vol. 27, No. 9, (2002), pp. 927-935. (Internet Publication Date: Sep. 19, 2001.).

Mills et al., "Measurement of Energy Balances of Noble Gas-Hydrogen Discharge Plasmas Using Calvet Calorimetry," Int. J. Hydrogen Energy, vol. 27, No. 9, (2002), pp. 967-978. (Internet Publication Date: Sep. 14, 2001.).

Mills et al., "Measurement of Hydrogen Balmer Line Broadening and Thermal Power Balances of Noble Gas-Hydrogen Discharge Plasmas," Int. J. Hydrogen Energy, vol. 27, No. 6, (2002), pp. 671-685. (Internet Publication Date: Aug. 22, 2001.).

Mills et al., "Vibrational Spectral Emission of Fractional-Principal-Quantum-Energy-Level Hydrogen Molecular Ion," Int. J. Hydrogen Energy, vol. 27, No. 5, (2002), pp. 533-564. (Internet Publication Date: Jul. 19, 2001.).

Mills et al., "Spectral Emission of Fractional Quantum Energy Levels of Atomic Hydrogen from a Helium-Hydrogen Plasma and the Implications for Dark Matter," Int. J. Hydrogen Energy, (2002), vol. 27, No. 3, pp. 301-322. (Internet Publication Date: Aug. 1, 2001.).

Mills, et. al. "Spectroscopic Identification of a Novel Catalytic Reaction of Potassium and Atomic Hydrogen and the Hydride Ion Product", International Journal of Hydrogen Energy, vol. 27, No. 2, (2002), pp. 183-192. (Internet Publication Date: Jan. 11, 2002).

Mills, "BlackLight Power Technology—A New Clean Hydrogen Energy Source with the Potential for Direct Conversion to Electricity," Proceedings of the National Hydrogen Association, 12th Annual U.S. Hydrogen Meeting and Exposition, Hydrogen: The Common Thread, The Washington Hilton and Towers, Washington DC, (Mar. 6-8, 2001), pp. 671-697. (Presented at the conference on Mar. 7, 2001; Internet Publication Date: Apr. 20, 2001.).

Mills, et. al. "Minimum heat of formation of potassium iodo hydride." International Journal of Hydrogen Energy, vol. 26, 2001, pp. 1199-1208. (Internet Publication Date: Mar. 23, 2001).

Mills, et al. "Stereoscopic Identification of a Novel Catalytic Reaction of Atomic Hydrogen and the hydride ion product." International Journal of Hydrogen Energy, vol. 26. 2001. pp. 1041-1058. (Internet Publication Date: Mar. 23, 2001.).

Mills et al., "Optically Measured Power Balances of Glow Discharges of Mixtures of Argon, Hydrogen, and Potassium, Rubidium, Cesium, or Strontium Vapor," Int. J. Hydrogen Energy, vol. 27, No. 6, (2002), pp. 651-670. (Internet Publication Date: Jul. 20, 2001.).

Mills, "The Grand Unified Theory of Classical Quantum Mechanics," Global Foundation, Inc. Orbis Scientiae entitled the Role of Attractive and Repulsive Gravitational Forces in Cosmic Acceleration of Particles The Origin of the Cosmic Gamma Ray Bursts, (29th Conference on High Energy Physics and Cosmology Since 1964) Dr. Behram N. Kursunoglu, Chairman, Dec. 14-17, 2000, Lago Mar Resort, Fort Lauderdale, FL, Kluwer Academic/Plenum Publishers, New York, pp. 243-258. (Presented at the conference on Dec. 15, 2000. (Internet Publication Date: May 17, 2001.).

Mills, "The Grand Unified Theory of Classical Quantum Mechanics," Int. J. Hydrogen Energy, vol. 27, No. 5, (2002), pp. 565-590. (Internet Publication Date: Sep. 17, 2001.).

Mills et al., "Argon-Hydrogen-Strontium Discharge Light Source," IEEE Transactions on Plasma Science, vol. 30, No. 2, (2002), pp. 639-653. (Internet Publication Date: Dec. 7, 2000.).

Mills et al., "Identification of Compounds Containing Novel Hydride Ions by Nuclear Magnetic Resonance Spectroscopy," Int. J. Hydrogen Energy, vol. 26, No. 9, (2001), pp. 965-979. (Internet Publication Date: Mar. 22, 2001.).

Mills, "BlackLight Power Technology—A New Clean Energy Source with the Potential for Direct Conversion to Electricity," Global Foundation International Conference on "Global Warming and Energy Policy," Dr. Behram N. Kursunoglu, Chairman, Fort Lauderdale, FL, Nov. 26-28, 2000, Kluwer Academic/Plenum Publishers, New York, pp. 187-202. (Presented at the conference on Nov. 26, 2000. (Internet Publication Date: Jan. 19, 2001.).

Mills, "The Nature of Free Electrons in Superfluid Helium—a Test of Quantum Mechanics and a Basis to Review its Foundations and Make a Comparison to Classical Theory," Int. J. Hydrogen Energy, vol. 26, No. 10, (2001), pp. 1059-1096. (Internet Publication Date: Dec. 11, 2000.).

Mills et al., "Excessively Bright Hydrogen-Strontium Plasma Light Source Due to Energy Resonance of Strontium with Hydrogen," J. of Plasma Physics, vol. 69, (2003), pp. 131-158. (Internet Publication Date: Aug. 27, 2001.).

Mills et al., "Observation of Extreme Ultraviolet Hydrogen Emission from Incandescently Heated Hydrogen Gas with Certain Catalysts," Int. J. Hydrogen Energy, vol. 25, (2000), pp. 919-943. (Internet Publication Date: Jun. 27, 2000.).

R. Mills, "Observation of Extreme Ultraviolet Emission from Hydrogen-KI Plasmas Produced by a Hollow Cathode Discharge," Int. J. Hydrogen Energy, vol. 26, No. 6, (2001), pp. 579-592. (Internet Publication Date: Jul. 10, 2000.).

Mills, "Temporal Behavior of Light-Emission in the Visible Spectral Range from a Ti-K2CO3-H-Cell," Int. J. Hydrogen Energy, vol. 26, No. 4, (2001), pp. 327-332. (Internet Publication Date: Jul. 10, 2000.).

Mills et al., "Formation of a Hydrogen Plasma from an Incandescently Heated Hydrogen-Catalyst Gas Mixture with an Anomalous Afterglow Duration," Int. J. Hydrogen Energy, vol. 26, No. 7, Jul. 2001, pp. 749-762. (Internet Publication Date: Jun. 28, 2000.).

Mills et al., "Observation of Extreme Ultraviolet Hydrogen Emission from Incandescently Heated Hydrogen Gas with Strontium that Produced an Anomalous Optically Measured Power Balance," Int. J. Hydrogen Energy, vol. 26, No. 4, (2001), pp. 309-326. (Internet Publication Date: Jun. 27, 2000.).

Mills et al., "Synthesis and Characterization of Potassium Iodo Hydride," Int. J. of Hydrogen Energy, vol. 25, Issue 12, (Dec. 2000), pp. 1185-1203. (Internet Publication Date: Nov. 12, 2001.).

Mills. "Novel inorganic hydride." International Journal of Hydrogen Energy, vol. 25, 2000, pp. 669-683. (Internet Publication Date: Jun. 28, 2000).

Mills et al., "Synthesis and Characterization of Novel Hydride Compounds," Int. J. of Hydrogen Energy, vol. 26, No. 4, (2001), pp. 339-367. (Internet Publication Date: Jun. 13, 2001.).

R. Mills, "Highly Stable Novel Inorganic Hydrides," Journal of New Materials for Electrochemical Systems, vol. 6, (2003), pp. 45-54. (Internet Publication Date: Nov. 20, 2001.).

R. Mills, "Novel Hydrogen Compounds from a Potassium Carbonate Electrolytic Cell," Fusion Technology, vol. 37, No. 2, (Mar. 2000), pp. 157-182. (Internet Publication Date: Jun. 26, 2000.).

Mills, "The Hydrogen Atom Revisited," Int. J. of Hydrogen Energy, vol. 25, Issue 12, Dec. 2000, pp. 1171-1183. (Internet Publication Date: Jun. 27, 2000.).

Mills et al., "Fractional Quantum Energy Levels of Hydrogen," Fusion Technology, vol. 28, No. 4, Nov. 1995, pp. 1697-1719. (Internet Publication Date: Nov. 1, 2001.).

Mills et al., "Dihydrino Molecule Identification," Fusion Technology, vol. 25, 103-119 (Jan. 1994). (Internet Publication Date: Apr. 11, 2001.).

Mills Technologies. "1KW Heat Exchanger System." *Thermacore, Inc.*, Oct. 11, 1991, pp. 1-6.

Mills Technologies. "1KVV Heat Exchanger System." *Thermacore, Inc.*, Apr. 17, 1992, pp. 1-6.

Mills, "Classical Quantum Mechanics." Physica Scripta, submitted.

Mills, "The Grand Unified Theory of Classical Quantum Mechanics," (2001), Distributed by Amazon.Com.

Mills, et. al., "Excess heat production by electrolysis of an aquous potassium carbonate electrolyte and the implications for cold fusion," Fusion Technol. vol. 20, pp. 65-81 (1991).

Mills,. "Author's response 'A possible trick of Hydride atom'," *International Journal of Hydrogen Energy*, vol. 26, 2001, p. 1225.

Mills, "Blacklight Power Technology: A New Clean Energy Source with the Potential for Direct Conversion to Electricity," *International Conference on Global Warming and Energy Policy*, Ft. Lauderdale, Florida, Nov. 26-28, 2000. Internet Publication Jan. 19, 2001.

Mills, "Hydro catalysis Power Technology," *Statement of Dr. Randell L. Mills*, May 1993.

Mills, "The Grand Unified Theory of Classical Quantum Mechanics," pp. 1-9.

Mills, "Unification of Spacetime, the Forces, Matter, Energy, Hydro catalysis Power Corporation," 1992, pp. 53-84.

Mills, "Author's response to 'Hydrino atom: novel chemistry or invalid physics'," *International Journal of Hydrogen Energy*, vol. 26, 2001, pp. 1233.

Mills,"Author's response to 'Hydrino theory-a proposed amendment'," *International Journal of Hydrogen Energy*, vol. 26, 2001, pp. 1229-1231.

Mills."Power Spectrum of the Cosmic Microwave Background" *BlackLight Power, Inc.* 2001.

Mills, "The Grand Unified Theory of Classical Quantum Mechanics," pp. 13-14, BlackLight Power, Inc., pp. 433-440, 2001.

Letter from Shelby T. Brewer to the Honorable James E. Rogan, Dec. 21, 2001 and PTO response from Jason C. Roe, Apr. 24, 2002 (see Attachment A).

Park, "Patent Nonsense, Court Denies Blacklight Power Appeal," What's New, Sep. 6, 2002, www.aps.org.WN/WNO2/wn090602.html (see Attachment C).

Randi, "Houdini and the Rabbi, The Patent Office Again, A Perpetual Motion/Emotion Car Breaks Down . . . ," Swift, Sep. 20, 2002, www.randi.or/jir/092002.html (see Attachment C).

Voss, "New Physics' Finds a Haven At the Patent Office," Science, vol. 284, pp. 1252-1254, May 21, 1999 (see Attachment D).

PTO Memorandum For All Employees: Media Contact Policy from Acting Assistant Secretary of Commerce and Acting Commissioner of patents and Trademarks, Jun. 22, 1999.

Letter from Jeffrey S. Melcher to Ms. Esther Kepplinger, Feb. 28, 2000 (see Attachment G).

Internet Discussion Forum, "Two Brand New Papers out at BLP's "What's New" page," message No. 7191 on Hydrino Study Group, http://groups.yahoo.com/group/hyrino/message/7191, Sep. 27, 2003 (see Attachment H).

Internet Discussion Forum, "Even Skeptics can lose Objectivity," message No. 7410 on Hydrino Study Group, http://groups.yahoo.com/group/hyrino/message/7410, Oct. 27, 2003 (see Attachment H).

Internet Discussion Forum, "Two Competing Views of Reality Engage in a Battle for Total Control of O our Physics Paradigm," Hydrino Study Group, http://www.hydrino.org (see Attachment H).

Internet Discussion Forum, "Zimmerman's APS Centennial Meeting Talk," Transcript from Tom Stolper, Nov. 10, 2003 (see Attachment H).

Internet Discussion Forum, "Zimmerman's APS Centennial Meeting Talk," Transcript from Peter Zimmerman and Tom Stolper, Oct. 29, 2003 (see Attachment H).

Internet Discussion Forum, "Zimmerman's APS Centennial Meeting Talk," Transcript from Tom Stolper, Oct. 28, 2003 (see Attachment H).

Internet Discussion Forum, "HSG: Even skeptics can lose objectivity," Transcript from Steve Menton, Oct. 26, 2003 (see Attachment H).

Internet Discussion Forum, "HSG: Zimmerman's Insincere Questions," Transcript from Peter Zimmerman and Steve Menton, Sep. 25, 2003 (see Attachment H).

Internet Discussion Forum, "Re: Re: Zero Electrostatic Self-Interaction Justified," Transcript from Peter Zimmerman, May 22, 2003 http:groups.yahoo.com/group/hydrino/message/6052 (see Attachment H).

Internet Discussion Forum, "HSG: Re: Bool Review by Dr. John Farrell," Transcript from Peter Zimmerman, Feb. 23, 2004 (see Attachment H).

"Regarding PZ's Departing Post," includes many public posts on hydrino study group. pp. 1-75 (see Attachment I).

Park, "Perpetual Motion: Still Going Around," Special to the Washington Post, Jan. 12, 2000, p. H03 (see Attachment J).

Letter from Jeffrey S. Melcher to Ms. Esther Kepplinger with Attachments A-E, Jan. 19, 2001(see Attachment K).

Platt, "Testing the Current," The Washington Post, Jun. 25, 2000, p. X05 (see Attachment M).

USPTO Communication re Interview scheduled for Feb. 21, 2003, Feb. 12, 2001(see Attachment N).

Letter from Senator Ron Wyden to the Honorable Todd Q. Dickinson with attachments, Apr. 5, 2000 (see Attachment 0).

Letter from Senator Robert G. Torricelli to Nicholas P. Godici with attachments, Jul. 20, 2001(see Attachment O).

Letter from Senator Jon S. Corzine to The Honorable Todd Q. Dickinson with attachments, Aug. 2, 2001 (see Attachment O).

Letter from Senator Max Cleland to Ms. Jane Cooksey with attachments, Mar. 24, 2000 (see Attachment O).

Letter from Senators Max Cleland and Ron Wyden to Chairman Patrick Leahy, Dec. 20, 2001 (see Attachment O).

Letter from Senators Max Cleland and Ron Wyden to The Honorable Donald L. Evans, Dec. 20, 2001 (see Attachment O).

Letter from Senators Jon S. Corzine and Robert G. Torricelli to The Honorable Donald L. Evans, Dec. 21, 2001 (see Attachment O).

Email re Interview Summary from Jeffrey Simenauer to Ted Liu, Feb. 13, 2003 (see Attachment P).

"APS E-Board Pases Resolution on Perpetual Motion Machines," APS News Online, Aug./Sep. 2002, http://www.eps.org/aps/apsnews/0802/080212.html (see Attachment Q).

Letter from Elizabeth Barlow to John Allen, Mar. 17, 2004 (see Attachment R).

Letters from John Allen to Office of Counsel, US Department of Commerce with attachments, May 12, 2003, Jun. 7, 2003, and Mar. 10, 2004 (see Attachment R).

Brookhaven National Laboratory letter dated Oct. 16, 1991 to Dr. Walter Polansky, U.S. Department of Energy.

"Charles Evans & Associates—Time of Flight-Secondary Ion Mass Spectroscopy Report".

Charles Evans & Associates—Report re "XPS/ESCA Results," Nov. 3, 1994.

"Rule 132 Declaration of Dr. Randell L. Mills," dated Oct. 3, 2007.

"Second Declaration of Randell L. Mills, M.D. under 37 C.F.R. 1.132," dated Mar. 13, 1998.

"Declaration of Dr. Jonathan Phillips," dated Jul. 20, 2000.

"Declaration of Michael G. Jacox," dated Jul. 25, 2000.

"Declaration of Dr. Bala Dhandapani," dated Aug. 14, 2000.

"Declaration of Dr. Gary L. Turner," dated May 18, 2000.

"Declaration of Robert M. Shaubach and Nelson J. Gernert Under 37 C.F.R. 1.132," dated Mar. 10, 1998.

Declaration of Robert M. Shaubach and Nelson J. Gernert, dated Aug. 24, 1992.

Declaration of Sergei B. Nesterov and Alexei P. Kryukov, dated Feb. 26, 1993.

Idaho National Engineering Laboratory, "Experimental Verification".

Mills Statement Before the Subcommittee on Energy, May 5, 1993.

Phillips et al., "Report on Calorimetric Investigations of Gas-Phase Catalyzed Hydrino Formation," Final Report for period Oct.-Dec. 1996.

Phillips et al., "Calorimetric Study of the Gas Phase Production of Hydrinos," Report to HydroCatalysis Power Corporation, Oct. 1996.

* cited by examiner

View Along the Positive Z Axis

The magnetic field is constant inside of the orbitsphere

METHOD AND SYSTEM OF COMPUTING AND RENDERING THE NATURE OF THE EXCITED ELECTRONIC STATES OF ATOMS AND ATOMIC IONS

I. INTRODUCTION

1. Field of the Invention

This invention relates to a method and system of physically solving the charge, mass, and current density functions of excited states of atoms and atomic ions and computing and rendering the nature of these species using the solutions. The results can be displayed on visual or graphical media. The displayed information is useful to anticipate reactivity and physical properties. The insight into the nature of excited-state electrons can permit the solution and display of other excited-state atoms and ions and provide utility to anticipate their reactivity, physical properties, and spectral absorption and emission.

Rather than using postulated unverifiable theories that treat atomic particles as if they were not real, physical laws are now applied to atoms and ions. In an attempt to provide some physical insight into atomic problems and starting with the same essential physics as Bohr of the e⁻ moving in the Coulombic field of the proton with a true wave equation as opposed to the diffusion equation of Schrödinger, a classical approach is explored which yields a model which is remarkably accurate and provides insight into physics on the atomic level. The proverbial view deeply seated in the wave-particle duality notion that there is no large-scale physical counterpart to the nature of the electron is shown not to be correct. Physical laws and intuition may be restored when dealing with the wave equation and quantum atomic problems.

Specifically, a theory of classical quantum mechanics (CQM) was derived from first principles as reported previously [reference Nos. 1-7] that successfully applies physical laws to the solution of atomic problems that has its basis in a breakthrough in the understanding of the stability of the bound electron to radiation. Rather than using the postulated Schrödinger boundary condition: "$\Psi \to 0$ as $r \to \infty$", which leads to a purely mathematical model of the electron, the constraint is based on experimental observation. Using Maxwell's equations, the classical wave equation is solved with the constraint that the bound n=1-state electron cannot radiate energy. Although it is well known that an accelerated point particle radiates, an extended distribution modeled as a superposition of accelerating charges does not have to radiate. A simple invariant physical model arises naturally wherein the predicted results are extremely straightforward and internally consistent requiring minimal math as in the case of the most famous equations of Newton, Maxwell, Einstein, de Broglie, and Planck on which the model is based. No new physics is needed; only the known physical laws based on direct observation are used. The solution of the excited states of one-electron atoms is given in R. Mills, *The Grand Unified Theory of Classical Quantum Mechanics*, January 2005 Edition, BlackLight Power, Inc., Cranbury, N.J., ("'05 Mills GUT") which is herein incorporated by reference. This Invention further comprises the accurate solution of the helium-atom excited states which provides a physical algorithm to solve the excited states of other multi-electron atoms.

2. Background of the Invention

2A. Classical Quantum Theory of the Atom Based on Maxwell's Equations

The old view that the electron is a zero or one-dimensional point in an all-space probability wave function $\Psi(x)$ is not taken for granted. The theory of classical quantum mechanics (CQM), derived from first principles, must successfully and consistently apply physical laws on all scales [1-7]. Stability to radiation was ignored by all past atomic models. Historically, the point at which QM broke with classical laws can be traced to the issue of nonradiation of the one electron atom. Bohr just postulated orbits stable to radiation with the further postulate that the bound electron of the hydrogen atom does not obey Maxwell's equations—rather it obeys different physics [1-10]. Later physics was replaced by "pure mathematics" based on the notion of the inexplicable wave-particle duality nature of electrons which lead to the Schrödinger equation wherein the consequences of radiation predicted by Maxwell's equations were ignored. Ironically, Bohr, Schrödinger, and Dirac used the Coulomb potential, and Dirac used the vector potential of Maxwell's equations. But, all ignored electrodynamics and the corresponding radiative consequences. Dirac originally attempted to solve the bound electron physically with stability with respect to radiation according to Maxwell's equations with the further constraints that it was relativistically invariant and gave rise to electron spin [11]. He and many founders of QM such as Sommerfeld, Bohm, and Weinstein wrongly pursued a planetary model, were unsuccessful, and resorted to the current mathematical-probability-wave model that has many problems [10, 11-14]. Consequently, Feynman for example, attempted to use first principles including Maxwell's equations to discover new physics to replace quantum mechanics [15].

Physical laws may indeed be the root of the observations thought to be "purely quantum mechanical", and it was a mistake to make the assumption that Maxwell's electrodynamic equations must be rejected at the atomic level. Thus, in the present approach, the classical wave equation is solved with the constraint that a bound n=1-state electron cannot radiate energy.

Herein, derivations consider the electrodynamic effects of moving charges as well as the Coulomb potential, and the search is for a solution representative of the electron wherein there is acceleration of charge motion without radiation. The mathematical formulation for zero radiation based on Maxwell's equations follows from a derivation by Haus [16]. The function that describes the motion of the electron must not possess spacetime Fourier components that are synchronous with waves traveling at the speed of light. Similarly, nonradiation is demonstrated based on the electron's electromagnetic fields and the Poynting power vector.

It was shown previously [1-7] that CQM gives closed form solutions for the atom including the stability of the n=1 state and the instability of the excited states, the equation of the photon and electron in excited states, the equation of the free electron, and photon which predict the wave particle duality behavior of particles and light. The current and charge density functions of the electron may be directly physically interpreted. For example, spin angular momentum results from the motion of negatively charged mass moving systematically, and the equation for angular momentum, r×p, can be applied directly to the wave function (a current density function) that describes the electron. The magnetic moment of a Bohr magneton, Stern Gerlach experiment, g factor, Lamb shift, resonant line width and shape, selection rules, correspondence principle, wave particle duality, excited states, reduced mass, rotational energies, and momenta, orbital and spin splitting, spin-orbital coupling, Knight shift, and spin-nuclear coupling, and elastic electron scattering from helium atoms, are derived in closed-form equations based on Maxwell's equations. The calculations agree with experimental observations.

The Schrödinger equation gives a vague and fluid model of the electron. Schrödinger interpreted $e\Psi^*(x)\Psi(x)$ as the charge-density or the amount of charge between x and x+dx ($\Psi^*$ is the complex conjugate of $\Psi$). Presumably, then, he pictured the electron to be spread over large regions of space. After Schrödinger's interpretation, Max Born, who was working with scattering theory, found that this interpretation led to inconsistencies, and he replaced the Schrödinger interpretation with the probability of finding the electron between x and x+dx as $$\int \Psi(x)\Psi^*(x)dx \tag{1}$$

Born's interpretation is generally accepted. Nonetheless, interpretation of the wave function is a never-ending source of confusion and conflict. Many scientists have solved this problem by conveniently adopting the Schrödinger interpretation for some problems and the Born interpretation for others. This duality allows the electron to be everywhere at one time-yet have no volume. Alternatively, the electron can be viewed as a discrete particle that moves here and there (from r=0 to r=∞), and $\Psi\Psi^*$ gives the time average of this motion.

In contrast to the failure of the Bohr theory and the nonphysical, adjustable-parameter approach of quantum mechanics, multielectron atoms [1, 5] and the nature of the chemical bond [1, 4] are given by exact closed-form solutions containing fundamental constants only. Using the nonradiative wave equation solutions that describe the bound electron having conserved momentum and energy, the radii are determined from the force balance of the electric, magnetic, and centrifugal forces that corresponds to the minimum of energy of the system. The ionization energies are then given by the electric and magnetic energies at these radii. The spreadsheets to calculate the energies from exact solutions of one through twenty-electron atoms are given in '05 Mills GUT [1] and are available from the internet [17]. For 400 atoms and ions the agreement between the predicted and experimental results is remarkable.

The background theory of classical quantum mechanics (CQM) for the physical solutions of atoms and atomic ions is disclosed in R. Mills, *The Grand Unified Theory of Classical Quantum Mechanics*, January 2000 Edition, BlackLight Power, Inc., Cranbury, N.J., ("'00 Mills GUT"), provided by BlackLight Power, Inc., 493 Old Trenton Road, Cranbury, N.J., 08512; R. Mills, *The Grand Unified Theory of Classical Quantum Mechanics*, September 2001 Edition, BlackLight Power, Inc., Cranbury, N.J., Distributed by Amazon.com ("'01 Mills GUT"), provided by BlackLight Power, Inc., 493 Old Trenton Road, Cranbury, N.J., 08512; R. Mills, *The Grand Unified Theory of Classical Quantum Mechanics*, July 2004 Edition, BlackLight Power, Inc., Cranbury, N.J., ("'04 Mills GUT"), provided by BlackLight Power, Inc., 493 Old Trenton Road, Cranbury, N.J., 08512; R. Mills, *The Grand Unified Theory of Classical Quantum Mechanics*, January 2005 Edition, BlackLight Power, Inc., Cranbury, N.J., ("'05 Mills GUT"), provided by BlackLight Power, Inc., 493 Old Trenton Road, Cranbury, N.J., 08512 (posted at www.blacklightpower.com); in prior PCT applications PCT/US02/35872; PCT/US02/06945; PCT/US02/06955; PCT/US01/09055; PCT/US01/25954; PCT/US00/20820; PCT/US00/20819; PCT/US00/09055; PCT/US99/17171; PCT/US99/17129; PCT/US 98/22822; PCT/US98/14029; PCT/US96/07949; PCT/US94/02219; PCT/US91/08496; PCT/US90/01998; and PCT/JS89/05037 and U.S. Pat. No. 6,024,935; the entire disclosures of which are all incorporated herein by reference; (hereinafter "Mills Prior Publications").

II. SUMMARY OF THE INVENTION

An object of the present invention is to solve the charge (mass) and current-density functions of excited-state atoms and atomic ions from first principles. In an embodiment, the solution for the excited and non-excited state is derived from Maxwell's equations invoking the constraint that the bound electron before excitation does not radiate even though it undergoes acceleration.

Another objective of the present invention is to generate a readout, display, or image of the solutions so that the nature of excited-state atoms and atomic ions can be better understood and potentially applied to predict reactivity and physical and optical properties.

Another objective of the present invention is to apply the methods and systems of solving the nature of excited-state electrons and their rendering to numerical or graphical form to all atoms and atomic ions.

Bound electrons are described by a charge-density (mass-density) function which is the product of a radial delta function ($f(r)=\delta(r-r_n)$), two angular functions (spherical harmonic functions), and a time harmonic function. Thus, a bound electron is a dynamic "bubble-like" charge-density function. The two-dimensional spherical surface called an electron orbitsphere shown in FIG. 1 can exist in a bound state at only specified distances from the nucleus. More explicitly, the orbitsphere comprises a two-dimensional spherical shell of moving charge. The current pattern of the orbitsphere that gives rise to the phenomenon corresponding to the spin quantum number comprises an infinite series of correlated orthogonal great circle current loops. As given in the Orbitsphere Equation of Motion for l=0 section of '05 Mills GUT [1], the current pattern (shown in FIG. 2) is generated over the surface by two orthogonal sets of an infinite series of nested rotations of two orthogonal great circle current loops where the coordinate axes rotate with the two orthogonal great circles. Each infinitesimal rotation of the infinite series is about the new x-axis and new y-axis which results from the preceding such rotation. For each of the two sets of nested rotations, the angular sum of the rotations about each rotating x-axis and y-axis totals $\sqrt{2}\pi$ radians. The spin function of the electron corresponds to the nonradiative n=1, l=0 state which is well known as an s state or orbital. (See FIG. 1 for the charge function and FIG. 2 for the current function.) In cases of orbitals of excited states with the l quantum number not equal to zero and which are not constant as given by Eq. (1.64) of Ref. [1], the constant spin function is modulated by a time and spherical harmonic function as given by Eq. (1.65) of Ref. [1] and shown in FIG. 3. The modulation or traveling charge-density wave corresponds to an orbital angular momentum in addition to a spin angular momentum. These states are typically referred to as p, d, f, etc. orbitals.

Each orbitsphere is a spherical shell of negative charge (total charge=−e) of zero thickness at a distance $r_n$ from the nucleus (charge=+Ze). It is well known that the field of a spherical shell of charge is zero inside the shell and that of a point charge at the origin outside the shell [1] (See FIG. 1.12 of Ref. [1]). The field of each electron can be treated as that corresponding to a −e charge at the origin with $$E = \frac{-e}{4\pi\varepsilon_o r^2}$$

for $r>r_n$ and $E=0$ for $r<r_n$ where $r_n$ is the radius of the electron orbitsphere. Thus, as shown in the Two-Electron Atom section of '05 Mills GUT [1], the central electric fields due to the helium nucleus are $$E = \frac{2e}{4\pi\varepsilon_o r^2}$$

and $$E = \frac{e}{4\pi\varepsilon_o r^2}$$

for $r<r_1$ and $r_1<r<r_2$, respectively. In the ground state of the helium atom, both electrons are at $r_1=r_2=0.567a_o$. When a photon is absorbed, one of the initially indistinguishable electrons called electron 1 moves to a smaller radius, and the other called electron 2 moves to a greater radius. In the limiting case of the absorption of an ionizing photon, electron 1 moves to the radius of the helium ion, $r_1=0.5a_o$, and electron 2 moves to a continuum radius, $r_2=\infty$. When a photon is absorbed by the ground state helium atom it generates an effective charge, $Z_{P-eff}$, within the second orbitsphere such that the electrons move in opposite radial directions while conserving energy and angular momentum. We can determine $Z_{P-eff}$ of the "trapped photon" electric field by requiring that the resonance condition is met for photons of discrete energy, frequency, and wavelength for electron excitation in an electromagnetic potential energy well.

In contrast to the shortcomings of quantum mechanics, with classical quantum mechanics (CQM), all excited states of the helium atom can be exactly solved in closed form. Photon absorption occurs by an excitation of a Maxwellian multipole cavity mode wherein the excitation is quantized according to the quantized energy and angular momentum of the photon given by $\hbar w$ and $\hbar$, respectively. The photon quantization causes the central electric-field corresponding the superimposed fields of the nucleus, electron 1, and the photon to be quantized and of magnitude of a reciprocal integer times that of the proton. This field and the phase-matched angular dependence of the trapped photon and excited-state electron as well as the spin orientation of the excited-state electron determine the central forces. The radii of electron 2 are determined from the force balance of the electric, magnetic, and centrifugal forces that corresponds to the minimum of energy of the system. Since the magnetic energies are relatively insignificant, in one embodiment, the excited state energies are then given by one physical term in each case, the Coulombic energy at the calculated radius. In additional embodiments, additional small terms may refine the solutions. Given the typical average relative difference is about 5 significant figures which is within the error of the experimental data, this result is remarkable and strongly confirms that the physical CQM solution of helium is correct.

The presented exact physical solutions for the excited states of the helium atom can be applied to other atoms and ions to solve for their excited states. These solution can be used to predict the properties of elements and ions and engineer compositions of matter in a manner which is not possible using quantum mechanics. It also for the prediction of the spectral absorption and emission. This in term can be used to develop new light filters or absorbers as well as new light sources such as lasers, lamps, and spectral standards.

In an embodiment., the physical, Maxwellian solutions for the dimensions and energies of excited-state atom and atomic ions are processed with a processing means to produce an output. Embodiments of the system for performing computing and rendering of the nature of the excited-state atomic and atomic-ionic electrons using the physical solutions may comprise a general purpose computer. Such a general purpose computer may have any number of basic configurations. For example, such a general purpose computer may comprise a central processing unit (CPU), one or more specialized processors, system memory, a mass storage device such as a magnetic disk, an optical disk, or other storage device, an input means such as a keyboard or mouse, a display device, and a printer or other output device. A system implementing the present invention can also comprise a special purpose computer or other hardware system and all should be included within its scope.

III. BRIEF DESCRIPTION OF THE DRAWINGS

FIG. 1 shows the orbitsphere in accordance with the present invention that is a two dimensional spherical shell of zero thickness with the Bohr radius of the hydrogen atom, $r=a_H$.

FIG. 2 shows the current pattern of the orbitsphere in accordance with the present invention from the perspective of looking along the z-axis. The current and charge density are confined to two dimensions at $r_n=nr_1$. The corresponding charge density function is uniform.

IV. DETAILED DESCRIPTION OF THE INVENTION

Figure 1:
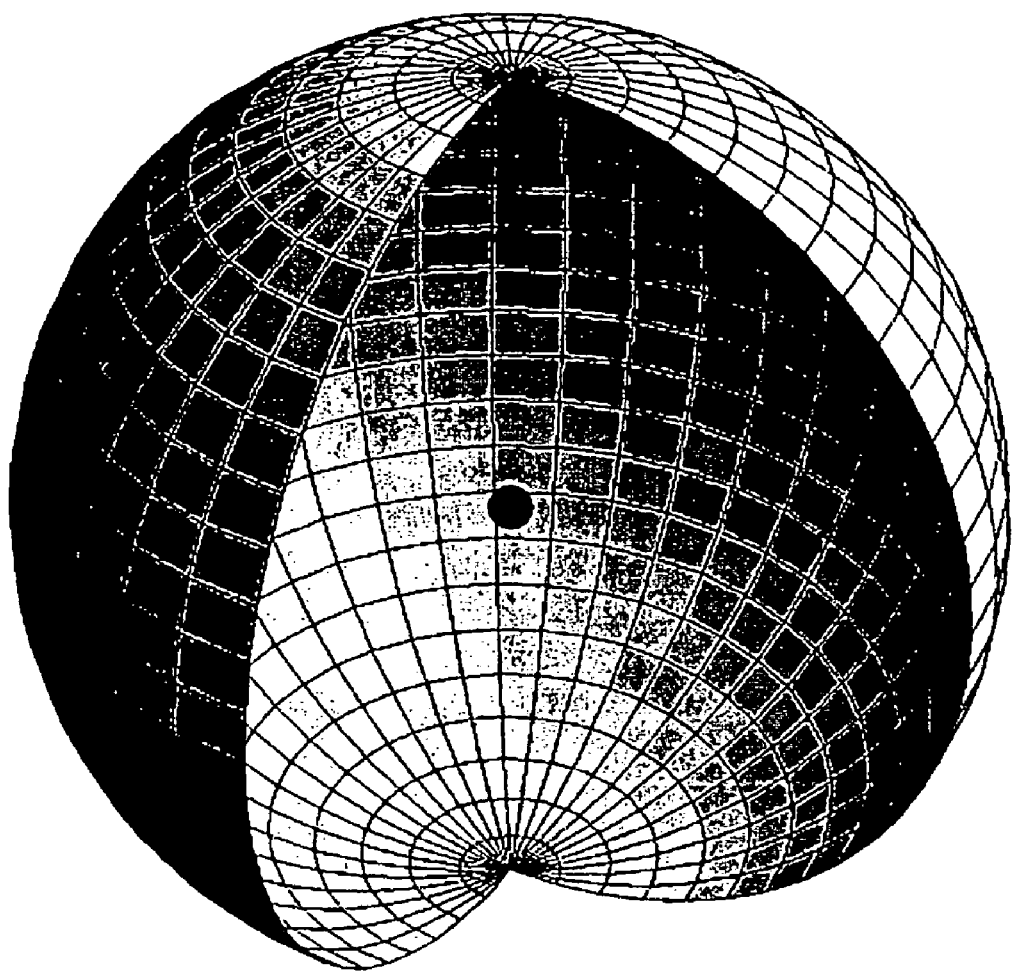

The following preferred embodiments of the invention disclose numerous calculations which are merely intended as illustrative examples. Based on the detailed written description, one skilled in the art would easily be able to practice this Invention within other like calculations to produce the desired result without undue effort.

1. One-Electron Atoms

1. One-Electron Atoms

One-electron atoms include the hydrogen atom, $He^+$, $Li^{2+}$, $Be^{3+}$, and so on. The mass-energy and angular momentum of the electron are constant; this requires that the equation of motion of the electron be temporally and spatially harmonic.

Thus, the classical wave equation applies and $$\left[\nabla^2 - \frac{1}{v^2}\frac{\partial^2}{\partial t^2}\right]\rho(r, \theta, \phi, t) = 0 \qquad (2)$$

where $\rho(r,\theta,\phi,t)$ is the time dependent charge density function of the electron in time and space. In general, the wave equation has an infinite number of solutions. To arrive at the solution which represents the electron, a suitable boundary condition must be imposed. It is well known from experiments that each single atomic electron of a given isotope radiates to the same stable state. Thus, the physical boundary condition of nonradiation of the bound electron was imposed on the solution of the wave equation for the time dependent charge density function of the electron [1-3, 5]. The condition for radiation by a moving point charge given by Haus [16] is that its spacetime Fourier transform does possess components that are synchronous with waves traveling at the speed of light. Conversely, it is proposed that the condition for nonradiation by an ensemble of moving point charges that comprises a current density function is For non-radiative states, the current-density function must NOT possess spacetime Fourier components that are synchronous with waves traveling at the speed of light.

The time, radial, and angular solutions of the wave equation are separable. The motion is time harmonic with frequency $\omega_n$. A constant angular function is a solution to the wave equation. Solutions of the Schrödinger wave equation comprising a radial function radiate according to Maxwell's equation as shown previously by application of Haus' condition [1]. In fact, it was found that any function which permitted radial motion gave rise to radiation. A radial function which does satisfy the boundary condition is a radial delta function $$f(r) = \frac{1}{r^2}\delta(r - r_n) \qquad (3)$$

This function defines a constant charge density on a spherical shell where $r_n = n r_1$ wherein n is an integer in an excited state, and Eq. (2) becomes the two-dimensional wave equation plus time with separable time and angular functions. Given time harmonic motion and a radial delta function, the relationship between an allowed radius and the electron wavelength is given by $$2\pi r_n = \lambda_n \qquad (4)$$

where the integer subscript n here and in Eq. (3) is determined during photon absorption as given in the Excited States of the One-Electron Atom (Quantization) section of Ref. [1]. Using the observed de Broglie relationship for the electron mass where the coordinates are spherical, $$\lambda_n = \frac{h}{p_n} = \frac{h}{m_e v_n} \qquad (5)$$

and the magnitude of the velocity for every point on the orbitsphere is $$v_n = \frac{\hbar}{m_e r_n} \qquad (6)$$

The sum of the $|L_i|$, the magnitude of the angular momentum of each infinitesimal point of the orbitsphere of mass $m_i$, must be constant. The constant is $\hbar$.

$$\sum |L_i| = \sum |r \times m_i v| = m_e r_n \frac{\hbar}{m_e r_n} = \hbar \qquad (7)$$

Figure 2:
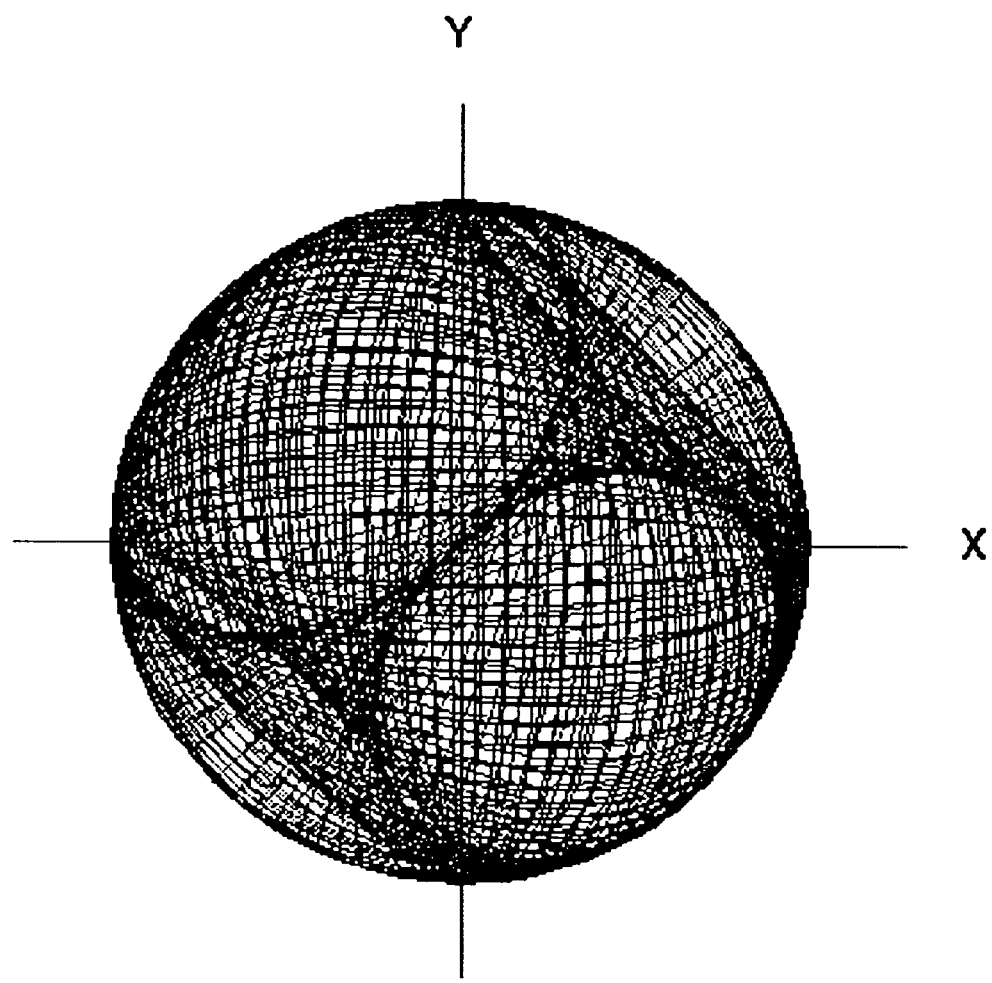

Thus, an electron is a spinning, two-dimensional spherical surface (zero thickness), called an electron orbitsphere shown in FIG. 1, that can exist in a bound state at only specified distances from the nucleus determined by an energy minimum. The corresponding current function shown in FIG. 2 which gives rise to the phenomenon of spin is derived in the Spin Function section. (See the Orbitsphere Equation of Motion for l=0 of Ref. [1] at Chp. 1.)

Nonconstant functions are also solutions for the angular functions. To be a harmonic solution of the wave equation in spherical coordinates, these angular functions must be spherical harmonic functions [18]. A zero of the spacetime Fourier transform of the product function of two spherical harmonic angular functions, a time harmonic function, and an unknown radial function is sought. The solution for the radial function which satisfies the boundary condition is also a delta function given by Eq. (3). Thus, bound electrons are described by a charge-density (mass-density) function which is the product of a radial delta function, two angular functions (spherical harmonic functions), and a time harmonic function.

$$\rho(r, \theta, \phi, t) = f(r)A(\theta, \phi, t) = \frac{1}{r^2}\delta(r - r_n)A(\theta, \phi, t); \qquad (8)$$

$$A(\theta, \phi, t) = Y(\theta, \phi)k(t)$$

Figure 3:
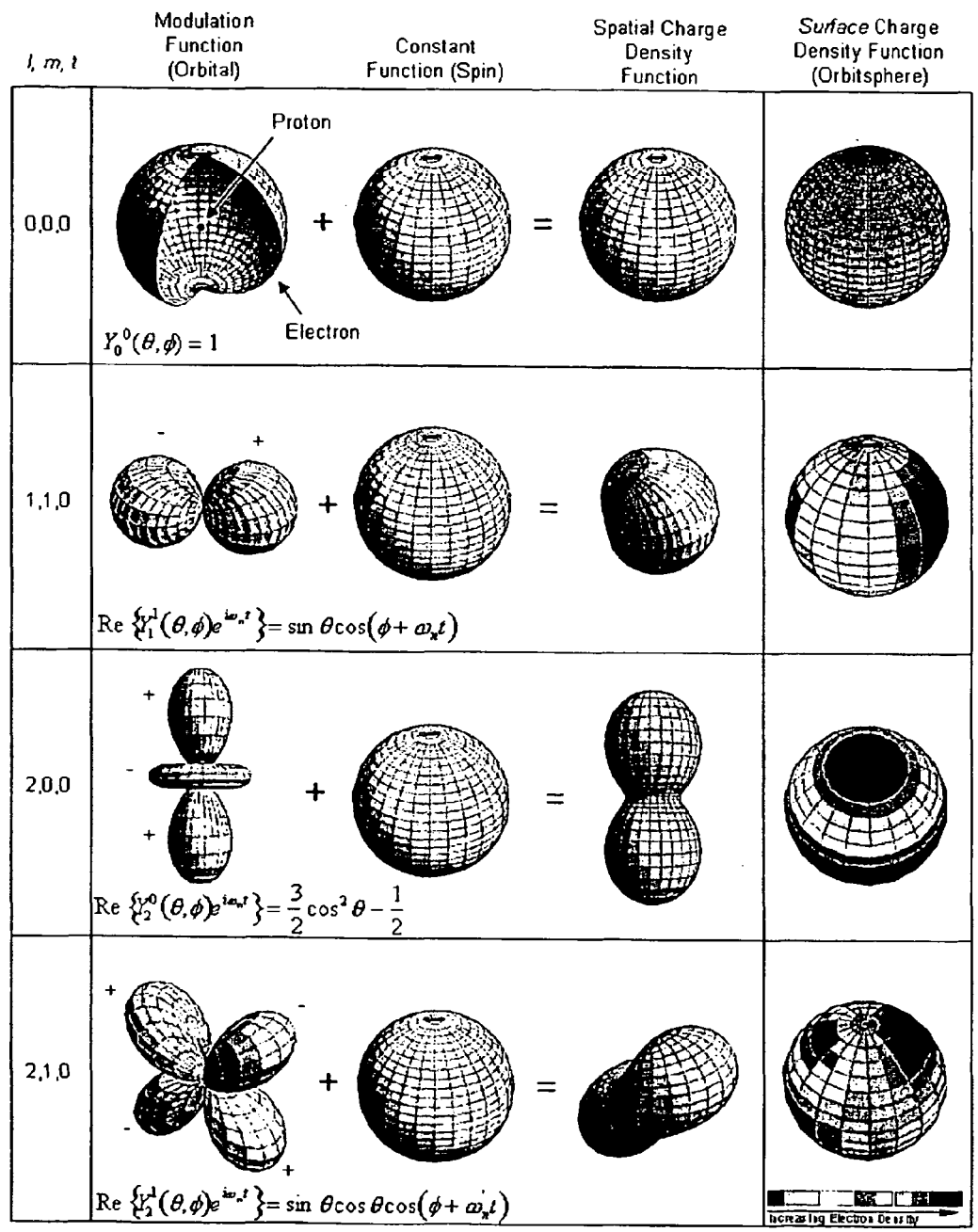
FIG. 3 shows that the orbital function modulates the constant (spin) function (shown for t=0; three-dimensional view).

In these cases, the spherical harmonic functions correspond to a traveling charge density wave confined to the spherical shell which gives rise to the phenomenon of orbital angular momentum. The orbital functions which modulate the constant "spin" function shown graphically in FIG. 3 are given in the Sec. 1.B.

1.A. Spin Function

The orbitsphere spin function comprises a constant charge (current) density function with moving charge confined to a two-dimensional spherical shell. The magnetostatic current pattern of the orbitsphere spin function comprises an infinite series of correlated orthogonal great circle current loops wherein each point charge (current) density element moves time harmonically with constant angular velocity $$\omega_n = \frac{\hbar}{m_e r_n^2} \qquad (9)$$

The uniform current density function $Y_0^0(\phi,\theta)$, the orbitsphere equation of motion of the electron (Eqs. (14-15)), corresponding to the constant charge function of the orbitsphere that gives rise to the spin of the electron is generated from a basis set current-vector field defined as the orbitsphere current-vector field ("orbitsphere-cvf"). This in turn is generated over the surface by two complementary steps of an infinite series of nested rotations of two orthogonal great circle current loops where the coordinate axes rotate with the two orthogonal great circles that serve as a basis set. The algorithm to generate the current density function rotates the great circles and the corresponding x'y'z' coordinates relative to the xyz frame. Each infinitesimal rotation of the infinite series is about the new i'-axis and new j'-axis which results from the preceding such rotation. Each element of the current density function is obtained with each conjugate set of rotations. In Appendix III of Ref. [1], the continuous uniform electron current density function $Y_0^0(\phi,\theta)$ having the same angular momentum components as that of the orbitsphere-cvf is then exactly generated from this orbitsphere-cvf as a basis element by a convolution operator comprising an autocorrelation-type function.

For Step One, the current density elements move counter clockwise on the great circle in the y'z'-plane and move clockwise on the great circle in the x'z'-plane. The great circles are rotated by an infinitesimal angle $\pm \Delta \alpha_i$ (a positive rotation around the x'-axis or a negative rotation about the z'-axis for Steps One and Two, respectively) and then by $\pm \Delta \alpha_j$ (a positive rotation around the new y'-axis or a positive rotation about the new x'-axis for Steps One and Two, respectively). The coordinates of each point on each rotated great circle (x',y',z') is expressed in terms of the first (x,y,z) coordinates by the following transforms where clockwise rotations and motions are defined as positive looking along the corresponding axis:

Step One $$\begin{bmatrix} x \\ y \\ z \end{bmatrix} = \begin{bmatrix} \cos(\Delta\alpha_y) & 0 & -\sin(\Delta\alpha_y) \\ 0 & 1 & 0 \\ \sin(\Delta\alpha_y) & 0 & \cos(\Delta\alpha_y) \end{bmatrix} \begin{bmatrix} 1 & 0 & 0 \\ 0 & \cos(\Delta\alpha_x) & \sin(\Delta\alpha_x) \\ 0 & -\sin(\Delta\alpha_x) & \cos(\Delta\alpha_x) \end{bmatrix} \begin{bmatrix} x' \\ y' \\ z' \end{bmatrix} \quad (10)$$

$$\begin{bmatrix} x \\ y \\ z \end{bmatrix} = \begin{bmatrix} \cos(\Delta\alpha_y) & \sin(\Delta\alpha_y)\sin(\Delta\alpha_x) & -\sin(\Delta\alpha_y)\cos(\Delta\alpha_x) \\ 0 & \cos(\Delta\alpha_x) & \sin(\Delta\alpha_x) \\ \sin(\Delta\alpha_y) & -\cos(\Delta\alpha_y)\sin(\Delta\alpha_x) & \cos(\Delta\alpha_y)\cos(\Delta\alpha_x) \end{bmatrix} \begin{bmatrix} x' \\ y' \\ z' \end{bmatrix}$$

Step Two $$\begin{bmatrix} x \\ y \\ z \end{bmatrix} = \begin{bmatrix} 1 & 0 & 0 \\ 0 & \cos(\Delta\alpha_x) & \sin(\Delta\alpha_x) \\ 0 & -\sin(\Delta\alpha_x) & \cos(\Delta\alpha_x) \end{bmatrix} \begin{bmatrix} \cos(\Delta\alpha_z) & \sin(\Delta\alpha_z) & 0 \\ -\sin(\Delta\alpha_z) & \cos(\Delta\alpha_z) & 0 \\ 0 & 0 & 1 \end{bmatrix} \begin{bmatrix} x' \\ y' \\ z' \end{bmatrix} \quad (11)$$

$$\begin{bmatrix} x \\ y \\ z \end{bmatrix} = \begin{bmatrix} \cos(\Delta\alpha_z) & \sin(\Delta\alpha_z) & 0 \\ -\cos(\Delta\alpha_x)\sin(\Delta\alpha_z) & \cos(\Delta\alpha_x)\cos(\Delta\alpha_z) & \sin(\Delta\alpha_x) \\ \sin(\Delta\alpha_x)\sin(\Delta\alpha_z) & -\sin(\Delta\alpha_x)\cos(\Delta\alpha_z) & \cos(\Delta\alpha_x) \end{bmatrix} \begin{bmatrix} x' \\ y' \\ z' \end{bmatrix}$$

where the angular sum is $\lim\limits_{\Delta\alpha \to 0} \sum\limits_{n=1}^{\frac{\frac{\sqrt{2}}{2}\pi}{|\Delta\alpha_{i',j'}|}} |\Delta\alpha_{i',j'}| = \frac{\sqrt{2}}{2}\pi.$ The orbitsphere-cvf is given by n reiterations of Eqs. (10) and (11) for each point on each of the two orthogonal great circles during each of Steps One and Two. The output given by the non-primed coordinates is the input of the next iteration corresponding to each successive nested rotation by the infinitesimal angle $\pm \Delta \alpha_i$ or $\pm \Delta \alpha_j$ where the magnitude of the angular sum of the n rotations about each of the i'-axis and the j'-axis is $$\frac{\sqrt{2}}{2}\pi.$$

Half of the orbitsphere-cvf is generated during each of Steps One and Two.

Following Step Two, in order to match the boundary condition that the magnitude of the velocity at any given point on the surface is given by Eq. (6), the output half of the orbitsphere-cvf is rotated clockwise by an angle of $$\frac{\pi}{4}$$

about the z-axis. Using Eq. (11) with $$\Delta\alpha_z = \frac{\pi}{4}$$

and $\Delta\alpha_x=0$ gives the rotation. Then, the one half of the orbitsphere-cvf generated from Step One is superimposed with the complementary half obtained from Step Two following its rotation about the z-axis of $$\frac{\pi}{4}$$

to give the basis function to generate $Y_0^0(\phi,\theta)$, the orbitsphere equation of motion of the electron.

The current pattern of the orbitsphere-cvf generated by the nested rotations of the orthogonal great circle current loops is a continuous and total coverage of the spherical surface, but it is shown as a visual representation using 6 degree increments of the infinitesimal angular variable $\pm \Delta \alpha_{i'}$ and $\pm \Delta \alpha_{j'}$ of Eqs. (10) and (11) from the perspective of the z-axis in FIG. 2. In each case, the complete orbitsphere-cvf current pattern corresponds all the orthogonal-great-circle elements which are generated by the rotation of the basis-set according to Eqs. (10) and (11) where $\pm \Delta \alpha_{i'}$ and $\pm \Delta \alpha_{j'}$ approach zero and the summation of the infinitesimal angular rotations of $\pm \Delta \alpha_i$ and $\pm \Delta \alpha_j$ about the successive i'-axes and j'-axes is $$\frac{\sqrt{2}}{2}\pi$$

for each Step. The current pattern gives rise to the phenomenon corresponding to the spin quantum number. The details of the derivation of the spin function are given in Ref. [3] and Chp. 1 of Ref. [1].

The resultant angular momentum projections of $$L_{xy} = \frac{\hbar}{4} \text{ and } L_z = \frac{\hbar}{2}$$

meet the boundary condition for the unique current having an angular velocity magnitude at each point on the surface given by Eq. (6) and give rise to the Stern Gerlach experiment as shown in Ref. [1]. The further constraint that the current density is uniform such that the charge density is uniform, corresponding to an equipotential, minimum energy surface is satisfied by using the orbitsphere-cvf as a basis element to generate $Y_0^0(\phi,\theta)$ using a convolution operator comprising an autocorrelation-type function as given in Appendix III of Ref. [1]. The operator comprises the convolution of each great circle current loop of the orbitsphere-cvf designated as the primary orbitsphere-cvf with a second orbitsphere-cvf designated as the secondary orbitsphere-cvf wherein the convolved secondary elements are matched for orientation, angular momentum, and phase to those of the primary. The resulting exact uniform current distribution obtained from the convolution has the same angular momentum distribution, resultant, $L_R$, and components of $$L_{xy} = \frac{\hbar}{4} \text{ and } L_z = \frac{\hbar}{2}$$

as those of the orbitsphere-cvf used as a primary basis element.

1.B. Angular Functions

The time, radial, and angular solutions of the wave equation are separable. Also based on the radial solution, the angular charge and current-density functions of the electron, $A(\theta,\phi,t)$, must be a solution of the wave equation in two dimensions (plus time), $$\left[\nabla^2 - \frac{1}{v^2}\frac{\partial^2}{\partial t^2}\right]A(\theta,\phi,t) = 0 \tag{12}$$

where $\rho(r,\theta,\phi,t) = f(r)A(\theta,\phi,t) = \frac{1}{r^2}\delta(r-r_n)$ $A(\theta,\phi,t)$ and $A(\theta,\phi,t)$
$= Y(\theta,\phi)k(t)$ $$\left[\frac{1}{r^2\sin\theta}\frac{\partial}{\partial\theta}\left(\sin\theta\frac{\partial}{\partial\theta}\right)_{r,\phi} + \frac{1}{r^2\sin^2\theta}\left(\frac{\partial^2}{\partial\phi^2}\right)_{r,\theta} - \frac{1}{v^2}\frac{\partial^2}{\partial t^2}\right] \tag{13}$$
$A(\theta,\phi,t) = 0$ where $v$ is the linear velocity of the electron. The charge-density functions including the time-function factor are $\ell = 0$ $$\rho(r,\theta,\phi,t) = \frac{e}{8\pi r^2}[\delta(r-r_n)][Y_0^0(\theta,\phi) + Y_\ell^m(\theta,\phi)] \tag{14}$$

$\ell \neq 0$ $$\rho(r,\theta,\phi,t) = \frac{e}{4\pi r^2}[\delta(r-r_n)][Y_0^0(\theta,\phi) + \text{Re}\{Y_\ell^m(\theta,\phi)e^{i\omega_n t}\}] \tag{15}$$

where $Y_\ell^m(\theta,\phi)$ are the spherical harmonic functions that spin about the z-axis with angular frequency $\omega_n$ with $Y_0^0(\theta,\phi)$ the constant function. $\text{Re}\{Y_\ell^m(\theta,\phi)e^{i\omega j}\}=P_\ell^m(\cos\theta)\cos(m\phi+\omega_n t)$ where to keep the form of the spherical harmonic as a traveling wave about the z-axis, $\omega_n=m\omega_n$.

1.C. Acceleration without Radiation

1.C.a. Special Relativistic Correction to the Electron Radius

Figure 4:
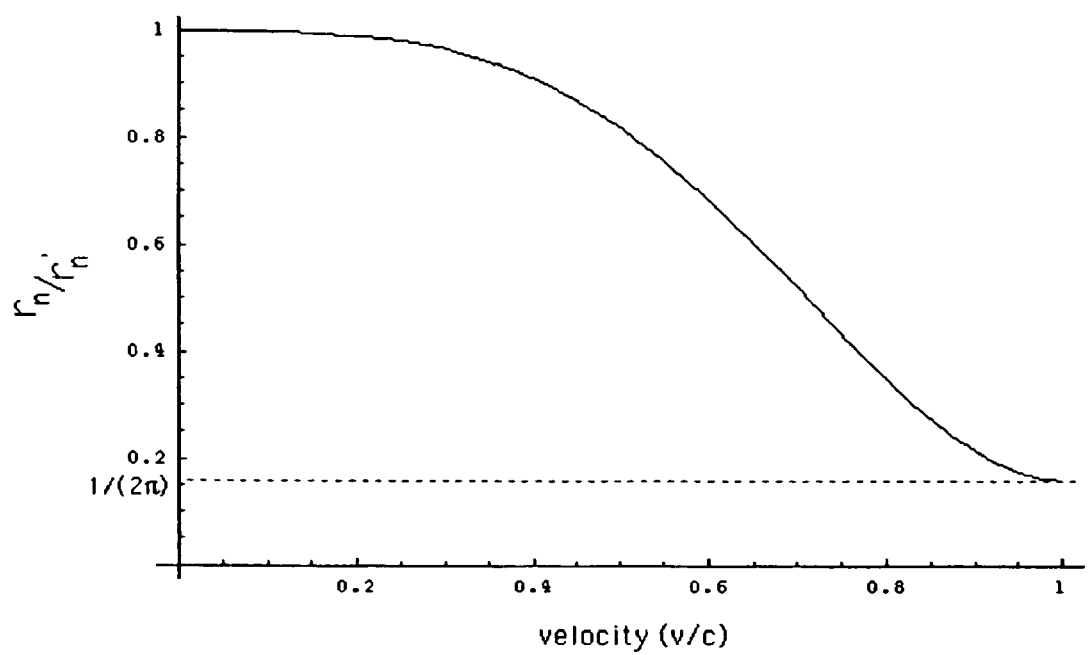
FIG. 4 shows the normalized radius as a function of the velocity due to relativistic contraction.

The relationship between the electron wavelength and its radius is given by Eq. (4) where $\lambda$ is the de Broglie wavelength. For each current density element of the spin function, the distance along each great circle in the direction of instantaneous motion undergoes length contraction and time dilation. Using a phase matching condition, the wavelengths of the electron and laboratory inertial frames are equated, and the corrected radius is given by $$r_n = r_n\left[\sqrt{1-\left(\frac{v}{c}\right)^2}\sin\left[\frac{\pi}{2}\left(1-\left(\frac{v}{c}\right)^2\right)^{3/2}\right] + \frac{1}{2\pi}\cos\left[\frac{\pi}{2}\left(1-\left(\frac{v}{c}\right)^2\right)^{3/2}\right]\right] \tag{16}$$

where the electron velocity is given by Eq. (6). (See Ref. [1] Chp. 1, Special Relativistic Correction to the Ionization Energies section).

$$\frac{e}{m_e}$$

of the electron, the electron angular momentum of $\hbar$, and $\mu_B$ are invariant, but the mass and charge densities increase in the laboratory frame due to the relativistically contracted electron radius. As $v \to c$, $$r/r' \to \frac{1}{2\pi}$$

and $r=\lambda$ as shown in FIG. 4.

1.C.b. Nonradiation Based on the Spacetime Fourier Transform of the Electron Current The Fourier transform of the electron charge density function given by Eq. (8) is a solution of the three-dimensional wave equation in frequency space (k, $\omega$ space) as given in Chp 1, Spacetime Fourier Transform of the Electron Function section of Ref. [1]. Then, the corresponding Fourier transform of the current density function $K(s,\Theta,\Phi,\omega)$ is given by multiplying by the constant angular frequency.

$$K(s,\Theta,\Phi,\omega) = 4\pi\omega_n \frac{\sin(2s_n r_n)}{2s_n r_n} \otimes 2\pi \tag{17}$$

$$\sum_{\upsilon=1}^{\infty} \frac{(-1)^{\upsilon-1}(\pi\sin\Theta)^{2(\upsilon-1)}}{(\upsilon-1)!(\upsilon-1)!} \frac{\Gamma\left(\frac{1}{2}\right)\Gamma\left(\upsilon+\frac{1}{2}\right)}{(\pi\cos\Theta)^{2\upsilon+1}2^{\upsilon+1}} \frac{2\upsilon!}{(\upsilon-1)!}$$

$$s^{-2\upsilon} \otimes 2\pi \sum_{\upsilon=1}^{\infty} \frac{(-1)^{\upsilon-1}(\pi\sin\Theta)^{2(\upsilon-1)}}{(\upsilon-1)!(\upsilon-1)!} \frac{\Gamma\left(\frac{1}{2}\right)\Gamma\left(\upsilon+\frac{1}{2}\right)}{(\pi\cos\Phi)^{2\upsilon+1}2^{\upsilon+1}}$$

-continued
$$\frac{2\upsilon!}{(\upsilon-1)!}s^{-2\upsilon}\frac{1}{4\pi}[\delta(\omega-\omega_n)+\delta(\omega+\omega_n)]$$

$s_n \cdot v_n = s_n \cdot c = \omega_n$ implies $r_n = \lambda_n$ which is given by Eq. (16) in the case that k is the lightlike $k^0$. In this case, Eq. (17) vanishes. Consequently, spacetime harmonics of $$\frac{\omega_n}{c} = k \text{ or } \frac{\omega_n}{c}\sqrt{\frac{\varepsilon}{\varepsilon_o}} = k$$

for which the Fourier transform of the current-density function is nonzero do not exist. Radiation due to charge motion does not occur in any medium when this boundary condition is met. Nonradiation is also determined directly from the fields based on Maxwell's equations as given in Sec. 1.C.c.

1.C.c Nonradiation Based on the Electron Electromagnetic Fields and the Poynting Power Vector A point charge undergoing periodic motion accelerates and as a consequence radiates according to the Larmor formula:

$$P = \frac{1}{4\pi\varepsilon_0}\frac{2e^2}{3c^3}a^2 \quad (18)$$

where e is the charge, $\alpha$ is its acceleration, $\epsilon_0$ is the permittivity of free space, and c is the speed of light. Although an accelerated point particle radiates, an extended distribution modeled as a superposition of accelerating charges does not have to radiate [11, 16, 19-21]. In Ref. [3] and Appendix I, Chp. 1 of Ref. [1], the electromagnetic far field is determined from the current distribution in order to obtain the condition, if it exists, that the electron current distribution must satisfy such that the electron does not radiate. The current follows from Eqs. (14-15). The currents corresponding to Eq. (14) and first term of Eq. (15) are static. Thus, they are trivially nonradiative. The current due to the time dependent term of Eq. (15) corresponding to p, d, f, etc. orbitals is $$J = \frac{\omega_n}{2\pi}\frac{e}{4\pi r_n^2}N[\delta(r-r_n)]\text{Re}\{Y_\ell^m(\theta,\phi)\}[u(t)\times r] \quad (19)$$
$$= \frac{\omega_n}{2\pi}\frac{e}{4\pi r_n^2}N'[\delta(r-r_n)](P_\ell^m(\cos(\theta)\cos(m\phi+\omega_n t))[u\times r]$$
$$= \frac{\omega_n}{2\pi}\frac{e}{4\pi r_n^2}N'[\delta(r-r_n)](P_\ell^m(\cos(\theta)\cos(m\phi+\omega_n t))\sin\theta\hat{\phi}$$

where to keep the form of the spherical harmonic as a traveling wave about the z-axis, $\dot{\omega}_n = m\omega_n$ and N and N' are normalization constants. The vectors are defined as $$\hat{\phi} = \frac{\hat{u}\times\hat{r}}{|\hat{u}\times\hat{r}|} = \frac{\hat{u}\times\hat{r}}{\sin\theta}; \hat{u} = \hat{z} = \text{orbital axis} \quad (20)$$

$$\hat{\theta} = \hat{\phi}\times\hat{r} \quad (21)$$

"^" denotes the unit vectors $$\hat{u} \equiv \frac{u}{|u|},$$

non-unit vectors are designed in bold, and the current function is normalized. For the electron source current given by Eq. (19), each comprising a multipole of order (l,m) with a time dependence $e^{i\omega_n t}$, the far-field solutions to Maxwell's equations are given by $$B = -\frac{i}{k}a_M(\ell,m)\nabla\times g_\ell(kr)X_{\ell,m} \quad (22)$$
$$E = a_M(\ell,m)g_\ell(kr)X_{\ell,m}$$

and the time-averaged power radiated per solid angle $$\frac{dP(\ell,m)}{d\Omega}$$

is $$\frac{dP(\ell,m)}{d\Omega} = \frac{c}{8\pi k^2}|a_M(\ell,m)|^2|X_{\ell,m}|^2 \quad (23)$$

where $a_M(\ell,m)$ is $$a_M(\ell,m) = \frac{-ek^2}{c\sqrt{\ell(\ell+1)}}\frac{\omega_n}{2\pi}Nj_\ell(kr_n)\Theta\sin(mks) \quad (24)$$

In the case that k is the lightlike $k^0$, then $k=\omega_n/c$, in Eq. (24), and Eqs. (22-23) vanishes for $$s=vT_n=R=r_n=\lambda_n \quad (25)$$

There is no radiation.

1.D. Magnetic Field Equations of the Electron

The orbitsphere is a shell of negative charge current comprising correlated charge motion along great circles. For l=0, the orbitsphere gives rise to a magnetic moment of 1 Bohr magneton [22]. (The details of the derivation of the magnetic parameters including the electron g factor are given in Ref. [3] and Chp. 1 of Ref. [1].)

$$\mu_B = \frac{e\hbar}{2m_e} = 9.274\times10^{-24}JT^{-1} \quad (26)$$

Figure 5:
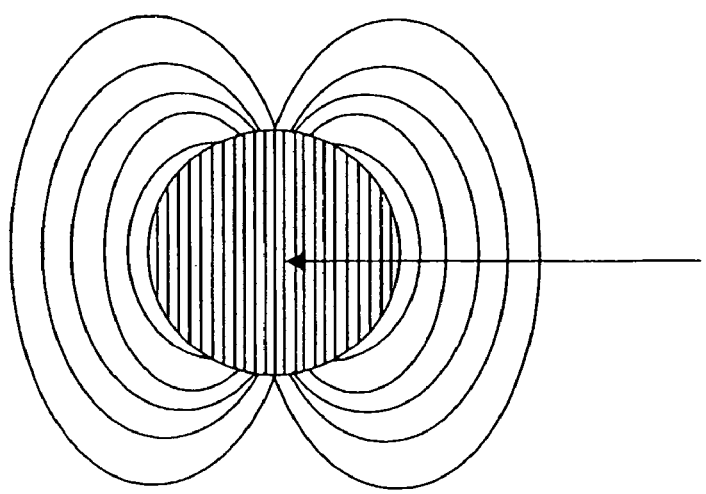
FIG. 5 shows the magnetic field of an electron orbitsphere (z-axis defined as the vertical axis).

The magnetic field of the electron shown in FIG. 5 is given by $$H = \frac{e\hbar}{m_e r_n^3}(i_r\cos\theta - i_\theta\sin\theta) \text{ for } r < r_n \quad (27)$$

$$H = \frac{e\hbar}{2m_e r^3}(i_r 2\cos\theta + i_\theta\sin\theta) \text{ for } r > r_n \quad (28)$$

The energy stored in the magnetic field of the electron is $$E_{mag} = \frac{1}{2}\mu_o \int_0^{2\pi}\int_0^{\pi}\int_0^{\infty} H^2 r^2 \sin\theta \, dr \, d\theta \, d\Phi \quad (29)$$

$$E_{mag\,total} = \frac{\pi\mu_o e^2 \hbar^2}{m_e^2 r_1^3} \quad (30)$$

1.E. Stern-Gerlach Experiment

The Stern-Gerlach experiment implies a magnetic moment of one Bohr magneton and an associated angular momentum quantum number of ½. Historically, this quantum number is called the spin quantum number, $$s\left(s = \frac{1}{2}; m_s = \pm\frac{1}{2}\right).$$

The superposition of the vector projection of the orbitsphere angular momentum on the z-axis is $$\frac{\hbar}{2}$$

with an orthogonal component of $$\frac{\hbar}{4}.$$

Excitation of a resonant Larmor precession gives rise to $\hbar$ on an axis S that precesses about the z-axis called the spin axis at the Larmor frequency at an angle of $$\theta = \frac{\pi}{3}$$

to give a perpendicular projection of $$S_\perp = \hbar \sin\frac{\pi}{3} = \pm\sqrt{\frac{3}{4}}\,\hbar\, i_{Y_R} \quad (31)$$

and a projection onto the axis of the applied magnetic field of $$S_\parallel = \hbar \cos\frac{\pi}{3} = \pm\frac{\hbar}{2} i_z \quad (32)$$

The superposition of the $$\frac{\hbar}{2},$$

z-axis component of the orbitsphere angular momentum and the $$\frac{\hbar}{2},$$

z-axis component of S gives $\hbar$ corresponding to the observed electron magnetic moment of a Bohr magneton, $\mu_B$.

1.F. Electron g Factor

Conservation of angular momentum of the orbitsphere permits a discrete change of its "kinetic angular momentum" (r×mv) by the applied magnetic field of $$\frac{\hbar}{2},$$

and concomitantly the "potential angular momentum" (r×eA) must change by $$-\frac{\hbar}{2}.$$

$$\Delta L = \frac{\hbar}{2} - r \times eA \quad (33)$$

$$= \left[\frac{\hbar}{2} - \frac{e\phi}{2\pi}\right]\hat{z} \quad (34)$$

In order that the change of angular momentum, $\Delta L$, equals zero, $\phi$ must be $$\Phi_0 = \frac{h}{2e},$$

the magnetic flux quantum. The magnetic moment of the electron is parallel or antiparallel to the applied field only. During the spin-flip transition, power must be conserved. Power flow is governed by the Poynting power theorem, $$\nabla \cdot (E \times H) = -\frac{\partial}{\partial t}\left[\frac{1}{2}\mu_o H \cdot H\right] - \frac{\partial}{\partial t}\left[\frac{1}{2}\varepsilon_o E \cdot E\right] - J \cdot E \quad (35)$$

Eq. (36) gives the total energy of the flip transition which is the sum of the energy of reorientation of the magnetic moment (1st term), the magnetic energy (2nd term), the electric energy (3rd term), and the dissipated energy of a fluxon treading the orbitsphere (4th term), respectively, $$\Delta E_{mag}^{spin} = 2\left(1 + \frac{\alpha}{2\pi} + \frac{2}{3}\alpha^2\left(\frac{\alpha}{2\pi}\right) - \frac{4}{3}\left(\frac{\alpha}{2\pi}\right)^2\right)\mu_B B \quad (36)$$

$$\Delta E_{mag}^{spin} = g\mu_B B \quad (37)$$

where the stored magnetic energy corresponding to the $$\frac{\partial}{\partial t}\left[\frac{1}{2}\mu_o H \cdot H\right]$$

term increases, the stored electric energy corresponding to the $$\frac{\partial}{\partial t}\left[\frac{1}{2}\varepsilon_o E \cdot E\right]$$

term increases, and the J·E term is dissipative. The spin-flip transition can be considered as involving a magnetic moment of g times that of a Bohr magneton. The g factor is redesignated the fluxon g factor as opposed to the anomalous g factor. Using $\alpha^{-1}=137.03603(82)$, the calculated value of $$\frac{g}{2}$$

is 1.001 159 652 137. The experimental value [23] of $$\frac{g}{2}$$

is 1.001 159 652 188(4).

1.G. Spin and Orbital Parameters

The total function that describes the spinning motion of each electron orbitsphere is composed of two functions. One function, the spin function, is spatially uniform over the orbitsphere, spins with a quantized angular velocity, and gives rise to spin angular momentum. The other function, the modulation function, can be spatially uniform—in which case there is no orbital angular momentum and the magnetic moment of the electron orbitsphere is one Bohr magneton—or not spatially uniform—in which case there is orbital angular momentum. The modulation function also rotates with a quantized angular velocity.

The spin function of the electron corresponds to the nonradiative n=1, l=0 state of atomic hydrogen which is well known as an s state or orbital. (See FIG. 1 for the charge function and FIG. 2 for the current function.) In cases of orbitals of heavier elements and excited states of one electron atoms and atoms or ions of heavier elements with the l quantum number not equal to zero and which are not constant as given by Eq. (14), the constant spin function is modulated by a time and spherical harmonic function as given by Eq. (15) and shown in FIG. 3. The modulation or traveling charge density wave corresponds to an orbital angular momentum in addition to a spin angular momentum. These states are typically referred to as p, d, f, etc. orbitals. Application of Haus's [16] condition also predicts nonradiation for a constant spin function modulated by a time and spherically harmonic orbital function. There is acceleration without radiation as also shown in Sec. 1.C.c. (Also see Abbott and Griffiths, Goedecke, and Daboul and Jensen [19-21]). However, in the case that such a state arises as an excited state by photon absorption, it is radiative due to a radial dipole term in its current density function since it possesses spacetime Fourier Transform components synchronous with waves traveling at the speed of light [16]. (See Instability of Excited States section of Ref. [1].)

1.G.a Moment of Inertia and Spin and Rotational Energies

The moments of inertia and the rotational energies as a function of the l quantum number for the solutions of the time-dependent electron charge density functions (Eqs. (14-15)) given in Sec. 1.B are solved using the rigid rotor equation [18]. The details of the derivations of the results as well as the demonstration that Eqs. (14-15) with the results given infra. are solutions of the wave equation are given in Chp 1, Rotational Parameters of the Electron (Angular Momentum, Rotational Energy, Moment of Inertia) section of Ref. [1].

$$\ell = 0$$

$$I_z = I_{spin} = \frac{m_e r_n^2}{2} \qquad (38)$$

$$L_z = I\omega i_z = \pm\frac{\hbar}{2} \qquad (39)$$

$$E_{rotational} = E_{rotational,\,spin} = \qquad (40)$$
$$\frac{1}{2}\left[I_{spin}\left(\frac{\hbar}{m_e r_n^2}\right)^2\right] = \frac{1}{2}\left[\frac{m_e r_n^2}{2}\left(\frac{\hbar}{m_e r_n^2}\right)^2\right] = \frac{1}{4}\left[\frac{\hbar^2}{2I_{spin}}\right]$$

$$T = \frac{\hbar^2}{2m_e r_n^2} \qquad (41)$$

$$\ell \neq 0$$

$$I_{orbital} = m_e r_n^2 \left[\frac{\ell(\ell+1)}{\ell^2+2\ell+1}\right]^{\frac{1}{2}} = m_e r_n^2 \sqrt{\frac{\ell}{\ell+1}} \qquad (42)$$

$$L = I\omega i_z = I_{orbital}\omega i_z = m_e r_n^2\left[\frac{\ell(\ell+1)}{\ell^2+2\ell+1}\right]^{\frac{1}{2}}\omega i_z = \qquad (43)$$
$$m_e r_n^2 \frac{\hbar}{m_e r_n^2}\sqrt{\frac{\ell}{\ell+1}} = \hbar\sqrt{\frac{\ell}{\ell+1}}$$

$$L_{z\,total} = L_{z\,spin} + L_{z\,orbital} \qquad (44)$$

$$E_{rotational\,orbital} = \qquad (45)$$
$$\frac{\hbar^2}{2I}\left[\frac{\ell(\ell+1)}{\ell^2+2\ell+1}\right] = \frac{\hbar^2}{2I}\left[\frac{\ell}{\ell+1}\right] = \frac{\hbar^2}{2m_e r_n^2}\left[\frac{\ell}{\ell+1}\right]$$

$$\langle L_{z\,orbital}\rangle = 0 \qquad (46)$$

$$\langle E_{rotational\,orbital}\rangle = 0 \qquad (47)$$

The orbital rotational energy arises from a spin function (spin angular momentum) modulated by a spherical harmonic angular function (orbital angular momentum). The time-averaged mechanical angular momentum and rotational energy associated with the wave-equation solution comprising a traveling charge-density wave on the orbitsphere is zero as given in Eqs. (46) and (47), respectively. Thus, the principal levels are degenerate except when a magnetic field is applied. In the case of an excited state, the angular momentum of $\hbar$ is carried by the fields of the trapped photon. The amplitudes that couple to external magnetic and electromagnetic fields are given by Eq. (43) and (45), respectively. The rotational energy due to spin is given by Eq. (40), and the total kinetic energy is given by Eq. (41).

1.H. Force Balance Equation

The radius of the nonradiative (n=1) state is solved using the electromagnetic force equations of Maxwell relating the charge and mass density functions wherein the angular momentum of the electron is given by $\hbar$ [1]. The reduced mass arises naturally from an electrodynamic interaction between the electron and the proton of mass $m_p$.

$$\frac{m_e}{4\pi r_1^2} \frac{v_1^2}{r_1} = \frac{e}{4\pi r_1^2} \frac{Ze}{4\pi\varepsilon_o r_1^2} - \frac{1}{4\pi r_1^2} \frac{\hbar}{m_p r_n^3} \quad (48)$$

$$r_1 = \frac{a_H}{Z} \quad (49)$$

where $a_H$ is the radius of the hydrogen atom.

1.1. Energy Calculations

From Maxwell's equations, the potential energy V, kinetic energy T, electric energy or binding energy $E_{ele}$ are $$V = \frac{-Ze^2}{4\pi\varepsilon_o r_1} =$$
$$\frac{-Z^2 e^2}{4\pi\varepsilon_o a_H} = -Z^2 \times 4.3675 \times 10^{-18} J = -Z^2 \times 27.2 \text{ eV} \quad (50)$$

$$T = \frac{Z^2 e^2}{8\pi\varepsilon_o a_H} = Z^2 \times 13.59 \text{ eV} \quad (51)$$

$$T = E_{ele} = -\frac{1}{2}\varepsilon_o \int_\infty^{r_1} E^2 \, dv \text{ where } E = -\frac{Ze}{4\pi\varepsilon_o r^2} \quad (52)$$

$$E_{ele} = -\frac{Ze^2}{8\pi\varepsilon_o r_1} = \quad (53)$$
$$-\frac{Z^2 e^2}{8\pi\varepsilon_o a_H} = -Z^2 \times 2.1786 \times 10^{-18} J = -Z^2 \times 13.598 \text{ eV}$$

The calculated Rydberg constant is 10,967,758 m$^{-1}$; the experimental Rydberg constant is 10,967,758 m$^{-1}$. For increasing Z, the velocity becomes a significant fraction of the speed of light; thus, special relativistic corrections were included in the calculation of the ionization energies of one-electron atoms that are given in TABLE I.

TABLE I

Relativistically corrected ionization energies for some one-electron atoms.

| One e Atom | Z | $\gamma^*$ [a] | Theoretical Ionization Energies (eV) [b] | Experimental Ionization Energies (eV) [c] | Relative Difference between Experimental and Calculated [d] |
|---|---|---|---|---|---|
| H | 1 | 1.000007 | 13.59838 | 13.59844 | 0.00000 |
| He$^+$ | 2 | 1.000027 | 54.40941 | 54.41778 | 0.00015 |
| Li$^{2+}$ | 3 | 1.000061 | 122.43642 | 122.45429 | 0.00015 |
| Be$^{3+}$ | 4 | 1.000109 | 217.68510 | 217.71865 | 0.00015 |
| B$^{4+}$ | 5 | 1.000172 | 340.16367 | 340.2258 | 0.00018 |
| C$^{5+}$ | 6 | 1.000251 | 489.88324 | 489.99334 | 0.00022 |
| N$^{6+}$ | 7 | 1.000347 | 666.85813 | 667.046 | 0.00028 |
| O$^{7+}$ | 8 | 1.000461 | 871.10635 | 871.4101 | 0.00035 |
| F$^{8+}$ | 9 | 1.000595 | 1102.65013 | 1103.1176 | 0.00042 |
| Ne$^{9+}$ | 10 | 1.000751 | 1361.51654 | 1362.1995 | 0.00050 |
| Na$^{10+}$ | 11 | 1.000930 | 1647.73821 | 1648.702 | 0.00058 |
| Mg$^{11+}$ | 12 | 1.001135 | 1961.35405 | 1962.665 | 0.00067 |
| Al$^{12+}$ | 13 | 1.001368 | 2302.41017 | 2304.141 | 0.00075 |
| Si$^{13+}$ | 14 | 1.001631 | 2670.96078 | 2673.182 | 0.00083 |
| P$^{14+}$ | 15 | 1.001927 | 3067.06918 | 3069.842 | 0.00090 |
| S$^{15+}$ | 16 | 1.002260 | 3490.80890 | 3494.1892 | 0.00097 |
| Cl$^{16+}$ | 17 | 1.002631 | 3942.26481 | 3946.296 | 0.00102 |
| Ar$^{17+}$ | 18 | 1.003045 | 4421.53438 | 4426.2296 | 0.00106 |
| K$^{18+}$ | 19 | 1.003505 | 4928.72898 | 4934.046 | 0.00108 |
| Ca$^{19+}$ | 20 | 1.004014 | 5463.97524 | 5469.864 | 0.00108 |
| Sc$^{20+}$ | 21 | 1.004577 | 6027.41657 | 6033.712 | 0.00104 |
| Ti$^{21+}$ | 22 | 1.005197 | 6619.21462 | 6625.82 | 0.00100 |
| V$^{22+}$ | 23 | 1.005879 | 7239.55091 | 7246.12 | 0.00091 |
| Cr$^{23+}$ | 24 | 1.006626 | 7888.62855 | 7894.81 | 0.00078 |
| Mn$^{24+}$ | 25 | 1.007444 | 8566.67392 | 8571.94 | 0.00061 |
| Fe$^{25+}$ | 26 | 1.008338 | 9273.93857 | 9277.69 | 0.00040 |
| Co$^{26+}$ | 27 | 1.009311 | 10010.70111 | 10012.12 | 0.00014 |
| Ni$^{27+}$ | 28 | 1.010370 | 10777.26918 | 10775.4 | −0.00017 |
| Cu$^{28+}$ | 29 | 1.011520 | 11573.98161 | 11567.617 | −0.00055 |

[a] Eq. (1.250) of Ref. [1] (follows Eqs. (6), (16), and (49)).
[b] Eq. (1.251) of Ref. [1] (Eq. (53) times $\gamma^*$).
[c] From theoretical calculations, interpolation of H isoelectronic and Rydberg series, and experimental data [24-25].
[d] (Experimental-theoretical)/experimental.

2. Two Electron Atoms

Two electron atoms may be solved from a central force balance equation with the nonradiation condition [1]. The centrifugal force, $F_{centrifugal}$, of each electron is given by $$F_{centrifugal} = \frac{m_e v_n^2}{r_n} \tag{54}$$

where $r_n$ is the radius of electron n which has velocity $v_n$. In order to be nonradiative, the velocity for every point on the orbitsphere is given by Eq. (6). Now, consider electron 1 initially at $$r = r_1 = \frac{a_0}{Z}$$

(the radius of the one-electron atom of charge Z given in the Sec. 1.H where $$a_0 = \frac{4\pi\varepsilon_0 \hbar^2}{e^2 m_e}$$

and the spin-nuclear interaction corresponding to the electron reduced mass is not used here since the electrons have no field at the nucleus upon pairing) and electron 2 initially at $r_n = \infty$. Each electron can be treated as $-e$ charge at the nucleus with $$E = \frac{-e}{4\pi\varepsilon_o r^2}$$

for $r > r_n$ and $E = 0$ for $r < r_n$ where $r_n$ is the radius of the electron orbitsphere. The centripetal force is the electric force, $F_{ele}$, between the electron and the nucleus. Thus, the electric force between electron 2 and the nucleus is $$F_{ele(electron\ 2)} = \frac{(Z-1)e^2}{4\pi\varepsilon_o r_2^2} \tag{55}$$

where $\varepsilon_o$ is the permittivity of free-space. The second centripetal force, $F_{mag}$, on the electron 2 (initially at infinity) from electron 1 (at $r_1$) is the magnetic force. Due to the relative motion of the charge-density elements of each electron, a radiation reaction force arises between the two electrons. This force given in Sections 6.6, 12.10, and 17.3 of Jackson [26] achieves the condition that the sum of the mechanical momentum and electromagnetic momentum is conserved. The magnetic central force is derived from the Lorentzian force which is relativistically corrected. The magnetic field of electron 2 at the radius of electron 1 follows from Eq. (1.74b) of Ref. [1] after McQuarrie [22]:

$$B = \frac{\mu_o e \hbar}{2 m_e r_2^3} \tag{56}$$

where $\mu_o$ is the permeability of free-space ($4\pi \times 10^{-1}$ N/A$^2$). The motion at each point of electron 1 in the presence of the magnetic field of electron 2 gives rise to a central force which acts at each point of electron 2. The Lorentzian force density at each point moving at velocity v given by Eq. (6) is $$F_{mag} = \frac{e}{4\pi r_2^2} v \times B \tag{57}$$

Substitution of Eq. (6) for v and Eq. (56) for B gives $$F_{mag} = \frac{1}{4\pi r_2^2} \left[ \frac{e^2 \mu_o}{2 m_e r_1} \right] \frac{\hbar^2}{m_2 r_2^3} \tag{58}$$

The term in brackets can be expressed in terms of the fine structure constant $\alpha$. The radius of the electron orbitsphere in the $v = c$ frame is $\lambdabar_c$, where $v = c$ corresponds to the magnetic field front propagation velocity which is the same in all inertial frames, independent of the electron velocity as shown by the velocity addition formula of special relativity [27]. From Eq. (7) and Eqs. (1.144-1.148) of Ref. [1]

$$\frac{e^2 \mu_o}{2 m_e r_1} = 2\pi \alpha \frac{v}{c} \tag{59}$$

where $v = c$. Based on the relativistic invariance of the electron's magnetic moment of a Bohr magneton $$\mu_B = \frac{e\hbar}{2 m_e}$$

as well as its invariant angular momentum of $\hbar$, it can be shown that the relativistic correction to Eq. (58) is $$\frac{1}{Z}$$

times the reciprocal of Eq. (59). In addition, as given in the Spin Angular Momentum of the Orbitsphere with $l = 0$ section of Ref [1], the application of a z-directed magnetic field of electron 2 given by Eq. (1.120) of Ref. [1] to the inner orbitsphere gives rise to a projection of the angular momentum of electron 1 onto an axis which precesses about the z-axis of $$\sqrt{\frac{3}{4}} \hbar.$$

The projection of the force between electron 2 and electron 1 is equivalent to that of the angular momentum onto the axis which precesses about the z-axis. Thus, Eq. (58) becomes $$F_{mag} = \frac{1}{4\pi r_2^2} \frac{1}{Z} \frac{\hbar^2}{m_e r^3} \sqrt{s(s+1)} \qquad (60)$$

Using Eq. (6), the outward centrifugal force on electron 2 is balanced by the electric force and the magnetic force (on electron 2), $$\frac{m_e}{4\pi r_2^2} \frac{v_2^2}{r_2} = \frac{m_e}{4\pi r_2^2} \frac{\hbar^2}{m_e r_2^3} = \frac{e}{4\pi r_2^2} \frac{(Z-1)e}{4\pi \varepsilon_o r_2^2} + \frac{1}{4\pi r_2^2} \frac{\hbar^2}{Z m_e r_2^3} \sqrt{s(s+1)} \qquad (61)$$

which gives the radius of both electrons as $$r_2 = r_1 = a_0 \left( \frac{1}{Z-1} - \frac{\sqrt{s(s+1)}}{Z(Z-1)} \right); s = \frac{1}{2} \qquad (62)$$

(Since the density factor always cancels, it will not be used in subsequent force balance equations).

2.A. Ionization Energies Calculated using the Poynting Power Theorem

During ionization, power must be conserved. Power flow is governed by the Poynting power theorem given by Eq. (35). Energy is superposable; thus, the calculation of the ionization energy is determined as a sum of the electric and magnetic contributions. Energy must be supplied to overcome the electric force of the nucleus, and this energy contribution is the negative of the electric work given by Eq. (64). Additionally, the electrons are initially spin paired at $r_1=r_2=0.566987 \, a_0$ producing no magnetic fields; whereas, following ionization, the electrons possess magnetic fields and corresponding energies. For helium, the contribution to the ionization energy is given as the energy stored in the magnetic fields of the two electrons at the initial radius where they become spin unpaired. Part of this energy and the corresponding relativistic term correspond to the precession of the outer electron about the z-axis due to the spin angular momentum of the inner electron. These terms are the same as those of the corresponding terms of the hyperfine structure interval of muonium as given in the Muonium Hyperfine Structure Interval section of Ref [1]. Thus, for helium, which has no electric field beyond $r_1$ the ionization energy is given by the general formula:

$$\text{Ionization Energy(He)} = \qquad (63)$$
$$-E(\text{electric}) + E(\text{magnetic})\left(1 - \frac{1}{2}\left(\left(\frac{2}{3}\cos\frac{\pi}{3}\right)^2 + \alpha\right)\right)$$

where, $$E(\text{electric}) = -\frac{(Z-1)e^2}{8\pi\varepsilon_o r_1} \qquad (64)$$

-continued $$E(\text{magnetic}) = \frac{2\pi\mu_0 e^2 \hbar^2}{m_e^2 r_1^3} = \frac{8\pi\mu_0 \mu_B^2}{r_1^3} \qquad (65)$$

Eq. (65) is derived for each of the two electrons as Eq. (1.129) of the Magnetic Parameters of the Electron (Bohr Magneton) section of Ref. [1] with the radius given by Eq. (62).

For $3 \leq Z$, a quantized electric field exists for $r>r_1$ that gives rise to a dissipative term, $J \cdot E$, of the Poynting Power Vector given by Eq. (35). Thus, the ionization energies are given by $$\text{Ionization Energy} = -\text{Electric Energy} - \frac{1}{Z}\text{Magnetic Energy} \qquad (66)$$

With the substitution of the radius given by Eq. (62) into Eq. (6), the velocity v is given by $$v = \frac{\hbar c}{\sqrt{\left(\frac{4\pi\varepsilon_0 \hbar^2}{e^2}c\left(\frac{1}{Z-1} - \frac{\sqrt{\frac{3}{4}}}{Z(Z-1)}\right)\right)^2 + \hbar^2}} = \qquad (67)$$

$$\frac{\alpha c(Z-1)}{\sqrt{\left(1 - \frac{\sqrt{\frac{3}{4}}}{Z}\right)^2 + \alpha^2(Z-1)^2}}$$

with $Z>1$. For increasing Z, the velocity becomes a significant fraction of the speed of light; thus, special relativistic corrections as given in the Special Relativistic Correction to the Ionization Energies section of Ref. [1] and Sec. 1.C.a were included in the calculation of the ionization energies of two-electron atoms given in TABLE II. The calculated ionization energy for helium is 24.58750 eV and the experimental ionization energy is 24.58741 eV. The agreement in the values is within the limit set by experimental error [28].

The solution of the helium atom is further proven to be correct since it is used to solve up through twenty-electron atoms in the Three, Four, Five, Six, Seven, Eight, Nine, Ten, Eleven, Twelve, Thirteen, Fifteen, Sixteen, Seventeen, Eighteen, Nineteen, and Twenty-Electron Atoms section of Ref. [1]. The predictions from general solutions for one through twenty-electron atoms are in remarkable agreement with the experimental values known for 400 atoms and ions.

TABLE II

Relativistically corrected ionization energies for some two-electron atoms.

| 2 e Atom | Z | $r_1$ $(a_o)$ [a] | Electric Energy [b] (eV) | Magnetic Energy [c] (eV) | Velocity (m/s) [d] | $\gamma^*$ [e] | Theoretical Ionization Energies f (eV) | Experimental ionization Energies g (eV) | Relative Error [h] |
|---|---|---|---|---|---|---|---|---|---|
| He | 2 | 0.566987 | 23.996467 | 0.590536 | 3.85845E+06 | 1.000021 | 24.58750 | 24.58741 | −0.000004 |
| $Li^+$ | 3 | 0.35566 | 76.509 | 2.543 | 6.15103E+06 | 1.00005 | 75.665 | 75.64018 | −0.0003 |
| $Be^{2+}$ | 4 | 0.26116 | 156.289 | 6.423 | 8.37668E+06 | 1.00010 | 154.699 | 153.89661 | −0.0052 |
| $B^{3+}$ | 5 | 0.20670 | 263.295 | 12.956 | 1.05840E+07 | 1.00016 | 260.746 | 259.37521 | −0.0053 |
| $C^{4+}$ | 6 | 0.17113 | 397.519 | 22.828 | 1.27836E+07 | 1.00024 | 393.809 | 392.087 | −0.0044 |
| $N^{5+}$ | 7 | 0.14605 | 558.958 | 36.728 | 1.49794E+07 | 1.00033 | 553.896 | 552.0718 | −0.0033 |
| $O^{6+}$ | 8 | 0.12739 | 747.610 | 55.340 | 1.71729E+07 | 1.00044 | 741.023 | 739.29 | −0.0023 |
| $F^{7+}$ | 9 | 0.11297 | 963.475 | 79.352 | 1.93649E+07 | 1.00057 | 955.211 | 953.9112 | −0.0014 |
| $Ne^{8+}$ | 10 | 0.10149 | 1206.551 | 109.451 | 2.15560E+07 | 1.00073 | 1196.483 | 1195.8286 | −0.0005 |
| $Na^{9+}$ | 11 | 0.09213 | 1476.840 | 146.322 | 2.37465E+07 | 1.00090 | 1464.871 | 1465.121 | 0.0002 |
| $Mg^{10+}$ | 12 | 0.08435 | 1774.341 | 190.652 | 2.59364E+07 | 1.00110 | 1760.411 | 1761.805 | 0.0008 |
| $Al^{11+}$ | 13 | 0.07778 | 2099.05 | 243.13 | 2.81260E+07 | 1.00133 | 2083.15 | 2085.98 | 0.0014 |
| $Si^{12+}$ | 14 | 0.07216 | 2450.98 | 304.44 | 3.03153E+07 | 1.00159 | 2433.13 | 2437.63 | 0.0018 |
| $P^{13+}$ | 15 | 0.06730 | 2830.11 | 375.26 | 3.25043E+07 | 1.00188 | 2810.42 | 2816.91 | 0.0023 |
| $S^{14+}$ | 16 | 0.06306 | 3236.46 | 456.30 | 3.46932E+07 | 1.00221 | 3215.09 | 3223.78 | 0.0027 |
| $Cl^{15+}$ | 17 | 0.05932 | 3670.02 | 548.22 | 3.68819E+07 | 1.00258 | 3647.22 | 3658.521 | 0.0031 |
| $Ar^{16+}$ | 18 | 0.05599 | 4130.79 | 651.72 | 3.90705E+07 | 1.00298 | 4106.91 | 4120.8857 | 0.0034 |
| $K^{17+}$ | 19 | 0.05302 | 4618.77 | 767.49 | 4.12590E+07 | 1.00344 | 4594.25 | 4610.8 | 0.0036 |
| $Ca^{18+}$ | 20 | 0.05035 | 5133.96 | 896.20 | 4.34475E+07 | 1.00394 | 5109.38 | 5128.8 | 0.0038 |
| $Sc^{19+}$ | 21 | 0.04794 | 5676.37 | 1038.56 | 4.56358E+07 | 1.00450 | 5652.43 | 5674.8 | 0.0039 |
| $Ti^{20+}$ | 22 | 0.04574 | 6245.98 | 1195.24 | 4.78241E+07 | 1.00511 | 6223.55 | 6249 | 0.0041 |
| $V^{21+}$ | 23 | 0.04374 | 6842.81 | 1366.92 | 5.00123E+07 | 1.00578 | 6822.93 | 6851.3 | 0.0041 |
| $Cr^{22+}$ | 24 | 0.04191 | 7466.85 | 1554.31 | 5.22005E+07 | 1.00652 | 7450.76 | 7481.7 | 0.0041 |
| $Mn^{23+}$ | 25 | 0.04022 | 8118.10 | 1758.08 | 5.43887E+07 | 1.00733 | 8107.25 | 8140.6 | 0.0041 |
| $Fe^{24+}$ | 26 | 0.03867 | 8796.56 | 1978.92 | 5.65768E+07 | 1.00821 | 8792.66 | 8828 | 0.0040 |
| $Co^{25+}$ | 27 | 0.03723 | 9502.23 | 2217.51 | 5.87649E+07 | 1.00917 | 9507.25 | 9544.1 | 0.0039 |
| $Ni^{26+}$ | 28 | 0.03589 | 10235.12 | 2474.55 | 6.09529E+07 | 1.01022 | 10251.33 | 10288.8 | 0.0036 |
| $Cu^{27+}$ | 29 | 0.03465 | 10995.21 | 2750.72 | 6.31409E+07 | 1.01136 | 11025.21 | 11062.38 | 0.0034 |

[a] From Eq. (62).
[b] From Eq. (64).
[c] From Eq. (65).
[d] From Eq. (67).
[e] From Eq. (1.250) of Ref. [1] (follows Eqs. (6), (16), and (49)) with the velocity given by Eq. (67).
[f] From Eqs. (63) and (66) with E(electric) of Eq. (64) relativistically corrected by $\gamma^*$ according to Eq.(1.251) of Ref. [1] except that the electron-nuclear electrodynamic relativistic factor corresponding to the reduced mass of Eqs. (1.213-1.223) was not included.
[g] From theoretical calculations for ions $Ne^{8+}$ to $Cu^{28+}$ [24-25].
[h] (Experimental-theoretical)/experimental.

The initial central force balance equations with the nonradiation condition, the initial radii, and the initial energies of the electrons of multi-electron atoms before excitation is given in R. Mills, *The Grand Unified Theory of Classical Quantum Mechanics*, January 2005 Edition, BlackLight Power, Inc., Cranbury, N.J., ("'05 Mills GUT") and R. L. Mills, "Exact Classical Quantum Mechanical Solutions for One-Through Twenty-Electron Atoms", submitted; posted at http://www.blacklightpower.com/pdf/technical/Exact%20 Classical%20Quantum%20Mechanical%20Solutions%20for %20One-%20Through%20Twenty-Electron%20Atoms %20042204.pdf which are herein incorporated by reference in their entirety.

3. Excited States of Helium (In this section equation numbers of the form (#.#) correspond to those given in R. Mills, *The Grand Unified Theory of Classical Quantum Mechanics*, January 2005 Edition, BlackLight Power, Inc., Cranbury, N.J., ("'05 Mills GUT")).

Bound electrons are described by a charge-density (mass-density) function which is the product of a radial delta function ($f(r)=\delta(r-r_n)$), two angular functions (spherical harmonic functions), and a time harmonic function. Thus, a bound electron is a dynamic "bubble-like" charge-density function. The two-dimensional spherical surface called an electron orbitsphere can exist in a bound state at only specified distances from the nucleus. More explicitly, the orbitsphere comprises a two-dimensional spherical shell of moving charge. The current pattern of the orbitsphere that gives rise to the phenomenon corresponding to the spin quantum number comprises an infinite series of correlated orthogonal great circle current loops. As given in the Orbitsphere Equation of Motion for l=0 section, the current pattern (shown in FIG. 2) is generated over the surface by two orthogonal sets of an infinite series of nested rotations of two orthogonal great circle current loops where the coordinate axes rotate with the two orthogonal great circles. Each infinitesimal rotation of the infinite series is about the new x-axis and new y-axis which results from the preceding such rotation. For each of the two sets of nested rotations, the angular sum of the rotations about each rotating x-axis and y-axis totals $\sqrt{2}\pi$ radians. The spin function of the electron corresponds to the nonradiative n=1, l=0 state which is well known as an s state or orbital. (See FIG. 1 for the charge function and FIG. 2 for the current function.) In cases of orbitals of excited states with the l quantum number not equal to zero and which are not constant as given by Eq. (1.64), the constant spin function is modulated by a time and spherical harmonic function as given by Eq. (1.65) and shown in FIG. 3. The modulation or traveling charge-density wave corresponds to an orbital angular momentum in addition to a spin angular momentum. These states are typically referred to as p, d, f, etc. orbitals.

Each orbitsphere is a spherical shell of negative charge (total charge=−e) of zero thickness at a distance $r_n$ from the nucleus (charge=+Ze). It is well known that the field of a spherical shell of charge is zero inside the shell and that of a point charge at the origin outside the shell [29] (See FIG. 1.12 of Ref. [1]). The field of each electron can be treated as that corresponding to a −e charge at the origin with $$E = \frac{-e}{4\pi\varepsilon_o r^2}$$

for $r > r_n$ and $E=0$ for $r < r_n$ where $r_n$ is the radius of the electron orbitsphere. Thus, as shown in the Two-Electron Atom section of Ref. [1], the central electric fields due to the helium nucleus are $$E = \frac{2e}{4\pi\varepsilon_o r^2}$$

and $$E = \frac{e}{4\pi\varepsilon_o r^2}$$

for $r < r_1$ and $r_1 < r < r_2$, respectively. In the ground state of the helium atom, both electrons are at $r_1 = r_2 = 0.567 a_o$. When a photon is absorbed, one of the initially indistinguishable electrons called electron 1 moves to a smaller radius, and the other called electron 2 moves to a greater radius. In the limiting case of the absorption of an ionizing photon, electron 1 moves to the radius of the helium ion, $r_1 = 0.5 a_o$, and electron 2 moves to a continuum radius, $r_2 = \infty$. When a photon is absorbed by the ground state helium atom it generates an effective charge, $Z_{P\text{-}eff}$, within the second orbitsphere such that the electrons move in opposite radial directions while conserving energy and angular momentum. We can determine $Z_{P\text{-}eff}$ of the "trapped photon" electric field by requiring that the resonance condition is met for photons of discrete energy, frequency, and wavelength for electron excitation in an electromagnetic potential energy well.

It is well known that resonator cavities can trap electromagnetic radiation of discrete resonant frequencies. The orbitsphere is a resonator cavity which traps single photons of discrete frequencies. Thus, photon absorption occurs as an excitation of a resonator mode. The free space photon also comprises a radial Dirac delta function, and the angular momentum of the photon given by $$m = \int \frac{1}{8\pi c} \text{Re}[r \times (E \times B^*)] dx^4 = \hbar$$

in the Photon section of Ref. [1] is conserved [30] for the solutions for the resonant photons and excited state electron functions as shown for one-electron atoms in the Excited States of the One-Electron Atom (Quantization) section of Ref. [1]. The correspondence principle holds. That is the change in angular frequency of the electron is equal to the angular frequency of the resonant photon that excites the resonator cavity mode corresponding to the transition, and the energy is given by Planck's equation. It can be demonstrated that the resonance condition between these frequencies is to be satisfied in order to have a net change of the energy field [31].

In general, for a macroscopic multipole with a single m value, a comparison of Eq. (2.33) and Eq. (2.25) shows that the relationship between the angular momentum $M_z$, energy U, and angular frequency ω is given by Eq. (2.34):

$$\frac{dM_z}{dr} = \frac{m}{\omega} \frac{dU}{dr} \tag{9.1}$$

independent of r where m is an integer. Furthermore, the ratio of the square of the angular momentum, $M^2$, to the square of the energy, $U^2$, for a pure (l, m) multipole follows from Eq. (2.25) and Eqs. (2.31-2.33) as given by Eq. (2.35):

$$\frac{M^2}{U^2} = \frac{m^2}{\omega^2} \tag{9.2}$$

From Jackson [32], the quantum mechanical interpretation is that the radiation from such a multipole of order (l, m) carries off $m\hbar$ units of the z component of angular momentum per photon of energy $\hbar\omega$. However, the photon and the electron can each posses only $\hbar$ of angular momentum which requires that Eqs. (9.1-9.2) correspond to a state of the radiation field containing m photons.

As shown in the Excited States of the One-Electron Atom (Quantization) section of Ref. [1] during excitation the spin, orbital, or total angular momentum of the orbitsphere can change by zero or $\pm\hbar$. The selection rules for multipole transitions between quantum states arise from conservation of the photon's multipole moment and angular momentum of $\hbar$. In an excited state, the time-averaged mechanical angular momentum and rotational energy associated with the traveling charge-density wave on the orbitsphere is zero (Eq. (1.98)), and the angular momentum of $\hbar$ of the photon that excites the electronic state is carried by the fields of the trapped photon. The amplitudes of the rotational energy, moment of inertia, and angular momentum that couple to external magnetic and electromagnetic fields are given by Eq. (1.95) and (1.96), respectively. Furthermore, the electron charge-density waves are nonradiative due to the angular motion as shown in the Appendix 1: Nonradiation Based on the Electromagnetic Fields and the Poynting Power Vector section of Ref. [1]. But, excited states are radiative due to a radial dipole that arises from the presence of the trapped photon as shown in the Instability of Excited States section of Ref. [1] corresponding to m=1 in Eqs. (9.1-9.2).

Then, as shown in the Excited States of the One-Electron Atom (Quantization) section and the Derivation of the Rotational Parameters of the Electron section of Ref. [1], the total number of multipoles, $N_{l,s}$, of an energy level corresponding to a principal quantum number n where each multipole corresponds to an l and ml quantum number is $$N_{l,s} = \sum_{l=0}^{n-1} \sum_{m_l=-l}^{+l} 1 = \sum_{l=0}^{n-1} 2l + 1 = (l+1)^2 = l^2 + 2l + 1 = n^2 \tag{9.3}$$

Any given state may be due to a direct transition or due to the sum of transitions between all intermediate states wherein the multiplicity of possible multipoles increases with higher states. Then, the relationships between the parameters of Eqs. (9.1) and (9.2) due to transitions of quantized angular momentum $\hbar$, energy $\hbar\omega$, and radiative via a radial dipole are given by substitution of m=1 and normalization of the energy U by the total number of degenerate multipoles, $n^2$. This requires that the photon's electric field superposes that of the nucleus for $r_1 < r < r_2$ such that the radial electric field has a magnitude proportional to e/n at the electron 2 where n=2, 3, 4, . . . for excited states such that U is decreased by the factor of $1/n^2$.

Energy is conserved between the electric and magnetic energies of the helium atom as shown by Eq. (7.26). The helium atom and the "trapped photon" corresponding to a transition to a resonant excited state have neutral charge and obey Maxwell's equations. Since charge is relativistically invariant, the energies in the electric and magnetic fields of the electrons of the helium atom must be conserved as photons are emitted or absorbed. The corresponding forces are determined from the requirement that the radial excited-state electric field has a magnitude proportional to e/n at electron 2.

The "trapped photon" is a "standing electromagnetic wave" which actually is a traveling wave that propagates on the surface around the z-axis, and its source current is only at the orbitsphere. The time-function factor, k(t), for the "standing wave" is identical to the time-function factor of the orbitsphere in order to satisfy the boundary (phase) condition at the orbitsphere surface. Thus, the angular frequency of the "trapped photon" has to be identical to the angular frequency of the electron orbitsphere, $\omega_n$, given by Eq. (1.55). Furthermore, the phase condition requires that the angular functions of the "trapped photon" have to be identical to the spherical harmonic angular functions of the electron orbitsphere. Combining k(t) with the $\phi$-function factor of the spherical harmonic gives $e^{i(m\phi - \omega_n t)}$ for both the electron and the "trapped photon" function.

The photon "standing wave" in an excited electronic state is a solution of Laplace's equation in spherical coordinates with source currents given by Eq. (2.11) "glued" to the electron and phase-locked to the electron current density wave that travel on the surface with a radial electric field. As given in the Excited States of the One-Electron Atom (Quantization) section of Ref. [1], the photon field is purely radial since the field is traveling azimuthally at the speed of light even though the spherical harmonic function has a velocity less than light speed given by Eq. (1.56). The photon field does not change the nature of the electrostatic field of the nucleus or its energy except at the position of the electron. The photon "standing wave" function comprises a radial Dirac delta function that "samples" the Laplace equation solution only at the position infinitesimally inside of the electron current-density function and superimposes with the proton field to give a field of radial magnitude corresponding to a charge of e/n where n,=2, 3, 4, . . . .

The electric field of the nucleus for $r_1 < r < r_2$ is $$E_{nucleus} = \frac{e}{4\pi\varepsilon_o r^2} \quad (9.4)$$

From Eq. (2.15), the equation of the electric field of the "trapped photon" for $r=r_2$ where $r_2$ is the radius of electron 2, is $$E_{r_{photon\,n,l,m}|_{r=r_2}} = \qquad (9.5)$$
$$\frac{e}{4\pi\varepsilon_o r_2^2}\left[-1 + \frac{1}{n}[Y_0^0(\theta,\phi) + \text{Re}\{Y_l^m(\theta,\phi)e^{i\omega_n t}\}]\right]\delta(r-r_n)$$

$\omega_n = 0$ for $m = 0m$

The total central field for $r=r_2$ is given by the sum of the electric field of the nucleus and the electric field of the "trapped photon".

$$E_{total} = E_{nucleus} + E_{photon} \qquad (9.6)$$

Substitution of Eqs. (9.4) and (9.5) into Eq. (9.6) gives for $r_1 < r < r_2$, $$E_{r_{total}} = \qquad (9.7)$$
$$\frac{e}{4\pi\varepsilon_o r_1^2} + \frac{e}{4\pi\varepsilon_o r_2^2}\left[-1 + \frac{1}{n}[Y_0^0(\theta,\phi) + \text{Re}\{Y_l^m(\theta,\phi)e^{i\omega_n t}\}]\right]$$
$$\delta(r-r_n)$$
$$= \frac{1}{n}\frac{e}{4\pi\varepsilon_o r_2^2}[Y_0^0(\theta,\phi) + \text{Re}\{Y_l^m(\theta,\phi)e^{i\omega_n t}\}]\delta(r-r_n)$$

$\omega_n = 0$ for $m = 0$

For $r=r_2$ and m=0, the total radial electric field is $$E_{r_{total}} = \frac{1}{n}\frac{e}{4\pi\varepsilon_o r^2} \qquad (9.8)$$

The result is equivalent to Eq. (2.17) of the Excited States of the One-Electron Atom (Quantization) section of Ref. [1].

In contrast to short comings of quantum-mechanical equations, with classical quantum mechanics (CQM), all excited states of the helium atom can be exactly solved in closed form. The radii of electron 2 are determined from the force balance of the electric, magnetic, and centrifugal forces that corresponds to the minimum of energy of the system. The excited-state energies are then given by the electric energies at these radii. All singlet and triplet states with l=0 or l≠0 are solved exactly except for small terms corresponding to the magnetostatic energies in the magnetic fields of excited-state electrons, spin-nuclear interactions, and the very small term due to spin-orbital coupling. In the case of spin-nuclear interactions, $\alpha_{He}$ which includes the reduced electron mass according to Eqs. (1.221-1.224) was used rather than $\alpha_0$ as a partial correction, and a table of the spin-orbital energies was calculated for l=1 to compare to the effect of different l quantum numbers. For over 100 states, the agreement between the predicted and experimental results are remarkable.

3. A Singlet Excited States with l=0 ($1s^2 \rightarrow 1s^1(ns)^1$)

With l=0, the electron source current in the excited state is a constant function given by Eq. (1.64) that spins as a globe about the z-axis:

$$\rho(r, \theta, \phi, t) = \frac{e}{8\pi r^2}[\delta(r - r_n)][Y_0^0(\theta, \phi) + Y_l^m(\theta, \phi)] \quad (9.9)$$

As given in the Derivation of the Magnetic Field section in Chapter One of Ref. [1] and by Eq. (12.342), the current is a function of sin θ which gives rise to a correction of ⅔ to the field given by Eq. (7.4) and, correspondingly, the magnetic force of two-electron atoms given by Eq. (7.15). The balance between the centrifugal and electric and magnetic forces is given by the Eq. (7.18):

$$\frac{m_e v^2}{r_2} = \frac{\hbar^2}{m_e r_2^3} = \frac{1}{n}\frac{e^2}{4\pi\varepsilon_o r_2^2} + \frac{2}{3}\frac{1}{n}\frac{\hbar^2}{2m_e r_2^3}\sqrt{s(s+1)} \quad (9.10)$$

with the exceptions that the electric and magnetic forces are reduced by a factor of $$\frac{1}{n}$$

since the corresponding charge from Eq. (9.8) is $$\frac{e}{n}$$

and the magnetic force is further corrected by the factor of ⅔. With $$s = \frac{1}{2},$$

$$r_2 = \left[n - \frac{\sqrt{\frac{3}{4}}}{3}\right]a_{He} \quad (9.11)$$

$$n = 2, 3, 4, \ldots$$

The excited-state energy is the energy stored in the electric field, $E_{ele}$, given by Eqs. (1.232), (1.233), and (10.102) which is the energy of electron 2 relative to the ionized electron at rest having zero energy:

$$E_{ele} = -\frac{1}{n}\frac{e^2}{8\pi\varepsilon_o r_2} \quad (9.12)$$

where $r_2$ is given by Eq. (9.11) and from Eq. (9.8), Z=1/n in Eq. (1.233). The energies of the various singlet excited states of helium with l=0 appear in TABLE III.

As shown in the Special Relativistic Correction to the Ionization Energies section of Ref. [1] and Sec. 1.C.a the electron possesses an invariant charge-to-mass ratio $$\left(\frac{e}{m_e}\right)$$

angular momentum of $\hbar$, and magnetic moment of a Bohr magneton ($\mu_B$). This invariance feature provides for the stability of multielectron atoms as shown in the Two-Electron Atom section of Ref. [1] and the Three, Four, Five, Six, Seven, Eight, Nine, Ten, Eleven, Twelve, Thirteen, Fourteen, Fifteen, Sixteen, Seventeen, Eighteen, Nineteen, and Twenty-Electron Atoms section of Ref. [1]. This feature also permits the existence of excited states wherein electrons magnetically interact. The electron's motion corresponds to a current which gives rise to a magnetic field with a field strength that is inversely proportional to its radius cubed as given in Eq. (9.10) wherein the magnetic field is a relativistic effect of the electric field as shown by Jackson [33]. Since the forces on electron 2 due to the nucleus and electron 1 (Eq. (9.10)) are radial/central, invariant of $r_1$, and independent of $r_1$ with the condition that $r_1 < r_2$, $r_2$ can be determined without knowledge of $r_1$. But, once $r_2$ is determined, $r_1$ can be solved using the equal and opposite magnetic force of electron 2 on electron 1 and the central Coulombic force corresponding to the nuclear charge of 2e. Using Eq. (9.10), the force balance between the centrifugal and electric and magnetic forces is $$\frac{m_e v^2}{r_1} = \frac{\hbar^2}{m_e r_1^3} = \frac{2e^2}{4\pi\varepsilon_o r_1^2} - \frac{1}{3n}\frac{\hbar^2}{m_e r_2^3}\sqrt{s(s+1)} \quad (9.13)$$

With $s = \frac{1}{2}$, $$r_1^3 - \left(\frac{12n}{\sqrt{3}}r_2^3\right)r_1 + \frac{6n}{\sqrt{3}}r_2^3 = 0 \quad (9.14)$$

$$n = 2, 3, 4, \ldots$$

where $r_2$ is given by Eq. (9.11) and $r_1$ and $r_2$ are in units of $a_{He}$. To obtain the solution of cubic Eq. (9.14), let $$g = \frac{6n}{\sqrt{3}}r_2^3 \quad (9.15)$$

Then, Eq. (9.14) becomes $$r_1^3 - 2gr_1 + g = 0 \quad n = 2, 3, 4, \ldots \quad (9.16)$$

and the roots are $$r_{11} = A + B \tag{9.17}$$

$$r_{12} = -\frac{A+B}{2} + \frac{A-B}{2}\sqrt{-3} \tag{9.18}$$

$$r_{13} = -\frac{A+B}{2} - \frac{A-B}{2}\sqrt{-3} \tag{9.19}$$

where $$A = \sqrt[3]{-\frac{g}{2} + \sqrt{\frac{g^2}{4} - \frac{8g^3}{27}}} = \sqrt[3]{\frac{g}{2}} \sqrt[3]{z} \tag{9.20}$$

and $$B = \sqrt[3]{-\frac{g}{2} - \sqrt{\frac{g^2}{4} - \frac{8g^3}{27}}} = \sqrt[3]{\frac{g}{2}} \sqrt[3]{\bar{z}} \tag{9.21}$$

The complex number z is defined by $$z = -1 + i\sqrt{\frac{32}{27}g - 1} = re^{i\theta} = r(\cos\theta + i\sin\theta) \tag{9.22}$$

where the modulus, r, and argument, θ, are $$r = \sqrt{\frac{32}{27}g} \tag{9.23}$$

and $$\theta = \frac{\pi}{2} + \sin^{-1}(1/r) \tag{9.24}$$

respectively. The cube roots are $$\sqrt[3]{z} = \sqrt[3]{r}\, e^{i\theta/3} = \sqrt[3]{r}\left(\cos\frac{\theta}{3} + i\sin\frac{\theta}{3}\right) \tag{9.25}$$

$$\sqrt[3]{\bar{z}} = \sqrt[3]{r}\, e^{-i\theta/3} = \sqrt[3]{r}\left(\cos\frac{\theta}{3} - i\sin\frac{\theta}{3}\right) \tag{9.26}$$

So, $$A = \sqrt[3]{\frac{g}{2}r}\left(\cos\frac{\theta}{3} + i\sin\frac{\theta}{3}\right) \tag{9.27}$$

and $$B = \sqrt[3]{\frac{g}{2}r}\left(\cos\frac{\theta}{3} - i\sin\frac{\theta}{3}\right) \tag{9.28}$$

The real and physical root is $$r_1 = r_{13} = -\sqrt{\frac{2}{3}g}\left(\cos\frac{\theta}{3} - \sqrt{3}\sin\frac{\theta}{3}\right) \tag{9.29}$$

TABLE III

Calculated and experimental energies of He I singlet excited states with l = 0 (1s² → 1s¹(ns)¹).

| n | $r_1$ $(a_{He})$ [a] | $r_2$ $(a_{He})$ [b] | Term Symbol | $E_{ele}$ CQM He I Energy Levels [c] (eV) | NIST He I Energy Levels [d] (eV) | Difference CQM − NIST (eV) | Relative Difference [e] (CQM − NIST) |
|---|---|---|---|---|---|---|---|
| 2 | 0.501820 | 1.71132 | 1s2s ¹S | −3.97465 | −3.97161 | −0.00304 | 0.00077 |
| 3 | 0.500302 | 2.71132 | 1s3s ¹S | −1.67247 | −1.66707 | −0.00540 | 0.00324 |
| 4 | 0.500088 | 3.71132 | 1s4s ¹S | −0.91637 | −0.91381 | −0.00256 | 0.00281 |
| 5 | 0.500035 | 4.71132 | 1s5s ¹S | −0.57750 | −0.57617 | −0.00133 | 0.00230 |
| 6 | 0.500016 | 5.71132 | 1s6s ¹S | −0.39698 | −0.39622 | −0.00076 | 0.00193 |
| 7 | 0.500009 | 6.71132 | 1s7s ¹S | −0.28957 | −0.2891 | −0.00047 | 0.00163 |
| 8 | 0.500005 | 7.71132 | 1s8s ¹S | −0.22052 | −0.2202 | −0.00032 | 0.00144 |
| 9 | 0.500003 | 8.71132 | 1s9s ¹S | −0.17351 | −0.1733 | −0.00021 | 0.00124 |
| 10 | 0.500002 | 9.71132 | 1s10s ¹S | −0.14008 | −0.13992 | −0.00016 | 0.00116 |
| 11 | 0.500001 | 10.71132 | 1s11s ¹S | −0.11546 | −0.11534 | −0.00012 | 0.00103 |
| | | | | | Avg. | −0.00144 | 0.00175 |

[a] Radius of the inner electron 1 from Eq. (9.29).
[b] Radius of the outer electron 2 from Eq. (9.11).
[c] Classical quantum mechanical (CQM) calculated energy levels given by the electric energy (Eq. (9.12)).
[d] Experimental NIST levels [34] with the ionization potential defined as zero.
[e] (Theoretical−Experimental)/Experimental.

3.B Triplet Excited States with $l=(1s^2 \to 1s^1(ns)^l)$

For $l=0$, time-independent charge-density waves corresponding to the source currents travel on the surface of the orbitsphere of electron 2 about the z-axis at the angular frequency given by Eq. (1.55). In the case of singlet states, the current due to spin of electron 1 and electron 2 rotate in opposite directions; whereas, for triplet states, the relative motion of the spin currents is in the same direction. In the triplet state, the electrons are spin-unpaired, but due to the superposition of the excited state source currents and the current corresponding to the spin-unpairing transition to create the triplet state, the spin-spin force is paramagnetic. The angular momentum corresponding to the excited states is $\hbar$ and the angular momentum change corresponding to the spin-flip or 180° rotation of the Larmor precession is also $\hbar$ as given in the Magnetic Parameters of the Electron (Bohr Magneton) section of Ref. [1]. The maximum projection of the angular momentum of a constant function onto a defined axis (Eq. (1.74a)) is $$S_\perp = \hbar \sin\frac{\pi}{3} = \pm\sqrt{\frac{3}{4}} \hbar i_{y_R} \qquad (9.30)$$

Following the derivation for Eq. (7.15) using Eq. (9.30) and a magnetic moment of $2\mu_B$ corresponding to a total angular momentum of the excited triplet state of $2\hbar$, the spin-spin force for electron 2 is twice that of the singlet states:

$$\frac{m_e v^2}{r_2} = \frac{\hbar^2}{m_e r_2^3} = \frac{1}{n}\frac{e^2}{4\pi\varepsilon_o r_2^2} + 2\frac{2}{3}\frac{1}{n}\frac{\hbar^2}{2m_e r_2^3}\sqrt{s(s+1)} \qquad (9.31)$$

With $s = \frac{1}{2}$, $$r_2 = \left[n - \frac{2\sqrt{\frac{3}{4}}}{3}\right]a_{He} \quad n = 2, 3, 4, \ldots \qquad (9.32)$$

The excited-state energy is the energy stored in the electric field, $E_{ele}$, given by Eq. (9.12) where $r_2$ is given by Eq. (9.32). The energies of the various triplet excited states of helium with $l=0$ appear in TABLE IV.

Using $r_2$ (Eq. (9.32)), $r_1$ can be solved using the equal and opposite magnetic force of electron 2 on electron 1 and the central Coulombic force corresponding to the nuclear charge of 2e. Using Eq. (9.31), the force balance between the centrifugal and electric and magnetic forces is $$\frac{m_e v^2}{r_1} = \frac{\hbar^2}{m_e r_1^3} = \frac{2e^2}{4\pi\varepsilon_o r_1^2} - \frac{2}{3n}\frac{\hbar^2}{m_e r_2^3}\sqrt{s(s+1)} \qquad (9.33)$$

With $s = \frac{1}{2}$, $$r_1^3 - \left(\frac{6n}{\sqrt{3}}r_2^3\right)r_1 + \frac{3n}{\sqrt{3}}r_2^3 = 0 \qquad (9.34)$$

$n = 2, 3, 4, \ldots$ where $r_2$ is given by Eq. (9.32) and $r_1$ and $r_2$ are in units of $a_{He}$. To obtain the solution of cubic Eq. (9.34), let $$g = \frac{3n}{\sqrt{3}}r_2^3 \qquad (9.35)$$

Then, Eq. (9.34) becomes $$r_1^3 - 2gr_1 + g = 0 \quad n=2, 3, 4, \ldots \qquad (9.36)$$

Using Eqs. (9.16-9.29), the real and physical root is $$r_1 = r_{13} = -\sqrt{\frac{2}{3}}g\left(\cos\frac{\theta}{3} - \sqrt{3}\sin\frac{\theta}{3}\right) \qquad (9.37)$$

TABLE IV

Calculated and experimental energies of He I triplet excited states with $l = 0$ ($1s^2 \to 1s^1(ns)^1$).

| n | $r_1$ ($a_{He}$)[a] | $r_2$ ($a_{He}$)[b] | Term Symbol | $E_{ele}$ CQM He I Energy Levels[c] (eV) | NIST He I Energy Levels[d] (eV) | Difference CQM − NIST (eV) | Relative Difference[e] (CQM − NIST) |
|---|---|---|---|---|---|---|---|
| 2 | 0.506514 | 1.42265 | 1s2s $^3$S | −4.78116 | −4.76777 | −0.01339 | 0.00281 |
| 3 | 0.500850 | 2.42265 | 1s3s $^3$S | −1.87176 | −1.86892 | −0.00284 | 0.00152 |
| 4 | 0.500225 | 3.42265 | 1s4s $^3$S | −0.99366 | −0.99342 | −0.00024 | 0.00024 |
| 5 | 0.500083 | 4.42265 | 1s5s $^3$S | −0.61519 | −0.61541 | 0.00022 | −0.00036 |
| 6 | 0.500038 | 5.42265 | 1s6s $^3$S | −0.41812 | −0.41838 | 0.00026 | −0.00063 |
| 7 | 0.500019 | 6.42265 | 1s7s $^3$S | −0.30259 | −0.30282 | 0.00023 | −0.00077 |
| 8 | 0.500011 | 7.42265 | 1s8s $^3$S | −0.22909 | −0.22928 | 0.00019 | −0.00081 |
| 9 | 0.500007 | 8.42265 | 1s9s $^3$S | −0.17946 | −0.17961 | 0.00015 | −0.00083 |
| 10 | 0.500004 | 9.42265 | 1s10s $^3$S | −0.14437 | −0.1445 | 0.00013 | −0.00087 |
| 11 | 0.500003 | 10.42265 | 1s11s $^3$S | −0.11866 | −0.11876 | 0.00010 | −0.00087 |
|  |  |  |  |  | Avg. | −0.00152 | −0.00006 |

[a] Radius of the inner electron 1 from Eq. (9.37).
[b] Radius of the outer electron 2 from Eq. (9.32).
[c] Classical quantum mechanical (CQM) calculated energy levels given by the electric energy (Eq. (9.12)).
[d] Experimental NIST levels [34] with the ionization potential defined as zero.
[e] (Theoretical−Experimental)/Experimental.

3.C Singlet Excited States with l≠0

With l≠0, the electron source current in the excited state is the sum of constant and time-dependent functions where the latter, given by Eq. (1.65), travels about the z-axis. The current due to the time dependent term of Eq. (1.65) corresponding to p, d, f, etc. orbitals is $$J = \frac{\omega_n}{2\pi} \frac{e}{4\pi r_n^2} N[\delta(r-r_n)]\text{Re}\{Y_\ell^m(\theta,\phi)\}[u(t) \times r] \quad (9.38)$$

$$= \frac{\omega_n}{2\pi} \frac{e}{4\pi r_n^2} N'[\delta(r-r_n)](P_\ell^m(\cos\theta)\cos(m\phi + \omega_n' t))[u \times r]$$

$$= \frac{\omega_n}{2\pi} \frac{e}{4\pi r_n^2} N'[\delta(r-r_n)](P_\ell^m(\cos\theta)\cos(m\phi + \omega_n' t))\sin\theta \hat{\phi}$$

where to keep the form of the spherical harmonic as a traveling wave about the z-axis, $\dot{\omega}_n = m\omega_n$ and N and N' are normalization constants. The vectors are defined as $$\hat{\phi} = \frac{\hat{u} \times \hat{r}}{|\hat{u} \times \hat{r}|} = \frac{\hat{u} \times \hat{r}}{\sin\theta}; \hat{u} = \hat{z} = \text{orbital axis} \quad (9.39)$$

$$\hat{\theta} = \hat{\phi} \times \hat{r} \quad (9.40)$$

"^" denotes the unit vectors $$\hat{u} \equiv \frac{u}{|u|},$$

non-unit vectors are designed in bold, and the current function is normalized.

Jackson [35] gives the general multipole field solution to Maxwell's equations in a source-free region of empty space with the assumption of a time dependence $e^{i\omega_n t}$:

$$B = \sum_{\ell,m} \left[ a_E(\ell,m) f_\ell(kr) X_{\ell,m} - \frac{i}{k} a_M(\ell,m) \nabla \times g_\ell(kr) X_{\ell,m} \right] \quad (9.41)$$

$$E = \sum_{\ell,m} \left[ \frac{i}{k} a_E(\ell,m) \nabla \times f_\ell(kr) X_{\ell,m} + a_M(\ell,m) g_\ell(kr) X_{\ell,m} \right]$$

where the cgs units used by Jackson are retained in this section. The radial functions $f_\ell(kr)$ and $g_\ell(kr)$ are of the form:

$$g_\ell(kr) = A_\ell^{(1)} h_\ell^{(1)} + A_\ell^{(2)} h_\ell^{(2)} \quad (9.42)$$

$X_{l,m}$ is the vector spherical harmonic defined by $$X_{\ell,m}(\theta,\phi) = \frac{1}{\sqrt{\ell(\ell+1)}} L Y_{\ell,m}(\theta,\phi) \quad (9.43)$$

where $$L = \frac{1}{i}(r \times \nabla) \quad (9.43)$$

The coefficients $\alpha_E(l,m)$ and $\alpha_M(l,m)$ of Eq. (9.41) specify the amounts of electric (l,m) multipole and magnetic (l,m) multipole fields, and are determined by sources and boundary conditions as are the relative proportions in Eq. (9.42). Jackson gives the result of the electric and magnetic coefficients from the sources as $$\alpha_E(\ell,m) = \quad (9.45)$$
$$\frac{4\pi k^2}{i\sqrt{\ell(\ell+1)}} \int Y_\ell^{m*} \left\{ \rho \frac{\delta}{\delta r}[rj_\ell(kr)] + \frac{ik}{c}(r \cdot J) j_\ell(kr) - ik\nabla \cdot (r \times M) j_\ell(kr) \right\} d^3x$$

and $$\alpha_M(\ell,m) = \frac{-4\pi k^2}{\sqrt{\ell(\ell+1)}} \int j_\ell(kr) y_\ell^{m*} L \cdot \left( \frac{J}{c} + \nabla \times M \right) d^3x \quad (9.46)$$

respectively, where the distribution of charge ρ(x,t), current J(x,t), and intrinsic magnetization M(x,t) are harmonically varying sources: $\rho(x)e^{-\omega_n t}$, $J(x)e^{-\omega_n t}$, and $M(x)e^{-\omega j}$. From Eq. (9.38), the charge and intrinsic magnetization terms are zero. Since the source dimensions are very small compared to a wavelength ($kr_{max} \ll 1$), the small argument limit can be used to give the magnetic multipole coefficient $\alpha_M(l,m)$ as $$\alpha_M(\ell,m) = \quad (9.47)$$
$$\frac{-4\pi k^{\ell+2}}{(2\ell+1)!!}\left(\frac{\ell+1}{\ell}\right)^{1/2}(M_{\ell m} + M'_{\ell m}) = \frac{-4\pi k^{\ell+2}}{\frac{(2\ell+1)!}{2^n n!}}(M_{\ell m} + M'_{\ell m})$$

where the magnetic multipole moments are $$M_{\ell m} = -\frac{1}{\ell+1} \int r^\ell Y_{\ell m}^* \nabla \cdot \left( \frac{r \times J}{c} \right) d^3x \quad (9.48)$$

$$M'_{\ell m} = -\int r^\ell Y_{\ell m}^* \nabla \cdot M d^3x$$

From Eq. (1.108), the geometrical factor of the surface current-density function of the orbitsphere about the z-axis is $$\left(\frac{2}{3}\right)^{-1}.$$

Using the geometrical factor, Eqs. (9.47-9.48), and Eqs. (16.101) and (16.102) of Jackson [36], the multipole coefficient $\alpha_{Mag}(l,m)$ of the magnetic force of Eq. (7.15) is $$\alpha_{Mag}(\ell,m) = \frac{\frac{3}{2}}{(2\ell+1)!!} \frac{1}{\ell+2} \left(\frac{\ell+1}{\ell}\right)^{1/2} \quad (9.49)$$

For singlet states with l≠0, a minimum energy is achieved with conservation of the photon's angular momentum of $\hbar$ when the magnetic moments of the corresponding angular momenta relative to the electron velocity (and corresponding Lorentzian forces given by Eq. (7.5)) superimpose negatively such that the spin component is radial ($i_r$-direction) and the orbital component is central ($-i_r$-direction). The amplitude of the orbital angular momentum $L_{rotational\ orbital}$, given by Eq. (1.96b) is $$L = I\omega i_z = \hbar\left[\frac{\ell(\ell+1)}{\ell^2 + 2\ell + 1}\right]^{\frac{1}{2}} = \hbar\sqrt{\frac{\ell}{\ell+1}} \quad (9.50)$$

Thus, using Eqs. (7.15), (9.8), and (9.49-9.50), the magnetic force between the two electrons is $$F_{Mag} = -\frac{1}{n}\frac{\frac{3}{2}}{(2\ell+1)!!}\frac{1}{\ell+2}\left(\frac{\ell+1}{\ell}\right)^{1/2}\frac{1}{2}\frac{\hbar^2}{m_e r^3}\left(\sqrt{s(s+1)} - \sqrt{\frac{\ell}{\ell+1}}\right) \quad (9.51)$$

and the force balance equation from Eq. (7.18) which achieves the condition that the sum of the mechanical momentum and electromagnetic momentum is conserved as given in Sections 6.6, 12.10, and 17.3 of Jackson [37] is $$\frac{m_e v^2}{r_2} = \frac{\hbar^2}{m_e r_2^3} = \frac{1}{n}\frac{e^2}{4\pi\varepsilon_o r_2^2} - \frac{1}{n}\frac{\frac{3}{2}}{(2\ell+1)!!}\left(\frac{\ell+1}{\ell}\right)^{1/2} \frac{1}{\ell+2}\frac{1}{2}\frac{\hbar^2}{m_e r^3}\left(\sqrt{s(s+1)} - \sqrt{\frac{\ell}{\ell+1}}\right) \quad (9.52)$$

With $s = \frac{1}{2}$, $$r_2 = \left[n + \frac{\frac{3}{4}}{(2\ell+1)!!}\frac{1}{\ell+2}\left(\frac{\ell+1}{\ell}\right)^{1/2}\left(\sqrt{\frac{3}{4}} - \sqrt{\frac{\ell}{\ell+1}}\right)\right]a_{He} \quad (9.53)$$

$n = 2, 3, 4, \ldots$

The excited-state energy is the energy stored in the electric field, $E_{ele}$, given by Eq. (9.12) where $r_2$ is given by Eq. (9.53). The energies of the various singlet excited states of helium with $l \neq 0$ appear in TABLE V.

Using $r_2$ (Eq. (9.53), $r_1$ can be solved using the equal and opposite magnetic force of electron 2 on electron 1 and the central Coulombic force corresponding to the nuclear charge of 2e. Using Eq. (9.52), the force balance between the centrifugal and electric and magnetic forces is $$\frac{m_e v^2}{r_1} = \frac{\hbar^2}{m_e r_1^3} = \frac{2e^2}{4\pi\varepsilon_o r_1^2} + \frac{1}{n}\frac{\frac{3}{2}}{(2\ell+1)!!}\left(\frac{\ell+1}{\ell}\right)^{1/2} \frac{1}{\ell+2}\frac{1}{2}\frac{\hbar^2}{m_e r_2^3}\left(\sqrt{s(s+1)} - \sqrt{\frac{\ell}{\ell+1}}\right) \quad (9.54)$$

With $s = \frac{1}{2}$,

-continued $$r_1^3 + \frac{n 8 r_1 r_2^3}{3\left(\sqrt{\frac{3}{4}} - \sqrt{\frac{\ell}{\ell+1}}\right)}(2\ell+1)!!\left(\frac{\ell}{\ell+1}\right)^{1/2}(\ell+2) - \frac{n 4 r_2^3}{3\left(\sqrt{\frac{3}{4}} - \sqrt{\frac{\ell}{\ell+1}}\right)}(2\ell+1)!!\left(\frac{\ell}{\ell+1}\right)^{1/2}(\ell+2) = 0 \quad (9.55)$$

$n = 2, 3, 4, \ldots$ where $r_2$ is given by Eq. (9.53) and $r_1$ and $r_2$ are in units of $a_{He}$. To obtain the solution of cubic Eq. (9.55), let $$g = -\frac{n 4 r_2^3}{3\left(\sqrt{\frac{3}{4}} - \sqrt{\frac{\ell}{\ell+1}}\right)}(2\ell+1)!!\left(\frac{\ell}{\ell+1}\right)^{1/2}(\ell+2) \quad (9.56)$$

Then, Eq. (9.55) becomes $$r_1^3 - 2gr_1 + g = 0 \quad n = 2, 3, 4, \ldots \quad (9.57)$$

Three distinct cases arise depending on the value of l. For l=1 or l=2, g of Eq. (9.56) is negative and A and B of Eqs. (9.20) and (9.21), respectively, are real:

$$A = \sqrt[3]{-\frac{g}{2}}\sqrt[3]{1 + \sqrt{1 - \frac{32}{27}g}} \quad (9.58)$$

and $$B = -\sqrt[3]{-\frac{g}{2}}\sqrt[3]{1 + \sqrt{1 - \frac{32}{27}g} - 1} \quad (9.59)$$

The only real root is $$r_1 = \quad (9.60)$$

$$r_{11} = \sqrt[3]{-\frac{g}{2}}\left\{\sqrt[3]{1 + \sqrt{1 - \frac{32}{27}g}} - \sqrt[3]{\sqrt{1 - \frac{32}{27}g} - 1}\right\}$$

while $r_{12}$ and $r_{13}$ are complex conjugates. When l=3 the magnetic force term (2nd term on RHS) of Eq. (9.52) is zero, and the force balance trivially gives $$r_1 = 0.5 a_{He} \quad (9.61)$$

When l=4, 5, 6 ... all three roots are real, but, the physical root is $r_{13}$. In this case, note that $n \geq 5$, $l \geq 4$; so, the factor g of Eq. (9.56) is large (>$10^8$). Expanding $r_{13}$ for large values of g gives $$r_1 = r_{13} = \frac{1}{2} + \frac{1}{16g} + O(g^{-3/2}) \quad (9.62)$$

TABLE V

Calculated and experimental energies of He I singlet excited states with l ≠ 0.

| n | l | $r_1$ $(a_{He})$[a] | $r_2$ $(a_{He})$[b] | Term Symbol | $E_{ele}$ CQM He I Energy Levels[c] (eV) | NIST He I Energy Levels[d] (eV) | Difference CQM − NIST (eV) | Relative Difference[e] (CQM − NIST) |
|---|---|---|---|---|---|---|---|---|
| 2 | 1 | 0.499929 | 2.01873 | 1s2p $^1P^0$ | −3.36941 | −3.36936 | −0.0000477 | 0.0000141 |
| 3 | 2 | 0.499999 | 3.00076 | 1s3d $^1D$ | −1.51116 | −1.51331 | 0.0021542 | −0.0014235 |
| 3 | 1 | 0.499986 | 3.01873 | 1s3p $^1P^0$ | −1.50216 | −1.50036 | −0.0017999 | 0.0011997 |
| 4 | 2 | 0.500000 | 4.00076 | 1s4d $^1D$ | −0.85008 | −0.85105 | 0.0009711 | −0.0011411 |
| 4 | 3 | 0.500000 | 4.00000 | 1s4f $^1F^0$ | −0.85024 | −0.85037 | 0.0001300 | −0.0001529 |
| 4 | 1 | 0.499995 | 4.01873 | 1s4p $^1P^0$ | −0.84628 | −0.84531 | −0.0009676 | 0.0011446 |
| 5 | 2 | 0.500000 | 5.00076 | 1s5d $^1D$ | −0.54407 | −0.54458 | 0.0005089 | −0.0009345 |
| 5 | 3 | 0.500000 | 5.00000 | 1s5f $^1F^0$ | −0.54415 | −0.54423 | 0.0000764 | −0.0001404 |
| 5 | 4 | 0.500000 | 5.00000 | 1s5g $^1G$ | −0.54415 | −0.54417 | 0.0000159 | −0.0000293 |
| 5 | 1 | 0.499998 | 5.01873 | 1s5p $^1P^0$ | −0.54212 | −0.54158 | −0.0005429 | 0.0010025 |
| 6 | 2 | 0.500000 | 6.00076 | 1s6d $^1D$ | −0.37784 | −0.37813 | 0.0002933 | −0.0007757 |
| 6 | 3 | 0.500000 | 6.00000 | 1s6f $^1F^0$ | −0.37788 | −0.37793 | 0.0000456 | −0.0001205 |
| 6 | 4 | 0.500000 | 6.00000 | 1s6g $^1G$ | −0.37788 | −0.37789 | 0.0000053 | −0.0000140 |
| 6 | 5 | 0.500000 | 6.00000 | 1s6h $^1H^0$ | −0.37788 | −0.37788 | −0.0000045 | 0.0000119 |
| 6 | 1 | 0.499999 | 6.01873 | 1s6p $^1P^0$ | −0.37671 | −0.37638 | −0.0003286 | 0.0008730 |
| 7 | 2 | 0.500000 | 7.00076 | 1s7d $^1D$ | −0.27760 | −0.27779 | 0.0001907 | −0.0006864 |
| 7 | 3 | 0.500000 | 7.00000 | 1s7f $^1F^0$ | −0.27763 | −0.27766 | 0.0000306 | −0.0001102 |
| 7 | 4 | 0.500000 | 7.00000 | 1s7g $^1G$ | −0.27763 | −0.27763 | 0.0000004 | −0.0000016 |
| 7 | 5 | 0.500000 | 7.00000 | 1s7h $^1H^0$ | −0.27763 | −0.27763 | 0.0000006 | −0.0000021 |
| 7 | 6 | 0.500000 | 7.00000 | 1s7i $^1I$ | −0.27763 | −0.27762 | −0.0000094 | 0.0000338 |
| 7 | 1 | 0.500000 | 7.01873 | 1s7p $^1P^0$ | −0.27689 | −0.27667 | −0.0002186 | 0.0007900 |
|   |   |   |   | Avg. |   |   | 0.0000240 | −0.0000220 |

[a] Radius of the inner electron 1 from Eq. (9.60) for l = 1 or l = 2, Eq. (9.61) for l = 3, and Eq. (9.62) for l = 4, 5, 6 ....
[b] Radius of the outer electron 2 from Eq. (9.53).
[c] Classical quantum mechanical (CQM) calculated energy levels given by the electric energy (Eq. (9.12)).
[d] Experimental NIST levels [34] with the ionization potential defined as zero.
[e] (Theoretical-Experimental)/Experimental.

3.D Triplet Excited States with l≠0

For triplet states with l≠0, a minimum energy is achieved with conservation of the photon's angular momentum of $\hbar$ when the magnetic moments of the corresponding angular momenta superimpose negatively such that the spin component is central and the orbital component is radial. Furthermore, as given for the triplet states with l=0, the spin component in Eqs. (9.51) and (9.52) is doubled. Thus, the force balance equation is given by $$\frac{m_e v^2}{r_2} = \frac{\hbar^2}{m_e r_2^3} = \frac{1}{n}\frac{e^2}{4\pi\varepsilon_o r_2^2} + \frac{1}{n}\frac{\frac{3}{2}}{(2\ell+1)!!}\left(\frac{\ell+1}{\ell}\right)^{1/2} \quad (9.63)$$

$$\frac{1}{\ell+2}\frac{1}{2}\frac{\hbar^2}{m_e r^3}\left(2\sqrt{s(s+1)} - \sqrt{\frac{\ell}{\ell+1}}\right)$$

With $s = \frac{1}{2}$, $$r_2 = \left[n - \frac{\frac{3}{4}}{(2\ell+1)!!}\frac{1}{\ell+2}\left(\frac{\ell+1}{\ell}\right)^{1/2}\left(2\sqrt{\frac{3}{4}} - \sqrt{\frac{\ell}{\ell+1}}\right)\right]a_{He} \quad (9.64)$$

$n = 2, 3, 4, \ldots$

The excited-state energy is the energy stored in the electric field, $E_{ele}$, given by Eq. (9.12) where $r_2$ is given by Eq. (9.64). The energies of the various triplet excited states of helium with l≠0 appear in TABLE VI.

Using $r_2$ (Eq. (9.64)), $r_1$ can be solved using the equal and opposite magnetic force of electron 2 on electron 1 and the central Coulombic force corresponding to the nuclear charge of 2e. Using Eq. (9.63), the force balance between the centrifugal and electric and magnetic forces is $$\frac{m_e v^2}{r_1} = \frac{\hbar^2}{m_e r_1^3} = \frac{2e^2}{4\pi\varepsilon_o r_1^2} - \frac{1}{n}\frac{\frac{3}{2}}{(2\ell+1)!!}\left(\frac{\ell+1}{\ell}\right)^{1/2} \quad (9.65)$$

$$\frac{1}{\ell+2}\frac{1}{2}\frac{\hbar^2}{m_e r^3}\left(2\sqrt{s(s+1)} - \sqrt{\frac{\ell}{\ell+1}}\right)$$

With $s = \frac{1}{2}$, $$r_1^3 - \frac{n 8 r_1 r_2^3}{3\left(\sqrt{\frac{3}{4}} - \sqrt{\frac{\ell}{\ell+1}}\right)}(2\ell+1)!!\left(\frac{\ell}{\ell+1}\right)^{1/2}(\ell+2) + \quad (9.66)$$

$$\frac{n 4 r_2^3}{3\left(\sqrt{\frac{3}{4}} - \sqrt{\frac{\ell}{\ell+1}}\right)}(2\ell+1)!!\left(\frac{\ell}{\ell+1}\right)^{1/2}(\ell+2) = 0$$

$n = 2, 3, 4, \ldots$ where $r_2$ is given by Eq. (9.64) and $r_1$ and $r_2$ are in units of $a_{He}$. To obtain the solution of cubic Eq. (9.66), let $$g = \frac{n4r_2^3}{3\left(\sqrt{3} - \sqrt{\frac{\ell}{\ell+1}}\right)}(2\ell+1)!!\left(\frac{\ell}{\ell+1}\right)^{1/2}(\ell+2) \quad (9.67)$$

Then, Eq. (9.66) becomes $$r_1^3 - 2gr_1 + g = 0 \quad n=2, 3, 4, \ldots \quad (9.68)$$

Using Eqs. (9.16-9.29), the real and physical root is $$r_1 = r_{13} = -\sqrt{\frac{2}{3}g}\left(\cos\frac{\theta}{3} - \sqrt{3}\sin\frac{\theta}{3}\right) \quad (9.69)$$

TABLE VI

Calculated and experimental energies of He I triplet excited states with $l \neq 0$.

| n | l | $r_1$ $(a_{He})^a$ | $r_2$ $(a_{He})^b$ | Term Symbol | $E_{ele}$ CQM He I Energy Levels$^c$ (eV) | NIST He I Energy Levels$^d$ (eV) | Difference CQM − NIST (eV) | Relative Difference$^e$ (CQM − NIST) |
|---|---|---|---|---|---|---|---|---|
| 2 | 1 | 0.500571 | 1.87921 | 1s2p $^3P^o_2$ | −3.61957 | −3.6233 | 0.0037349 | −0.0010308 |
| 2 | 1 | 0.500571 | 1.87921 | 1s2p $^3P^o_1$ | −3.61957 | −3.62329 | 0.0037249 | −0.0010280 |
| 2 | 1 | 0.500571 | 1.87921 | 1s2p $^3P^o_0$ | −3.61957 | −3.62317 | 0.0036049 | −0.0009949 |
| 3 | 1 | 0.500105 | 2.87921 | 1s3p $^3P^o_2$ | −1.57495 | −1.58031 | 0.0053590 | −0.0033911 |
| 3 | 1 | 0.500105 | 2.87921 | 1s3p $^3P^o_1$ | −1.57495 | −1.58031 | 0.0053590 | −0.0033911 |
| 3 | 1 | 0.500105 | 2.87921 | 1s3p $^3P^o_0$ | −1.57495 | −1.58027 | 0.0053190 | −0.0033659 |
| 3 | 2 | 0.500011 | 2.98598 | 1s3d $^3D_3$ | −1.51863 | −1.51373 | −0.0049031 | 0.0032391 |
| 3 | 2 | 0.500011 | 2.98598 | 1s3d $^3D_2$ | −1.51863 | −1.51373 | −0.0049031 | 0.0032391 |
| 3 | 2 | 0.500011 | 2.98598 | 1s3d $^3D_1$ | −1.51863 | −1.51373 | −0.0049031 | 0.0032391 |
| 4 | 1 | 0.500032 | 3.87921 | 1s4p $^3P^o_2$ | −0.87671 | −0.87949 | 0.0027752 | −0.0031555 |
| 4 | 1 | 0.500032 | 3.87921 | 1s4p $^3P^o_1$ | −0.87671 | −0.87949 | 0.0027752 | −0.0031555 |
| 4 | 1 | 0.500032 | 3.87921 | 1s4p $^3P^o_0$ | −0.87671 | −0.87948 | 0.0027652 | −0.0031442 |
| 4 | 2 | 0.500003 | 3.98598 | 1s4d $^3D_3$ | −0.85323 | −0.85129 | −0.0019398 | 0.0022787 |
| 4 | 2 | 0.500003 | 3.98598 | 1s4d $^3D_2$ | −0.85323 | −0.85129 | −0.0019398 | 0.0022787 |
| 4 | 2 | 0.500003 | 3.98598 | 1s4d $^3D_1$ | −0.85323 | −0.85129 | −0.0019398 | 0.0022787 |
| 4 | 3 | 0.500000 | 3.99857 | 1s4f $^3F^o_3$ | −0.85054 | −0.85038 | −0.0001638 | 0.0001926 |
| 4 | 3 | 0.500000 | 3.99857 | 1s4f $^3F^o_4$ | −0.85054 | −0.85038 | −0.0001638 | 0.0001926 |
| 4 | 3 | 0.500000 | 3.99857 | 1s4f $^3F^o_2$ | −0.85054 | −0.85038 | −0.0001638 | 0.0001926 |
| 5 | 1 | 0.500013 | 4.87921 | 1s5p $^3P^o_2$ | −0.55762 | −0.55916 | 0.0015352 | −0.0027456 |
| 5 | 1 | 0.500013 | 4.87921 | 1s5p $^3P^o_1$ | −0.55762 | −0.55916 | 0.0015352 | −0.0027456 |
| 5 | 1 | 0.500013 | 4.87921 | 1s5p $^3P^o_0$ | −0.55762 | −0.55915 | 0.0015252 | −0.0027277 |
| 5 | 2 | 0.500001 | 4.98598 | 1s5d $^3D_3$ | −0.54568 | −0.54472 | −0.0009633 | 0.0017685 |
| 5 | 2 | 0.500001 | 4.98598 | 1s5d $^3D_2$ | −0.54568 | −0.54472 | −0.0009633 | 0.0017685 |
| 5 | 2 | 0.500001 | 4.98598 | 1s5d $^3D_1$ | −0.54568 | −0.54472 | −0.0009633 | 0.0017685 |
| 5 | 3 | 0.500000 | 4.99857 | 1s5f $^3F^o_3$ | −0.54431 | −0.54423 | −0.0000791 | 0.0001454 |
| 5 | 3 | 0.500000 | 4.99857 | 1s5f $^3F^o_4$ | −0.54431 | −0.54423 | −0.0000791 | 0.0001454 |
| 5 | 3 | 0.500000 | 4.99857 | 1s5f $^3F^o_2$ | −0.54431 | −0.54423 | −0.0000791 | 0.0001454 |
| 5 | 4 | 0.500000 | 4.99988 | 1s5g $^3G_4$ | −0.54417 | −0.54417 | 0.0000029 | −0.0000054 |
| 5 | 4 | 0.500000 | 4.99988 | 1s5g $^3G_5$ | −0.54417 | −0.54417 | 0.0000029 | −0.0000054 |
| 5 | 4 | 0.500000 | 4.99988 | 1s5g $^3G_3$ | −0.54417 | −0.54417 | 0.0000029 | −0.0000054 |
| 6 | 1 | 0.500006 | 5.87921 | 1s6p $^3P^o_2$ | −0.38565 | −0.38657 | 0.0009218 | −0.0023845 |
| 6 | 1 | 0.500006 | 5.87921 | 1s6p $^3P^o_1$ | −0.38565 | −0.38657 | 0.0009218 | −0.0023845 |
| 6 | 1 | 0.500006 | 5.87921 | 1s6p $^3P^o_0$ | −0.38565 | −0.38657 | 0.0009218 | −0.0023845 |
| 6 | 2 | 0.500001 | 5.98598 | 1s6d $^3D_3$ | −0.37877 | −0.37822 | −0.0005493 | 0.0014523 |
| 6 | 2 | 0.500001 | 5.98598 | 1s6d $^3D_2$ | −0.37877 | −0.37822 | −0.0005493 | 0.0014523 |
| 6 | 2 | 0.500001 | 5.98598 | 1s6d $^3D_1$ | −0.37877 | −0.37822 | −0.0005493 | 0.0014523 |
| 6 | 3 | 0.500000 | 5.99857 | 1s6f $^3F^o_3$ | −0.37797 | −0.37793 | −0.0000444 | 0.0001176 |
| 6 | 3 | 0.500000 | 5.99857 | 1s6f $^3F^o_4$ | −0.37797 | −0.37793 | −0.0000444 | 0.0001176 |
| 6 | 3 | 0.500000 | 5.99857 | 1s6f $^3F^o_2$ | −0.37797 | −0.37793 | −0.0000444 | 0.0001176 |
| 6 | 4 | 0.500000 | 5.99988 | 1s6g $^3G_4$ | −0.37789 | −0.37789 | −0.0000023 | 0.0000060 |
| 6 | 4 | 0.500000 | 5.99988 | 1s6g $^3G_5$ | −0.37789 | −0.37789 | −0.0000023 | 0.0000060 |
| 6 | 4 | 0.500000 | 5.99988 | 1s6g $^3G_3$ | −0.37789 | −0.37789 | −0.0000023 | 0.0000060 |
| 6 | 5 | 0.500000 | 5.99999 | 1s6h $^3H^o_4$ | −0.37789 | −0.37788 | −0.0000050 | 0.0000133 |
| 6 | 5 | 0.500000 | 5.99999 | 1s6h $^3H^o_5$ | −0.37789 | −0.37788 | −0.0000050 | 0.0000133 |
| 6 | 5 | 0.500000 | 5.99999 | 1s6h $^3H^o_6$ | −0.37789 | −0.37788 | −0.0000050 | 0.0000133 |
| 7 | 1 | 0.500003 | 6.87921 | 1s7p $^3P^o_2$ | −0.28250 | −0.28309 | 0.0005858 | −0.0020692 |
| 7 | 1 | 0.500003 | 6.87921 | 1s7p $^3P^o_1$ | −0.28250 | −0.28309 | 0.0005858 | −0.0020692 |
| 7 | 1 | 0.500003 | 6.87921 | 1s7p $^3P^o_0$ | −0.28250 | −0.28309 | 0.0005858 | −0.0020692 |
| 7 | 2 | 0.500000 | 6.98598 | 1s7d $^3D_3$ | −0.27819 | −0.27784 | −0.0003464 | 0.0012468 |
| 7 | 2 | 0.500000 | 6.98598 | 1s7d $^3D_2$ | −0.27819 | −0.27784 | −0.0003464 | 0.0012468 |
| 7 | 2 | 0.500000 | 6.98598 | 1s7d $^3D_1$ | −0.27819 | −0.27784 | −0.0003464 | 0.0012468 |
| 7 | 3 | 0.500000 | 6.99857 | 1s7f $^3F^o_3$ | −0.27769 | −0.27766 | −0.0000261 | 0.0000939 |
| 7 | 3 | 0.500000 | 6.99857 | 1s7f $^3F^o_4$ | −0.27769 | −0.27766 | −0.0000261 | 0.0000939 |
| 7 | 3 | 0.500000 | 6.99857 | 1s7f $^3F^o_2$ | −0.27769 | −0.27766 | −0.0000261 | 0.0000939 |
| 7 | 4 | 0.500000 | 6.99988 | 1s7g $^3G_4$ | −0.27763 | −0.27763 | −0.0000043 | 0.0000155 |
| 7 | 4 | 0.500000 | 6.99988 | 1s7g $^3G_5$ | −0.27763 | −0.27763 | −0.0000043 | 0.0000155 |
| 7 | 4 | 0.500000 | 6.99988 | 1s7g $^3G_3$ | −0.27763 | −0.27763 | −0.0000043 | 0.0000155 |

TABLE VI-continued

Calculated and experimental energies of He I triplet excited states with l ≠ 0.

| n | l | $r_1$ $(a_{He})$ [a] | $r_2$ $(a_{He})$ [b] | Term Symbol | $E_{ele}$ CQM He I Energy Levels [c] (eV) | NIST He I Energy Levels [d] (eV) | Difference CQM − NIST (eV) | Relative Difference [e] (CQM − NIST) |
|---|---|---|---|---|---|---|---|---|
| 7 | 5 | 0.500000 | 6.99999 | 1s7h $^3H^o_5$ | −0.27763 | −0.27763 | 0.0000002 | −0.0000009 |
| 7 | 5 | 0.500000 | 6.99999 | 1s7h $^3H^o_6$ | −0.27763 | −0.27763 | 0.0000002 | −0.0000009 |
| 7 | 5 | 0.500000 | 6.99999 | 1s7h $^3H^o_4$ | −0.27763 | −0.27763 | 0.0000002 | −0.0000009 |
| 7 | 6 | 0.500000 | 7.00000 | 1s7 $i^3I_5$ | −0.27763 | −0.27762 | −0.0000094 | 0.0000339 |
| 7 | 6 | 0.500000 | 7.00000 | 1s7i $^3I6$ | −0.27763 | −0.27762 | −0.0000094 | 0.0000339 |
| 7 | 6 | 0.500000 | 7.00000 | 1s7i $^3I_7$ | −0.27763 | −0.27762 | −0.0000094 | 0.0000339 |
|   |   |         |         |            |          | Avg. | 0.0002768 | −0.0001975 |

[a] Radius of the inner electron 1 from Eq. (9.69).
[b] Radius of the outer electron 2 from Eq. (9.64).
[c] Classical quantum mechanical (CQM) calculated energy levels given by the electric energy (Eq. (9.12)).
[d] Experimental NIST levels [34] with the ionization potential defined as zero.
[e] (Theoretical-Experimental)/Experimental.

3.E All Excited He I States

Figure 6:
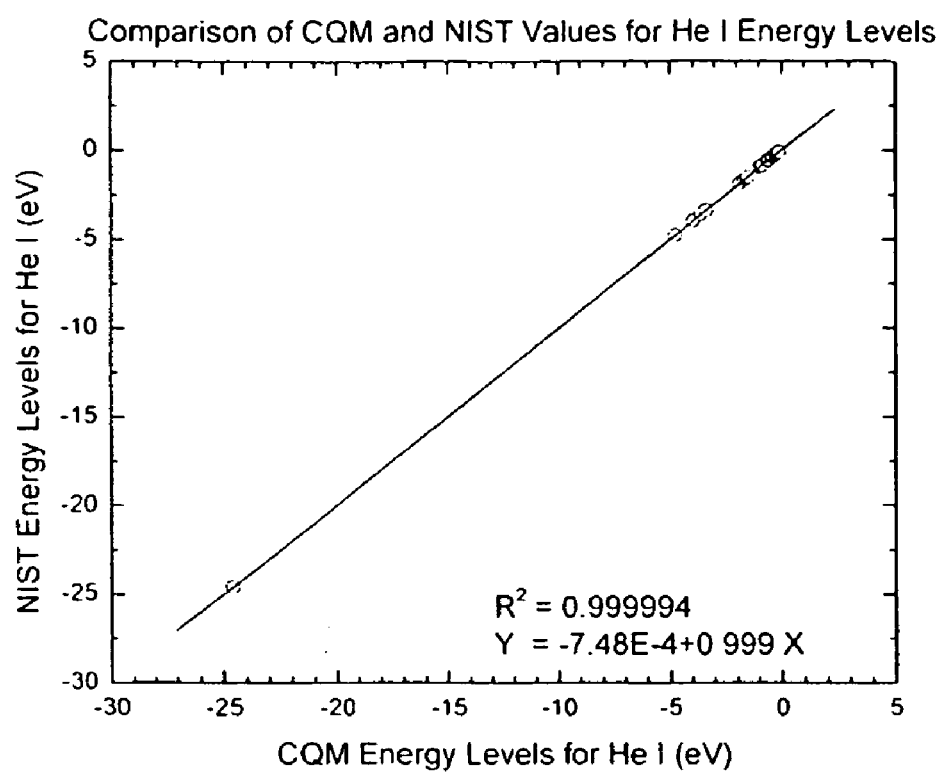
FIG. 6 shows a plot of the predicted and experimental energies of levels assigned by NIST.

The combined energies of the various states of helium appear in TABLE VII. A plot of the predicted and experimental energies of levels assigned by NIST [34] appears in FIG. 6. For over 100 states, the r-squared value is 0.999994, and the typical average relative difference is about 5 significant figures which is within the error of the experimental data. The agreement is remarkable.

The hydrino states given in the Hydrino Theory—Black-Light Process section of Ref. [1] are strongly supported by the calculation of the helium excited states as well as the hydrogen excited states given in the Excited States of the One-Electron Atom (Quantization) section of Ref. [1] since the electron-photon model is the same in both the excited-states and in the lower-energy states of hydrogen except that the photon provides a central field of magnitude n in the hydrino case and 1/n in the excited-state case.

TABLE VII

Calculated and experimental energies of states of helium.

| n | l | $r_1$ $(a_{He})$ [a] | $r_2$ $(a_{He})$ [b] | Term Symbol | $E_{ele}$ CQM He I Energy Levels [c] (eV) | NIST He I Energy Levels [d] (eV) | Difference CQM − NIST (eV) | Relative Difference [e] (CQM − NIST) |
|---|---|---|---|---|---|---|---|---|
| 1 | 0 | 0.56699 | 0.566987 | $1s^2$ $^1S$ | −24.58750 | −24.58741 | −0.000092 | 0.0000038 |
| 2 | 0 | 0.506514 | 1.42265 | 1s2s $^3S$ | −4.78116 | −4.76777 | −0.0133929 | 0.0028090 |
| 2 | 0 | 0.501820 | 1.71132 | 1s2s $^1S$ | −3.97465 | −3.97161 | −0.0030416 | 0.0007658 |
| 2 | 1 | 0.500571 | 1.87921 | 1s2p $^3P^o_2$ | −3.61957 | −3.6233 | 0.0037349 | −0.0010308 |
| 2 | 1 | 0.500571 | 1.87921 | 1s2p $^3P^o_1$ | −3.61957 | −3.62329 | 0.0037249 | −0.0010280 |
| 2 | 1 | 0.500571 | 1.87921 | 1s2p $^3P^o_0$ | −3.61957 | −3.62317 | 0.0036049 | −0.0009949 |
| 2 | 1 | 0.499929 | 2.01873 | 1s2p $^1P^o$ | −3.36941 | −3.36936 | −0.0000477 | 0.0000141 |
| 3 | 0 | 0.500850 | 2.42265 | 1s3s $^3S$ | −1.87176 | −1.86892 | −0.0028377 | 0.0015184 |
| 3 | 0 | 0.500302 | 2.71132 | 1s3s $^1S$ | −1.67247 | −1.66707 | −0.0054014 | 0.0032401 |
| 3 | 1 | 0.500105 | 2.87921 | 1s3p $^3P^o_2$ | −1.57495 | −1.58031 | 0.0053590 | −0.0033911 |
| 3 | 1 | 0.500105 | 2.87921 | 1s3p $^3P^o_1$ | −1.57495 | −1.58031 | 0.0053590 | −0.0033911 |
| 3 | 1 | 0.500105 | 2.87921 | 1s3p $^3P^o_0$ | −1.57495 | −1.58027 | 0.0053190 | −0.0033659 |
| 3 | 2 | 0.500011 | 2.98598 | 1s3d $^3D_3$ | −1.51863 | −1.51373 | −0.0049031 | 0.0032391 |
| 3 | 2 | 0.500011 | 2.98598 | 1s3d $^3D_2$ | −1.51863 | −1.51373 | −0.0049031 | 0.0032391 |
| 3 | 2 | 0.500011 | 2.98598 | 1s3d $^3D_1$ | −1.51863 | −1.51373 | −0.0049031 | 0.0032391 |
| 3 | 2 | 0.499999 | 3.00076 | 1s3d $^1D$ | −1.51116 | −1.51331 | 0.0021542 | −0.0014235 |
| 3 | 1 | 0.499986 | 3.01873 | 1s3p $^1P^o$ | −1.50216 | −1.50036 | −0.0017999 | 0.0011997 |
| 4 | 0 | 0.500225 | 3.42265 | 1s4s $^3S$ | −0.99366 | −0.99342 | −0.0002429 | 0.0002445 |
| 4 | 0 | 0.500088 | 3.71132 | 1s4s $^1S$ | −0.91637 | −0.91381 | −0.0025636 | 0.0028054 |
| 4 | 1 | 0.500032 | 3.87921 | 1s4p $^3P^o_2$ | −0.87671 | −0.87949 | 0.0027752 | −0.0031555 |
| 4 | 1 | 0.500032 | 3.87921 | 1s4p $^3P^o_1$ | −0.87671 | −0.87949 | 0.0027752 | −0.0031555 |
| 4 | 1 | 0.500032 | 3.87921 | 1s4p $^3P^o_0$ | −0.87671 | −0.87948 | 0.0027652 | −0.0031442 |
| 4 | 2 | 0.500003 | 3.98598 | 1s4d $^3D_3$ | −0.85323 | −0.85129 | −0.0019398 | 0.0022787 |
| 4 | 2 | 0.500003 | 3.98598 | 1s4d $^3D_2$ | −0.85323 | −0.85129 | −0.0019398 | 0.0022787 |
| 4 | 2 | 0.500003 | 3.98598 | 1s4d $^3D_1$ | −0.85323 | −0.85129 | −0.0019398 | 0.0022787 |
| 4 | 2 | 0.500000 | 4.00076 | 1s4d $^1D$ | −0.85008 | −0.85105 | 0.0009711 | −0.0011411 |
| 4 | 3 | 0.500000 | 3.99857 | 1s4f $^3F^o_3$ | −0.85054 | −0.85038 | −0.0001638 | 0.0001926 |
| 4 | 3 | 0.500000 | 3.99857 | 1s4f $^3F^o_4$ | −0.85054 | −0.85038 | −0.0001638 | 0.0001926 |
| 4 | 3 | 0.500000 | 3.99857 | 1s4f $^3F^o_2$ | −0.85054 | −0.85038 | −0.0001638 | 0.0001926 |
| 4 | 3 | 0.500000 | 4.00000 | 1s4f $^1F^o$ | −0.85024 | −0.85037 | 0.0001300 | −0.0001529 |
| 4 | 1 | 0.499995 | 4.01873 | 1s4p $^1P^o$ | −0.84628 | −0.84531 | −0.0009676 | 0.0011446 |
| 5 | 0 | 0.500083 | 4.42265 | 1s5s $^3S$ | −0.61519 | −0.61541 | 0.0002204 | −0.0003582 |

TABLE VII-continued

Calculated and experimental energies of states of helium.

| n | l | $r_1$ $(a_{He})$[a] | $r_2$ $(a_{He})$[b] | Term Symbol | $E_{ele}$ CQM He I Energy Levels[c] (eV) | NIST He I Energy Levels[d] (eV) | Difference CQM − NIST (eV) | Relative Difference[e] (CQM − NIST) |
|---|---|---|---|---|---|---|---|---|
| 5 | 0 | 0.500035 | 4.71132 | 1s5s $^1$S | −0.57750 | −0.57617 | −0.0013253 | 0.0023002 |
| 5 | 1 | 0.500013 | 4.87921 | 1s5p $^3$P$^o_2$ | −0.55762 | −0.55916 | 0.0015352 | −0.0027456 |
| 5 | 1 | 0.500013 | 4.87921 | 1s5p $^3$P$^o_1$ | −0.55762 | −0.55916 | 0.0015352 | −0.0027456 |
| 5 | 1 | 0.500013 | 4.87921 | 1s5p $^3$P$^o_0$ | −0.55762 | −0.55915 | 0.0015252 | −0.0027277 |
| 5 | 2 | 0.500001 | 4.98598 | 1s5d $^3$D$_3$ | −0.54568 | −0.54472 | −0.0009633 | 0.0017685 |
| 5 | 2 | 0.500001 | 4.98598 | 1s5d $^3$D$_2$ | −0.54568 | −0.54472 | −0.0009633 | 0.0017685 |
| 5 | 2 | 0.500001 | 4.98598 | 1s5d $^3$D$_1$ | −0.54568 | −0.54472 | −0.0009633 | 0.0017685 |
| 5 | 2 | 0.500000 | 5.00076 | 1s5d $^1$D | −0.54407 | −0.54458 | 0.0005089 | −0.0009345 |
| 5 | 3 | 0.500000 | 4.99857 | 1s5f $^3$F$^o_3$ | −0.54431 | −0.54423 | −0.0000791 | 0.0001454 |
| 5 | 3 | 0.500000 | 4.99857 | 1s5f $^3$F$^o_4$ | −0.54431 | −0.54423 | −0.0000791 | 0.0001454 |
| 5 | 3 | 0.500000 | 4.99857 | 1s5f $^3$F$^o_2$ | −0.54431 | −0.54423 | −0.0000791 | 0.0001454 |
| 5 | 3 | 0.500000 | 5.00000 | 1s5f $^1$F$^o$ | −0.54415 | −0.54423 | 0.0000764 | −0.0001404 |
| 5 | 4 | 0.500000 | 4.99988 | 1s5g $^3$G$_4$ | −0.54417 | −0.54417 | 0.0000029 | −0.0000054 |
| 5 | 4 | 0.500000 | 4.99988 | 1s5g $^3$G$_5$ | −0.54417 | −0.54417 | 0.0000029 | −0.0000054 |
| 5 | 4 | 0.500000 | 4.99988 | 1s5g $^3$G$_3$ | −0.54417 | −0.54417 | 0.0000029 | −0.0000054 |
| 5 | 4 | 0.500000 | 5.00000 | 1s5g $^1$G | −0.54415 | −0.54417 | 0.0000159 | −0.0000293 |
| 5 | 1 | 0.499998 | 5.01873 | 1s5p $^1$P$^o$ | −0.54212 | −0.54158 | −0.0005429 | 0.0010025 |
| 6 | 0 | 0.500038 | 5.42265 | 1s6s $^3$S | −0.41812 | −0.41838 | 0.0002621 | −0.0006266 |
| 6 | 0 | 0.500016 | 5.71132 | 1s6s $^1$S | −0.39698 | −0.39622 | −0.0007644 | 0.0019291 |
| 6 | 1 | 0.500006 | 5.87921 | 1s6p $^3$P$^o_2$ | −0.38565 | −0.38657 | 0.0009218 | −0.0023845 |
| 6 | 1 | 0.500006 | 5.87921 | 1s6p $^3$P$^o_1$ | −0.38565 | −0.38657 | 0.0009218 | −0.0023845 |
| 6 | 1 | 0.500006 | 5.87921 | 1s6p $^3$P$^o_0$ | −0.38565 | −0.38657 | 0.0009218 | −0.0023845 |
| 6 | 2 | 0.500001 | 5.98598 | 1s6d $^3$D$_3$ | −0.37877 | −0.37822 | −0.0005493 | 0.0014523 |
| 6 | 2 | 0.500001 | 5.98598 | 1s6d $^3$D$_2$ | −0.37877 | −0.37822 | −0.0005493 | 0.0014523 |
| 6 | 2 | 0.500001 | 5.98598 | 1s6d $^3$D$_1$ | −0.37877 | −0.37822 | −0.0005493 | 0.0014523 |
| 6 | 2 | 0.500000 | 6.00076 | 1s6d $^1$D | −0.37784 | −0.37813 | 0.0002933 | −0.0007757 |
| 6 | 3 | 0.500000 | 5.99857 | 1s6f $^3$F$^o_3$ | −0.37797 | −0.37793 | −0.0000444 | 0.0001176 |
| 6 | 3 | 0.500000 | 5.99857 | 1s6f $^3$F$^o_4$ | −0.37797 | −0.37793 | −0.0000444 | 0.0001176 |
| 6 | 3 | 0.500000 | 5.99857 | 1s6f $^3$F$^o_2$ | −0.37797 | −0.37793 | −0.0000444 | 0.0001176 |
| 6 | 3 | 0.500000 | 6.00000 | 1s6f $^1$F$^o$ | −0.37788 | −0.37793 | 0.0000456 | −0.0001205 |
| 6 | 4 | 0.500000 | 5.99988 | 1s6g $^3$G$_4$ | −0.37789 | −0.37789 | −0.0000023 | 0.0000060 |
| 6 | 4 | 0.500000 | 5.99988 | 1s6g $^3$G$_5$ | −0.37789 | −0.37789 | −0.0000023 | 0.0000060 |
| 6 | 4 | 0.500000 | 5.99988 | 1s6g $^3$G$_3$ | −0.37789 | −0.37789 | −0.0000023 | 0.0000060 |
| 6 | 4 | 0.500000 | 6.00000 | 1s6g $^1$G | −0.37788 | −0.37789 | 0.0000053 | −0.0000140 |
| 6 | 5 | 0.500000 | 5.99999 | 1s6h $^3$H$^o_4$ | −0.37789 | −0.37788 | −0.0000050 | 0.0000133 |
| 6 | 5 | 0.500000 | 5.99999 | 1s6h $^3$H$^o_5$ | −0.37789 | −0.37788 | −0.0000050 | 0.0000133 |
| 6 | 5 | 0.500000 | 5.99999 | 1s6h $^3$H$^o_6$ | −0.37789 | −0.37788 | −0.0000050 | 0.0000133 |
| 6 | 5 | 0.500000 | 6.00000 | 1s6h $^1$H$^o$ | −0.37788 | −0.37788 | −0.0000045 | 0.0000119 |
| 6 | 1 | 0.499999 | 6.01873 | 1s6p $^1$P$^o$ | −0.37671 | −0.37638 | −0.0003286 | 0.0008730 |
| 7 | 0 | 0.500019 | 6.42265 | 1s7s $^3$S | −0.30259 | −0.30282 | 0.0002337 | −0.0007718 |
| 7 | 0 | 0.500009 | 6.71132 | 1s7s $^1$S | −0.28957 | −0.2891 | −0.0004711 | 0.0016295 |
| 7 | 1 | 0.500003 | 6.87921 | 1s7p $^3$P$^o_2$ | −0.28250 | −0.28309 | 0.0005858 | −0.0020692 |
| 7 | 1 | 0.500003 | 6.87921 | 1s7p $^3$P$^o_1$ | −0.28250 | −0.28309 | 0.0005858 | −0.0020692 |
| 7 | 1 | 0.500003 | 6.87921 | 1s7p $^3$P$^o_0$ | −0.28250 | −0.28309 | 0.0005858 | −0.0020692 |
| 7 | 2 | 0.500000 | 6.98598 | 1s7d $^3$D$_3$ | −0.27819 | −0.27784 | −0.0003464 | 0.0012468 |
| 7 | 2 | 0.500000 | 6.98598 | 1s7d $^3$D$_2$ | −0.27819 | −0.27784 | −0.0003464 | 0.0012468 |
| 7 | 2 | 0.500000 | 6.98598 | 1s7d $^3$D$_1$ | −0.27819 | −0.27784 | −0.0003464 | 0.0012468 |
| 7 | 2 | 0.500000 | 7.00076 | 1s7d $^1$D | −0.27760 | −0.27779 | 0.0001907 | −0.0006864 |
| 7 | 3 | 0.500000 | 6.99857 | 1s7f $^3$F$^o_3$ | −0.27769 | −0.27766 | −0.0000261 | 0.0000939 |
| 7 | 3 | 0.500000 | 6.99857 | 1s7f $^3$F$^o_4$ | −0.27769 | −0.27766 | −0.0000261 | 0.0000939 |
| 7 | 3 | 0.500000 | 6.99857 | 1s7f $^3$F$^o_2$ | −0.27769 | −0.27766 | −0.0000261 | 0.0000939 |
| 7 | 3 | 0.500000 | 7.00000 | 1s7f $^1$F$^o$ | −0.27763 | −0.27766 | 0.0000306 | −0.0001102 |
| 7 | 4 | 0.500000 | 6.99988 | 1s7g $^3$G$_4$ | −0.27763 | −0.27763 | −0.0000043 | 0.0000155 |
| 7 | 4 | 0.500000 | 6.99988 | 1s7g $^3$G$_5$ | −0.27763 | −0.27763 | −0.0000043 | 0.0000155 |
| 7 | 4 | 0.500000 | 6.99988 | 1s7g $^3$G$_3$ | −0.27763 | −0.27763 | −0.0000043 | 0.0000155 |
| 7 | 4 | 0.500000 | 7.00000 | 1s7g $^1$G | −0.27763 | −0.27763 | 0.0000004 | −0.0000016 |
| 7 | 5 | 0.500000 | 6.99999 | 1s7h $^3$H$^o_5$ | −0.27763 | −0.27763 | 0.0000002 | −0.0000009 |
| 7 | 5 | 0.500000 | 6.99999 | 1s7h $^3$H$^o_6$ | −0.27763 | −0.27763 | 0.0000002 | −0.0000009 |
| 7 | 5 | 0.500000 | 6.99999 | 1s7h $^3$H$^o_4$ | −0.27763 | −0.27763 | 0.0000002 | −0.0000009 |
| 7 | 5 | 0.500000 | 7.00000 | 1s7h $^1$H$^o$ | −0.27763 | −0.27763 | 0.0000006 | −0.0000021 |
| 7 | 6 | 0.500000 | 7.00000 | 1s7i $^3$I$_5$ | −0.27763 | −0.27762 | −0.0000094 | 0.0000339 |
| 7 | 6 | 0.500000 | 7.00000 | 1s7i $^3$I$_6$ | −0.27763 | −0.27762 | −0.0000094 | 0.0000339 |
| 7 | 6 | 0.500000 | 6.78349 | 1s7i $^3$I$_7$ | −0.27763 | −0.27762 | −0.0000094 | 0.0000339 |
| 7 | 6 | 0.500000 | 7.00000 | 1s7i $^1$I | −0.27763 | −0.27762 | −0.0000094 | 0.0000338 |
| 7 | 1 | 0.500000 | 7.01873 | 1s7p $^1$P$^o$ | −0.27689 | −0.27667 | −0.0002186 | 0.0007900 |
| 8 | 0 | 0.500011 | 7.42265 | 1s8s $^3$S | −0.22909 | −0.22928 | 0.0001866 | −0.0008139 |
| 8 | 0 | 0.500005 | 7.71132 | 1s8s $^1$S | −0.22052 | −0.2202 | −0.0003172 | 0.0014407 |
| 9 | 0 | 0.500007 | 8.42265 | 1s9s $^3$S | −0.17946 | −0.17961 | 0.0001489 | −0.0008291 |
| 9 | 0 | 0.500003 | 8.71132 | 1s9s $^1$S | −0.17351 | −0.1733 | −0.0002141 | 0.0012355 |
| 10 | 0 | 0.500004 | 9.42265 | 1s10s $^3$S | −0.14437 | −0.1445 | 0.0001262 | −0.0008732 |
| 10 | 0 | 0.500002 | 9.71132 | 1s10s $^1$S | −0.14008 | −0.13992 | −0.0001622 | 0.0011594 |

TABLE VII-continued

Calculated and experimental energies of states of helium.

| n | l | $r_1$ $(a_{He})$[a] | $r_2$ $(a_{He})$[b] | Term Symbol | $E_{ele}$ CQM He I Energy Levels[c] (eV) | NIST He I Energy Levels[d] (eV) | Difference CQM − NIST (eV) | Relative Difference[e] (CQM − NIST) |
|---|---|---|---|---|---|---|---|---|
| 11 | 0 | 0.500003 | 10.42265 | 1s11s $^3$S | −0.11866 | −0.11876 | 0.0001037 | −0.0008734 |
| 11 | 0 | 0.500001 | 10.71132 | 1s11s $^1$S | −0.11546 | −0.11534 | −0.0001184 | 0.0010268 |
|   |   |   |   |   | Avg. | −0.000112 | 0.0000386 |

[a] Radius of the inner electron 1 of singlet excited states with l = 0 from Eq. (9.29); triplet excited states with l = 0 from Eq. (9.37); singlet excited states with l ≠ 0 from Eq. (9.60) for l = 1 or l = 2 and Eq. (9.61) for l = 3, and Eq. (9.62) for l = 4, 5, 6 . . . ; triplet excited states with l ≠ 0 from Eq. (9.69), and 1s$^2$ $^1$S from Eq. (7.19).
[b] Radius of the outer electron 2 of singlet excited states with l = 0 from Eq. (9.11); triplet excited states with l = 0 from Eq. (9.32); singlet excited states with l ≠ 0 from Eq. (9.53); triplet excited states with l ≠ 0 from Eq. (9.64), and 1s$^2$ $^1$S from Eq. (7.19).
[c] Classical quantum mechanical (CQM) calculated excited-state energy levels given by the electric energy (Eq. (9.12)) and the energy level of 1s$^2$ $^1$S is given by Eqs. (7.28-7.30).
[d] Experimental NIST levels [34] with the ionization potential defined as zero.
[e] (Theoretical-Experimental)/Experimental.

3.F Spin-Orbital Coupling of Excited States with l≠0

Due to 1.) the invariance of each of $$\frac{e}{m_e}$$

of the electron, the electron angular momentum of $\hbar$, and $\mu_B$ from the spin angular and orbital angular momentum, 2.) the condition that flux must be linked by the electron orbitsphere in units of the magnetic flux quantum, and 3.) the maximum projection of the spin angular momentum of the electron onto an axis is $$\sqrt{\frac{3}{4}} \hbar,$$

the magnetic energy term of the electron g-factor gives the spin-orbital coupling energy $E_{s/o\ (Eq.\ (2.102))}$:

$$E_{s/o} = 2\frac{\alpha}{2\pi}\left(\frac{e\hbar}{2m_e}\right)\frac{\mu_0 e\hbar}{2(2\pi m_e)\left(\frac{r}{2\pi}\right)^3}\sqrt{\frac{3}{4}} = \frac{\alpha\pi\mu_0 e^2\hbar^2}{m_e^2 r^2}\sqrt{\frac{3}{4}} \qquad (9.70)$$

For the n=2 state of hydrogen, the radius is r=2a$_0$, and the predicted energy difference between the $^2P_{3/2}$ and $^2P_{1/2}$ levels of the hydrogen atom due to spin-orbital interaction is $$E_{s/o} = \frac{\alpha\pi\mu_0 e^2\hbar^2}{8m_e^2 a_0^3}\sqrt{\frac{3}{4}} \qquad (9.71)$$

As in the case of the $^2P_{1/2} \rightarrow {^2S_{1/2}}$ transition, the photon-momentum transfer for the $^2P_{3/2} \rightarrow {^2P_{1/2}}$ transition gives rise to a small frequency shift derived after that of the Lamb shift with $\Delta m_\ell = -1$ included. The energy, $E_{FS}$, for the $^2P_{3/2} \rightarrow {^2P_{1/2}}$ transition called the fine structure splitting is given by Eq. (2.113):

$$E_{FS} = \frac{\alpha^5 (2\pi)^2}{8} m_e c^2 \sqrt{\frac{3}{4}} + \left(13.5983\ eV\left(1 - \frac{1}{2^2}\right)\right)^2 \qquad (9.72)$$

$$\left[\frac{\left(\frac{3}{4\pi}\left(1 - \sqrt{\frac{3}{4}}\right)\right)^2}{2h\mu_e c^2} + \frac{\left(1 + \left(1 - \sqrt{\frac{3}{4}}\right)\right)^2}{2hm_H c^2}\right]$$

$$= 4.5190 \times 10^{-5}\ eV + 1.75407 \times 10^{-7}\ eV$$

$$= 4.53659 \times 10^{-5}\ eV$$

where the first term corresponds to $E_{s/o}$ given by Eq. (9.71) expressed in terms of the mass energy of the electron (Eq. (2.106)) and the second and third terms correspond to the electron recoil and atom recoil, respectively. The energy of 4.53659×10$^{-5}$ eV corresponds to a frequency of 10,969.4 MHz or a wavelength of 2.73298 cm. The experimental value of the $^2P_{3/2} \rightarrow {^2P_{1/2}}$ transition frequency is 10,969.1 MHz. The large natural widths of the hydrogen 2p levels limits the experimental accuracy; yet, given this limitation, the agreement between the theoretical and experimental fine structure is excellent. Using $r_2$ given by Eq. (9.53), the spin-orbital energies were calculated for l=1 using Eq. (9.70) to compare to the effect of different l quantum numbers. There is agreement between the magnitude of the predicted results given in TABLE VIII and the experimental dependence on the l quantum number as given in TABLE VII.

TABLE VIII

Calculated spin-orbital energies of He I singlet excited states with l = 1 as a function of the radius of the outer electron.

| n | $r_2$ $(a_{He})$[a] | Term Symbol | $E_{s/o}$ spin-orbital coupling[b] (eV) |
|---|---|---|---|
| 2 | 2.01873 | 1s2p $^1P^0$ | 0.0000439 |
| 3 | 3.01873 | 1s3p $^1P^0$ | 0.0000131 |
| 4 | 4.01873 | 1s4p $^1P^0$ | 0.0000056 |
| 5 | 5.01873 | 1s5p $^1P^0$ | 0.0000029 |
| 6 | 6.01873 | 1s6p $^1P^0$ | 0.0000017 |
| 7 | 7.01873 | 1s7p $^1P^0$ | 0.0000010 |

[a] Radius of the outer electron 2 from Eq. (9.53).
[b] The spin-orbital coupling energy of electron 2 from Eq. (9.70) using $r_2$ from Eq. (9.53).

4. Systems

Embodiments of the system for performing computing and rendering of the nature of excited-state atomic and atomic-ionic electrons using the physical solutions may comprise a general purpose computer. Such a general purpose computer may have any number of basic configurations. For example, such a general purpose computer may comprise a central processing unit (CPU), one or more specialized processors, system memory, a mass storage device such as a magnetic disk, an optical disk, or other storage device, an input means such as a keyboard or mouse, a display device, and a printer or other output device. A system implementing the present invention can also comprise a special purpose computer or other hardware system and all should be included within its scope.

The display can be static or dynamic such that spin and angular motion with corresponding momenta can be displayed in an embodiment. The displayed information is useful to anticipate reactivity, physical properties, and optical absorption and emission. The insight into the nature of atomic and atomic-ionic excited-state electrons can permit the solution and display of those of other atoms and atomic ions and provide utility to anticipate their reactivity and physical properties as well as facilitate the development of light sources and materials that respond to light.

Embodiments within the scope of the present invention also include computer program products comprising computer readable medium having embodied therein program code means. Such computer readable media can be any available media which can be accessed by a general purpose or special purpose computer. By way of example, and not limitation, such computer readable media can comprise RAM, ROM, EPROM, CD ROM, DVD or other optical disk storage, magnetic disk storage or other magnetic storage devices, or any other medium which can embody the desired program code means and which can be accessed by a general purpose or special purpose computer. Combinations of the above should also be included within the scope of computer readable media. Program code means comprises, for example, executable instructions and data which cause a general purpose computer or special purpose computer to perform a certain function of a group of functions.

Figure 7:
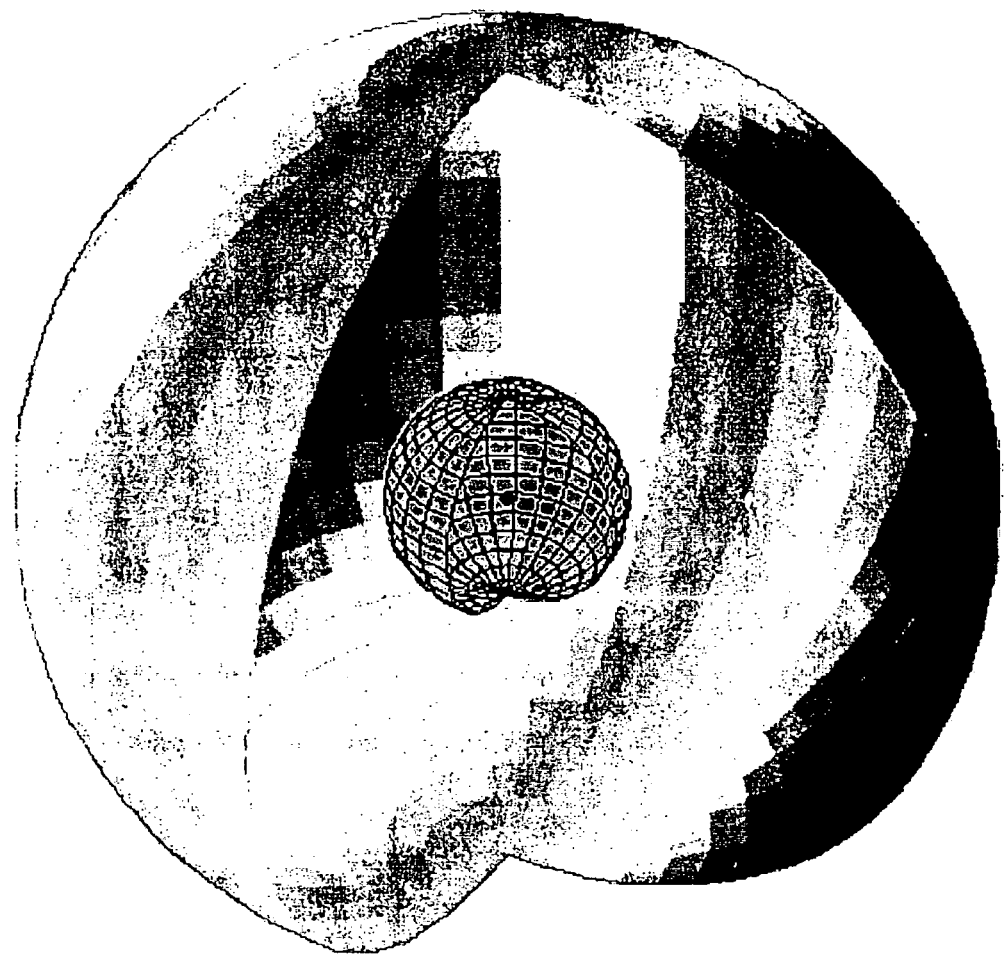
FIG. 7 shows a computer rendering of the helium atom in the n=2, l=1 excited state according to the present Invention.

A specific example of the rendering of the electron of atomic hydrogen using Mathematica and computed on a PC is shown in FIG. 1. The algorithm used was To generate a spherical shell:

SphericalPlot3D[1,{q,0,p},{f,0,2p},Boxed®False, Axes®False]. The rendering can be viewed from different perspectives. A specific example of the rendering of atomic hydrogen using Mathematica and computed on a PC is shown in FIG. 1. The algorithm used was To generate the picture of the electron and proton:

Electron=SphericalPlot3D[1,{q,0,p},{f,0,2p-p/2}, Boxed®False,Axes®False]; Proton=Show[Graphics3D [{Blue,PointSize[0.03],Point[{0,0,0}]}],Boxed®False]; Show[Electron,Proton];

Specific examples of the rendering of the spherical-and-time-harmonic-electron-charge-density functions of non-excited and excited-state electrons using Mathematica and computed on a PC are shown in FIG. 3. The algorithm used was To generate L1MO:

L1MOcolors[theta_,phi_,det_]=Which [det<0.1333,RGBColor[1.000,0.070,0.079],det<0.2666,RGBColor[1.000, 0.369,0.067],det<0.4,RGBColor[1.000,0.681,0.049], det<0.5333,RGBColor[0.984,1.000,0.051],det<0.6666, RGBColor[0.673,1.000,0.058],det<0.8,RGBColor[0.364, 1.000,0.055],det<0.9333,RGBColor[0.071,1.000,0.060], det<1.066,RGBColor[0.085,1.000,0.388],det<1.2, RGBColor[0.070,1.000,0.678],det<1.333,RGBColor [0.070,1.000,1.000],det<1.466,RGBColor[0.067,0.698, 1.000],det<1.6,RGBColor[0.075,0.401, 1.000], det<1.733,RGBColor[0.067,0.082, 1.000],det<1.866,RGBColor[0.326,0.056, 1.000],det£2,RGBColor[0.674, 0.079,1.000]];

L1MO=ParametricPlot3D[{Sin [theta] Cos [phi],Sin [theta] SUN [phi],Cos [theta],L1MOcolors[theta,phi,1+Cos [theta]]}, {theta,0,Pi},{phi,0,2Pi},Boxed®False, Axes®False,Lighting®False,PlotPoints® {20,20},ViewPoint®{-0.273,-2.030,3.494}];

To generate L1MX:

L1MXcolors[theta_, phi_, det_]=Which [det<0.1333, RGBColor[1.000, 0.070, 0.079],det<0.2666, RGBColor[1.000, 0.369, 0.067],det<0.4, RGBColor[1.000, 0.681, 0.049], det<0.5333, RGBColor[0.984, 1.000, 0.051], det<0.6666, RGBColor[0.673, 1.000, 0.058], det<0.8, RGBColor [0.364, 1.000, 0.055],det<0.9333, RGBColor[0.071, 1.000, 0.060], det<1.066, RGBColor[0.085, 1.000, 0.388], det<1.2, RGBColor[0.070, 1.000, 0.678], det<1.333, RGBColor[0.070, 1.000, 1.000],det<1.466, RGBColor [0.067, 0.698, 1.000], det<1.6, RGBColor[0.075, 0.401, 1.000],det<1.733, RGBColor[0.067, 0.082, 1.000], det<1.866, RGBColor[0.326, 0.056, 1.000],det<=2, RGBColor[0.674, 0.079, 1.000]];

L1MX=ParametricPlot3D[{Sin [theta] Cos [phi],Sin [theta] SUN [phi],Cos [theta],L1MXcolors[theta,phi, 1+Sin [theta] Cos [phi]]}, theta,0,Pi}, {phi,0,2Pi},Boxed®False, Axes®False,Lighting®False,PlotPoints®{20,20},ViewPoint®{-0.273,-2.030,3.494}];

To generate L1MY:

L1MYcolors[theta_,phi_,det_]=Which [det<0.1333,RGBColor[1.000,0.070,0.079],det<0.2666,RGBColor[1.000, 0.369,0.067],det<0.4,RGBColor[1.000,0.681,0.049], det<0.5333,RGBColor[0.984,1.000,0.051],det<0.6666, RGBColor[0.673,1.000,0.058],det<0.8,RGBColor[0.364, 1.000,0.055],det<0.9333,RGBColor[0.071,1.000,0.060], det<1.066,RGBColor[0.085,1.000,0.388],det<1.2, RGBColor[0.070,1.000,0.678],det<1.333,RGBColor [0.070, 1.000,1.000],det<1.466,RGBColor[0.067,0.698, 1.0001,det<1.6,RGBColor[0.075,0.401,1.000], det<1.733,RGBColor[0.067,0.082, 1.000],det<1.866,RGBColor[0.326,0.056, 1.000],det£2,RGBColor[0.674, 0.079, 1.000]);

L1MY=ParametricPlot3D[{Sin [theta] Cos [phi],Sin [theta] SUN [phi],Cos [theta],L1MYcolors[theta,phi,1+Sin [theta] SUN [phi]]}, {theta,0,Pi}, {phi,0,2Pi}, Boxed®False,Axes®False,Lighting®False,PlotPoints®{20,20}];

To generate L2MO:

L2MOcolors[theta_, phi_, det_]=Which [det<0.2, RGBColor[1.000, 0.070, 0.079],det<0.4, RGBColor[1.000, 0.369, 0.067], det<0.6, RGBColor[1.000, 0.681, 0.049], det<0.8, RGBColor[0.984, 1.000, 0.051],det<1, RGBColor[0.673, 1.000, 0.058], det<1.2, RGBColor[0.364, 1.000, 0.055],det<1.4, RGBColor[0.071, 1.000, 0.060], det<1.6, RGBColor[0.085, 1.000, 0.388],det<1.8, RGBColor[0.070, 1.000, 0.678],det<2, RGBColor[0.070, 1.000, 1.000],det<2.2, RGBColor[0.067, 0.698, 1.000], det<2.4, RGBColor[0.075, 0.401, 1.000],det<2.6, RGB- Color[0.067, 0.082, 1.000],det<2.8, RGBColor[0.326, 0.056, 1.000],det<=3, RGBColor[0.674, 0.079, 1.000]];
L2MO=ParametricPlot3D[{Sin [theta] Cos [phi], Sin [theta] Sin [phi], Cos [theta],
L2MOcolors[theta, phi, 3 Cos [theta] Cos [theta]]},
{theta, 0, Pi}, {phi, 0, 2Pi},
Boxed->False, Axes->False, Lighting->False,
PlotPoints->{20, 20},
ViewPoint->{−0.273, −2.030, 3.494}];

To generate L2MF:
L2MFcolors[theta_,phi_,det_=Which  [det<0.1333,RGBColor[1.000,0.070,0.079],det<0.2666,RGBColor[1.000, 0.369,0.067],det<0.4,RGBColor[1.000,0.681,0.049], det<0.5333,RGBColor[0.984,1.000,0.051],det<0.6666, RGBColor[0.673,1.000,0.058],det<0.8,RGBColor[0.364, 1.000,0.055],det<0.9333,RGBColor[0.071,1.000,0.060], det<1.066,RGBColor[0.085,1.000,0.388],det<1:2, RGBColor[0.070,1.000,0.678],det<1.333,RGBColor [0.070, 1.000,1.000],det<1.466,RGBColor[0.067,0.698, 1.000],det<]0.6,RGBColor[0.075,0.401,1.000], det<1.733,RGBColor[0.067,0.082, 1.000],det<1.866,RGBColor[0.326,0.056, 1.000],det£2,RGBColor[0.674, 0.079, 1.000]];
L2MF=ParametricPlot3D[{Sin [theta] Cos [phi],Sin [theta] SUN [phi],Cos [theta],L2MFcolors[theta,phi,1+0.72618 Sin [theta] Cos [phi] 5 Cos [theta] Cos [theta]-0.72618 Sin [theta] Cos [phi]]}, {theta,0,Pi},{phi,0,2Pi}, Boxed®False,Axes®False,Lighting®False,PlotPoints®{20,20},ViewPoint®{−0.273,−2.030,2.494}];

To generate L2MX2Y2:
L2MX2Y2colors[theta_,phi_,det_]=Which  [det<0.1333, RGBColor[1.000,0.070,0.079],det<0.2666,RGBColor [1.000,0.369,0.067],det<0.4,RGBColor[1.000,0.681, 0.049],det<0.5333,RGBColor[0.984,1.000,0.051], det<0.6666,RGBColor[0.673,1.000,0.058],det<0.8, RGBColor[0.364,1.000,0.055],det<0.9333,RGBColor [0.071,1.000,0.060],det<1.066,RGBColor[0.085,1.000, 0.388],det<1.2,RGBColor[0.070,1.000,0.678],det<1.333, RGBColor[0.070,1.000,1.000],det<1.466,RGBColor [0.067,0.698, 1.000],det<1.6,RGBColor[0.075,0.401, 1.000],det<1.733,RGBColor[0.067,0.082, 1.000], det<1.866,RGBColor[0.326,0.056, 1.000],det2, RGBColor[0.674,0.079,1.000]];
L2MX2Y2=ParametricPlot3D[Sin [theta] Cos [phi],Sin [theta] SUN [phi],Cos [theta],L2MX2Y2colors[theta,phi, 1+Sin [theta] Sin [theta] Cos [2 phi]]}, {theta,0,Pi},{phi, 0,2Pi},Boxed®False,Axes®False,Lighting®False,PlotPoints®{20,20},ViewPoint®{−0.273,−2.030,3.494}];

To generate L2MXY:
L2MXYcolors[theta_,phi_,det_]=Which [det<0.1333,RGBColor[1.000,0.070,0.079],det<0.2666,RGBColor[1.000, 0.369,0.067],det<0.4,RGBColor[1.000,0.681,0.049], det<0.5333,RGBColor[0.984,1.000,0.051],det<0.6666, RGBColor[0.673,1.000,0.058],det<0.8,RGBColor[0.364, 1.000,0.055],det<0.9333,RGBColor[0.071,1.000,0.060], det<1.066,RGBColor[0.085,1.000,0.388],det<1.2, RGBColor[0.070,1.000,0.678],det<1.333,RGBColor [0.070, 1.000,1.000],det<1.466,RGBColor[0.067,0.698, 1.000],det<1.6,RGBColor[0.075,0.401,1.000], det<1.733,RGBColor[0.067,0.082, 1.000],det<1.866,RGBColor[0.326,0.056, 1.000],det£2,RGBColor[0.674, 0.079,1.000]];
ParametricPlot3D[{Sin [theta] Cos [phi],Sin [theta] SUN [phi],Cos [theta],L2MXYcolors[theta,phi, 1+Sin [theta] Sin [theta] Sin [2phi]]}, {theta,0,Pi}, {phi,0,2Pi}, Boxed®False,Axes®False,Lighting®False,PlotPoints®{20,20},ViewPoint®{−0.273,−2.030,3.494}];

The radii of orbitspheres of the electrons of each excited-state atom and atomic ion are calculated by solving the force balance equation given by Maxwell's equations for a given set of quantum numbers, and the state is displayed as modulated charge-density waves on each two-dimensional orbitsphere at each calculated radius. A computer rendering of the helium atom in the n=2, l=1 excited state according to the present Invention is shown in FIG. 7. The algorithm used was
<<Calculus'VectorAnalysis'
<<Graphics'ParametricPlot3D'
<<Graphics'Shapes'
<<Graphics'Animation'
<<Graphics'SurfaceOfRevolution'
<<Graphics'Colors'
Electron=SphericalPlot3D[Evaluate[Append[{0.25}, {Green}]], {theta,0,Pi}, {theta,0,2Pi-Pi/2},Boxed\[Rule] False,Axes\[Rule]False,PlotPoints\[Rule]{20,20},Lighting\[Rule]False];
Proton=Show[Graphics3D[{Red,PointSize[0.01],Point[{0, 0,0}]}],Boxed\[Rule]False];
InnerH=Show[Electron,Proton];
L1MXcolors[theta_, phi_, det_]=
Which [det<0.1333, RGBColor[1.000, 0.070, 0.079],
det<0.2666, RGBColor[1.000, 0.369, 0.067],
det<0.4, RGBColor[1.000, 0.681, 0.049],
det<0.5333, RGBColor[0.984, 1.000, 0.051],
det<0.6666, RGBColor[0.673, 1.000, 0.058],
det<0.8, RGBColor[0.364, 1.000, 0.055],
det<0.9333, RGBColor[0.071, 1.000, 0.060],
det<1.066, RGBColor[0.085, 1.000, 0.388],
det<1.2, RGBColor[0.070, 1.000, 0.678],
det<1.333, RGBColor[0.070, 1.000, 1.000],
det<1.466, RGBColor[0.067, 0.698, 1.000],
det<1.6, RGBColor[0.075, 0.401, 1.000],
det<1.733, RGBColor[0.067, 0.082, 1.000],
det<1.866, RGBColor[0.326, 0.056, 1.000],
det<=2, RGBColor[0.674, 0.079, 1.000]];
\!\(\(Do[\[IndentingNewLine]L1MX=ParametricPlot3D [Evaluate[Append[\[IndentingNewLine] {Sin [theta]\Cos [phi], Sin [theta]\ Sin [phi], Cos [theta]}, \[IndentingNewLine]{EdgeForm[ ], L1MXcolors[theta, phi+\((\(\(2 Pi\) V30\)i) \), 1+Sin [theta]\ Cos [phi+\((\(\(2Pi\)V30\)i)\)]]}\ [IndentingNewLine]]], {theta, 0, Pi}, {phi, 0, Pi/2+Pi}, Boxed \[Rule] False, Axes \[Rule] False, Lighting \[Rule] False, PlotPoints \[Rule] {35, 35}, ViewPoint \[Rule] {0,0, 2}, ImageSize \[Rule] 72*6], \[IndentingNewLine] {i, 1, 1}]; \)\)

Show[InnerH,L1MX,Lighting[Rule]False];

The present Invention may be embodied in other specific forms without departing from the spirit or essential attributes thereof and, accordingly, reference should be made to the appended claims, rather than to the foregoing specification, as indicating the scope of the Invention.

References which are incorporated herein by reference in their entirety and referred to above throughout using [brackets]:

1. R. Mills, *The Grand Unified Theory of Classical Quantum Mechanics*, January 2005 Edition; posted at http://www.blacklightpower.com/bookdownload.shtml.
2. R. L. Mills, "The Grand Unified Theory of Classical Quantum Mechanics", Int. J. Hydrogen Energy, Vol. 27, No. 5, (2002), pp. 565-590.

3. R. L. Mills, "Classical Quantum Mechanics", submitted; posted at http://www.blacklightpower.com/pdf/CQMTheoryPaperTablesand%20Figures080403.pdf.
4. R. L. Mills, "The Nature of the Chemical Bond Revisited and an Alternative Maxwellian Approach", submitted; posted at http://www.blacklightpower.com/pdf/technical/H2 PaperTableFiguresCaptions111303.pdf.
5. R. L. Mills, "Exact Classical Quantum Mechanical Solutions for One-Through Twenty-Electron Atoms", submitted; posted at http://www.blacklightpower.com/pdf/technical/Exact%20Classical%20Quantum%20Mechanical%20Solutions%20for%20One-%20Through%20Twenty-Electron%20Atoms%20042204.pdf.
6. R. L. Mills, "Maxwell's Equations and QED: Which is Fact and Which is Fiction", submitted; posted at http://www.blacklightpower.com/pdf/technical/MaxwellianEquationsandQED080604.pdf.
7. R. L. Mills, "Exact Classical Quantum Mechanical Solution for Atomic Helium Which Predicts Conjugate Parameters from a Unique Solution for the First Time", submitted; posted at http://www.blacklightpower.com/pdf/technical/ExactCQMSolutionforAtomicHelium073004.pdf.
8. R. L. Mills, "The Fallacy of Feynman's Argument on the Stability of the Hydrogen Atom According to Quantum Mechanics", submitted; posted athttp://www.blacklightpower.com/pdf/Feynman%27s%20Argument%20Spec%20UPDATE%20091003.pdf.
9. R. Mills, "The Nature of Free Electrons in Superfluid Helium—a Test of Quantum Mechanics and a Basis to Review its Foundations and Make a Comparison to Classical Theory", Int. J. Hydrogen Energy, Vol. 26, No. 10, (2001), pp. 1059-1096.
10. R. Mills, "The Hydrogen Atom Revisited", Int. J. of Hydrogen Energy, Vol. 25, Issue 12, December, (2000), pp. 1171-1183.
11. P. Pearle, Foundations of Physics, "Absence of radiationless motions of relativistically rigid classical electron", Vol. 7, Nos. 11/12, (1977), pp. 931-945.
12. V. F. Weisskopf, Reviews of Modern Physics, Vol. 21, No. 2, (1949), pp. 305-315.
13. H. Wergeland, "The Klein Paradox Revisited", *Old and New Questions in Physics, Cosmology, Philosophy, and Theoretical Biology*, A. van der Merwe, Editor, Plenum Press, New York, (1983), pp. 503-515.
14. A. Einstein, B. Podolsky, N. Rosen, Phys. Rev., Vol. 47, (1935), p. 777.
15. F. Dyson, "Feynman's proof of Maxwell equations", Am. J. Phys., Vol. 58, (1990), pp. 209-211.
16. H. A. Haus, "On the radiation from point charges", American Journal of Physics, Vol. 54, 1126-1129 (1986).
17. http://www.blacklightpower.com/new.shtml.
18. D. A. McQuarrie, *Quantum Chemistry*, University Science Books, Mill Valley, Calif., (1983), pp. 206-225.
19. J. Daboul and J. H. D. Jensen, Z. Physik, Vol. 265, (1973), pp. 455-478.
20. T. A. Abbott and D. J. Griffiths, Am. J. Phys., Vol. 53, No. 12, (1985), pp. 1203-1211.
21. G. Goedecke, Phys. Rev 135B, (1964), p. 281.
22. D. A. McQuarrie, *Quantum Chemistry*, University Science Books, Mill Valley, Calif., (1983), pp. 238-241.
23. R. S. Van Dyck, Jr., P. Schwinberg, H. Dehmelt, "New high precision comparison of electron and positron g factors", Phys. Rev. Lett., Vol. 59, (1987), p. 26-29.
24. C. E. Moore, "Ionization Potentials and Ionization Limits Derived from the Analyses of Optical Spectra, Nat. Stand. Ref. Data Ser.-Nat. Bur. Stand. (U.S.), No. 34, 1970.
25. R. C. Weast, *CRC Handbook of Chemistry and Physics*, 58 Edition, CRC Press, West Palm Beach, Fla., (1977), p. E-68.
26. J. D. Jackson, Classical Electrodynamics, Second Edition, John Wiley & Sons, New York, (1975), pp. 236-240, 601-608, 786-790.
27. E. M. Purcell, *Electricity and Magnetism*, McGraw-Hill, New York, (1985), Second Edition, pp. 451-458.
28. NIST Atomic Spectra Database, www.physics.nist.gov/cgi-bin/AtData/display.ksh.
29. F. Bueche, *Introduction to Physics for Scientists and Engineers*, McGraw-Hill, (1975), pp. 352-353.
30. J. D. Jackson, *Classical Electrodynamics*, Second Edition, John Wiley & Sons, New York, (1975), pp. 739-779.
31. M. Mizushima, *Quantum Mechanics of Atomic Spectra and Atomic Structure*, W. A. Benjamin, Inc., New York, (1970), p. 17.
32. J. D. Jackson, *Classical Electrodynamics*, Second Edition, John Wiley & Sons, New York, (1975), pp. 747-752.
33. J. D. Jackson, *Classical Electrodynamics*, Second Edition, John Wiley & Sons, New York, (1975), pp. 503-561.
34. NIST Atomic Spectra Database, www.physics.nist.gov/cgi-bin/AtData/display.ksh.
35. J. D. Jackson, *Classical Electrodynamics*, Second Edition, John Wiley & Sons, New York, (1975), pp. 739-779.
36. J. D. Jackson, *Classical Electrodynamics*, Second Edition, John Wiley & Sons, New York, (1975), p. 759.
37. J. D. Jackson, *Classical Electrodynamics*, Second Edition, John Wiley & Sons, New York, (1975), pp. 236-240, 601-608, 786-790.

I claim:

1. A system, comprising:

physical, Maxwellian solutions of the charge, mass, and current density functions of atoms and atomic ions, a processing means for computing the nature of excited state atomic and atomic ionic electrons, an output means for rendering the nature of excited state atomic and atomic ionic electrons;

a computer-readable medium containing instructions that are executable by a computer to compute and render the nature of excited state atomic and atomic ionic electrons, wherein the instructions comprise an algorithm programmed in Mathematica based on the physical solutions, wherein an algorithm for the rendering an electron of atomic hydrogen is SphericalPlot3D[1,{q,0,p},{f,0,2p},Boxed->False,Axes->False]; and an algorithm for rendering atomic hydrogen is Electron=SphericalPlot3D[1,{q,0,p},{f,0,2p-p/2},Boxed->False,Axes->False];

Proton=Show[Graphics3D[{Blue,PointSize[0.03],Point[{0,0,0}]}],Boxed->False];

Show[Electron,Proton].

2. The system of claim 1, wherein the algorithm for rendering the spherical-and-time-harmonic-electron-charge-density functions is To generate L1MO:

L1MOcolors[theta_,phi_,det_]=Which [det<0.1333,RGBColor[1.000,0.070,0.079],det<0.26 66,RGBColor[1.000,0.369,0.067],det<0.4,RGBColor[1.000,0.681,0.049],det<0.5333,RGB Color[0.984,1.000,0.051],det<0.6666,RGBColor[0.673,1.000,0.058],det<0.8, RGBColor[0.364,1.000,0.055],det<0.9333,RGBColor[0.071,1.000,0.060],det<1.066,RGBColor[0.085, 1.000,0.388],det<1.2,RGBColor[0.070,1.000,0.678], det<1.333,RGBColor[0.070, 1.000,1.000],det<1.466, RGBColor[0.067,0.698, 1.000],det<1.6,RGBColor

[0.075,0.401,1.000],det<1.733,RGBColor[0.067, 0.082, 1.000],det<1.866,RGBColor[0.326,0.056, 1.000],det£2,RGBColor[0.674,0.079,1.000]]];

L1MO=ParametricPlot3D[{Sin [theta] Cos [phi],Sin [theta] Sin [phi],Cos [theta],L1 MOcolors[theta,phi,1+ Cos [theta]]}, {theta,0,Pi},{phi,0,2Pi}, Boxed->False, Axes->False,Lighting->False,PlotPoints->{20,20}, ViewPoint->{-0.273,-2.030,3.494}];

To generate L1MX:

L1MXcolors[theta_, phi_, det_]=Which [det<0.1333, RGBColor[1.000, 0.070, 0.079],det<0.2666, RGBColor[1.000, 0.369, 0.067],det<0.4, RGBColor[1.000, 0.681, 0.049],det<0.5333, RGBColor[0.984, 1.000, 0.051],det<0.6666, RGBColor[0.673, 1.000, 0.058], det<0.8, RGBColor[0.364, 1.000, 0.055],det<0.9333, RGBColor[0.071, 1.000, 0.060], det<1.066, RGBColor[0.085, 1.000, 0.388],det<1.2, RGBColor[0.070, 1.000, 0.678], det<1.333, RGBColor[0.070, 1.000, 1.000], det<1.466, RGBColor[0.067, 0.698, 1.000], det<1.6, RGBColor[0.075, 0.401, 1.000],det<1.733, RGBColor [0.067, 0.082, 1.000], det<1.866, RGBColor[0.326, 0.056, 1.000],det<=2, RGBColor[0.674, 0.079, 1.000]]];

L1MX=ParametricPlot3D[{Sin [theta] Cos [phi],Sin [theta] Sin [phi],Cos [theta],L1MXcolors[theta,phi, 1+Sin [theta] Cos [phi]]}, {theta,0,Pi}, {phi,0,2Pi}, Boxed->False,Axes->False, Lighting->False,PlotPoints->{20,20},ViewPoint->{-0.273,-2.030,3.494}];

To generate L1MY:

L1MYcolors[theta_,phi_,det_]=Which [det<0.1333,RGBColor[1.000,0.070,0.079],det<0.2666,RGBColor[1.000,0.369,0.067],det<0.4,RGBColor[1.000,0.681, 0.049],det<0.5333,RGBColor[0.984,1.000,0.051], det<0.6666,RGBColor[0.673,1.000,0.058],det<0.8, RGBColor[0.364,1.000,0.055],det<0.9333,RGBColor [0.071,1.000,0.060],det<1.066,RGBColor[0.085, 1.000,0.388],det<1.2,RGBColor[0.070,1.000,0.678], det<1.333,RGBColor[0.070,1.000,1.000],det<1.466, RGBColor[0.067,0.698,1.000],det<1.6,RGBColor [0.075,0.401,1.000], det<1.733,RGBColor[0.067, 0.082,1.000],det<1.866,RGBColor[0.326,0.056, 1.000],det£2,RGBColor[0.674,0.079,1.000]]];

L1MY=ParametricPlot3D[{Sin [theta] Cos [phi],Sin [theta] Sin [phi],Cos [theta],L1 MYcolors[theta,phi, 1+Sin [theta] Sin [phi]]}, {theta,0,Pi}, {phi,0,2Pi}, Boxed->False,Axes->False,Lighting->False,PlotPoints->{20,20}];

To generate L2MO:

L2MOcolors[theta_, phi_, det_]=Which [det<0.2, RGBColor[1.000, 0.070, 0.079],det<0.4, RGBColor[1.000, 0.369, 0.067],det<0.6, RGBColor[1.000, 0.681, 0.049], det<0.8, RGBColor[0.984, 1.000, 0.051],det<1, RGBColor[0.673, 1.000, 0.058],det<1.2, RGBColor[0.364, 1.000, 0.055],det<1.4, RGBColor[0.071, 1.000, 0.060], det<1.6, RGBColor[0.085, 1.000, 0.388],det<1.8, RGBColor[0.070, 1.000, 0.678],det<2, RGBColor [0.070, 1.000, 1.000],det<2.2, RGBColor[0.067, 0.698, 1.000],det<2.4, RGBColor[0.075, 0.401, 1.000], det<2.6, RGBColor[0.067, 0.082, 1.000],det<2.8, RGBColor[0.326, 0.056, 1.000],det<=3, RGBColor [0.674, 0.079, 1.000]]];

L2MO=ParametricPlot3D[{Sin [theta] Cos [phi], Sin [theta] Sin [phi], Cos [theta], L2MOcolors[theta, phi, 3 Cos [theta] Cos [theta]]}, {theta, 0, Pi}, {phi, 0, 2Pi}, Boxed->False, Axes->False, Lighting->False, Plot-Points->{20, 20}, ViewPoint->{-0.273, -2.030, 3.494}];

To generate L2MF:

L2MFcolors[theta_,phi_,det_]=Which [det<0.1333,RGBColor[1.000,0.070,0.079],det<0.2666,RGBColor [1.000,0.369,0.067],det<0.4,RGBColor[1.000,0.681, 0.049],det<0.5333,RGBColor[0.984,1.000,0.051], det<0.6666,RGBColor[0.673,1.000,0.058],det<0.8, RGBColor[0.364,1.000,0.055],det<0.9333,RGBColor [0.071,1.000,0.060],det<1.066,RGBColor[0.085, 1.000,0.388],det<1.2,RGBColor[0.070,1.000,0.678], det<1.333,RGBColor[0.070,1.000,1.000],det<1.466, RGBColor[0.067,0.698,1.000],det<1.6,RGBColor [0.075,0.401,1.000],det<1.733,RGBColor[0.067, 0.082,1.000],det<1.866,RGBColor[0.326,0.056, 1.000],det£2,RGBColor[0.674,0.079, 1.000]]];

L2MF=ParametricPlot3D[{Sin [theta] Cos [phi],Sin [theta] Sin [phi],Cos [theta],L2MFcolors[theta,phi,1+ 0.72618 Sin [theta] Cos [phi] 5 Cos [theta] Cos [theta]- 0.72618 Sin [theta] Cos [phi]]}, {theta,0,Pi}, {phi,0, 2Pi},Boxed->False,Axes->False,Lighting->False, PlotPoints->{20,20},ViewPoint->{-0.273,-2.030, 2.494}];

To generate L2MX2Y2:

L2MX2Y2colors[theta_,phi_,det_]=Which [det<0.1333, RGBColor[1.000,0.070,0.079],det<0.2666,RGBColor [1.000,0.369,0.067],det<0.4,RGBColor[1.000,0.681, 0.049],det<0.5333,RGBColor[0.984,1.000,0.051], det<0.6666,RGBColor[0.673,1.000,0.058],det<0.8, RGBColor[0.364,1.000,0.055],det<0.9333,RGBColor [0.071,1.000,0.060],det<1.066,RGBColor[0.085, 1.000,0.388],det<1.2,RGBColor[0.070,1.000,0.678], det<1.333,RGBColor[0.070,1.000,1.000],det<1.466, RGBColor[0.067,0.698,1.000],det<1.6,RGBColor [0.075,0.401,1.000],det<1.733,RGBColor[0.067, 0.082, 1.000],det<1.866,RGBColor[0.326,0.056, 1.000],det£2,RGBColor[0.674,0.079, 1.000]]];

L2MX2Y2=ParametricPlot3D[{Sin [theta] Cos [phi],Sin [theta] Sin [phi],Cos [theta],L2MX2Y2colors[theta,phi, 1+Sin [theta] Sin [theta] Cos [2 phi]]}, {theta,0,Pi}, {phi,0,2Pi},Boxed->False,Axes->False, Lighting-> False,PlotPoints->{20,20},ViewPoint->{-0.273,- 2.030,3.494}];

To generate L2MXY:

L2MXYcolors[theta_,phi_,det_]=Which [det<0.1333, RGBColor[1.000,0.070,0.079],det<0.2666,RGBColor [1.000,0.369,0.067],det<0.4,RGBColor[1.000,0.681, 0.049],det<0.5333,RGBColor[0.984,1.000,0.051], det<0.6666,RGBColor[0.673,1.000,0.058],det<0.8, RGBColor[0.364,1.000,0.055],det<0.9333,RGBColor [0.071,1.000,0.060],det<1.066,RGBColor[0.085, 1.000,0.388],det<1.2,RGBColor[0.070,1.000,0.678], det<1.333,RGBColor[0.070,1.000,1.000],det<1.466, RGBColor[0.067,0.698,1.000],det<1.6,RGBColor [0.075,0.401,1.000], det<1.733,RGBColor[0.067, 0.082,1.000],det<1.866,RGBColor[0.326,0.056, 1.000],det£2,RGBColor[0.674,0.079, 1.000]]];

ParametricPlot3D[{Sin [theta] Cos [phi],Sin [theta] Sin [pbi],Cos [theta],L2MXYcolors[theta,phi,1+Sin [theta] Sin [theta] Sin [2 phi]]}, {theta,0,Pi}, {phi,0,2Pi}, Boxed->False,Axes->False,Lighting>False, PlotPoints->{20,20},ViewPoint->{-0.273,-2.030, 3.494}].

3. The system of claim 1, wherein an algorithm for rendering the spherical-and-time-harmonic-electron-charge-density functions for the helium atom in the n=2, l=1 excited state is <<Calculus'VectorAnalysis'
<<Graphics'ParametricPlot3D'

```
<<Graphics`Shapes`
<<Graphics`Animation`
<<Graphics`SurfaceOfRevolution`
<<Graphics`Colors`
Electron=SphericalPlot3D[Evaluate[Append[{0.25},
   {Green}]], {theta,0,Pi}, {theta, 0,2Pi-Pi/2},Boxed\
   [Rule]False,Axes\[Rule]False,PlotPoints\[Rule] {20,
   20},Lighting\[Rule]False];
Proton=Show[Graphics3D[{Red,PointSize[0.0],Point[{0,
   0,0}]}],Boxed[Rule]False];
InnerH=Show[Electron,Proton];
L1MXcolors[theta_, phi_, det_]=
   Which [det<0.1333, RGBColor[1.000, 0.070, 0.079],
   det<0.2666, RGBColor[1.000, 0.369, 0.067],
   det<0.4, RGBColor[1.000, 0.681, 0.049],
   det<0.5333, RGBColor[0.984, 1.000, 0.051],
   det<0.6666, RGBColor[0.673, 1.000, 0.058],
   det<0.8, RGBColor[0.364, 1.000, 0.055],
   det<0.9333, RGBColor[0.071, 1.000, 0.060],
   det<1.066, RGBColor[0.085, 1.000, 0.388],
   det<1.2, RGBColor[0.070, 1.000, 0.678],
   det<1.333, RGBColor[0.070, 1.000, 1.000],
   det<1.466, RGBColor[0.067, 0.698, 1.000],
   det<1.6, RGBColor[0.075, 0.401, 1.000],
   det<1.733, RGBColor[0.067, 0.082, 1.000],
   det<1.866, RGBColor[0.326, 0.056, 1.000],
   det<=2, RGBColor[0.674, 0.079, 1.000]];
\!\(\(Do[\[IndentingNewLine]L1 MX=ParametricPlot3D
   [Evaluate[Append[\[IndentingNewLine] {Sin [theta]\
   Cos [phi], Sin [theta]\ Sin [phi], Cos [theta]}, \[Indent-
   ingNewLine]{EdgeForm[ ], L1MXcolors[theta, phi+\
   ((\(\(2 Pi\)V30\)i)\), 1+Sin [theta]\ Cos [phi+\((\(\(2 Pi\)
   V30\)i) \)]]}\[IndentingNewLine]]], {theta, 0, Pi}, {phi,
   0, Pi/2+Pi}, Boxed \[Rule] False, Axes \[Rule] False,
   Lighting \[Rule] False, PlotPoints \[Rule] {35, 35},
   ViewPoint \[Rule] {0, 0, 2}, ImageSize \[Rule] 72*6],
   \[IndentingNewLine] {i, 1, 1}];\)\)
Show[InnerH,L1MX,Lighting\[Rule]False].
```

4. The system of claim 1, wherein the physical, Maxwellian solutions of the charge, mass, and current density functions of excited-state atoms and atomic ions comprises a solution of the classical wave equation $$\left[\nabla^2 - \frac{1}{v^2}\frac{\partial^2}{\partial t^2}\right]\rho(r, \theta, \phi, t) = 0.$$

5. The system of claim 4, wherein the time, radial, and angular solutions of the wave equation are separable.

6. The system of claim 5, wherein the radii of orbitspheres of the electrons of each excited-state atom and atomic ion are calculated by solving the force balance equation given by Maxwell's equation for a given set of quantum numbers, and the state is displayed as modulated charge-density waves on each two-dimensional orbitsphere at each calculated radius.

7. The system of claim 5, wherein radial function which does satisfy the boundary conditions is a radial delta function $$f(r) = \frac{1}{r^2}\delta(r - r_n).$$

8. The system of claim 7, wherein the boundary condition is met for a time harmonic function when the relationship between an allowed radius and the electron wavelength is given by $$2\pi r_n = \lambda_n,$$

$$\omega = \frac{\hbar}{m_e r^2}, \text{ and}$$

$$v = \frac{\hbar}{m_e r}$$

where ω is the angular velocity of each point on the electron surface, v is the velocity at each point on the electron surface, and r is the radius of the electron.

9. The system of claim 8, wherein the spin function is given by the uniform function $Y_0^0(\phi,\theta)$ comprising angular momentum components of $$L_{xy} = \frac{\hbar}{4}$$

and $$L_z = \frac{\hbar}{2}.$$

10. The system of claim 9, wherein the atomic and atomic ionic charge and current density functions of excited-state electrons are described by a charge-density (mass-density) function which is the product of a radial delta function, two angular functions (spherical harmonic functions), and a time harmonic function:

$$\rho(r, \theta, \phi, t) = f(r)A(\theta, \phi, t) = \frac{1}{r^2}\delta(r - r_n)A(\theta, \phi, t);$$

$$A(\theta, \phi, t) = Y(\theta, \phi)k(t)$$

wherein the spherical harmonic functions correspond to a traveling charge density wave confined to the spherical shell which gives rise to the phenomenon of orbital angular momentum.

11. The system of claim 10, wherein based on the radial solution, the angular charge and current-density functions of the electron, $A(\theta,\phi,t)$, must be a solution of the wave equation in two dimensions (plus time), $$\left[\nabla^2 - \frac{1}{v^2}\frac{\partial^2}{\partial t^2}\right]A(\theta, \phi, t) = 0$$

where $$\rho(r, \theta, \phi, t) =$$

$$f(r)A(\theta, \phi, t) = \frac{1}{r^2}\delta(r - r_n)A(\theta, \phi, t) \text{ and } A(\theta, \phi, t) = Y(\theta, \phi)k(t)$$

$$\left[\frac{1}{r^2\sin\theta}\frac{\partial}{\partial\theta}\left(\sin\theta\frac{\partial}{\partial\theta}\right)_{r,\phi} + \frac{1}{r^2\sin^2\theta}\left(\frac{\partial^2}{\partial\phi^2}\right)_{r,\theta} - \frac{1}{v^2}\frac{\partial^2}{\partial t^2}\right]A(\theta,\phi,t) = 0$$

where $v$ is the linear velocity of the electron.

12. The system of claim 11, wherein the charge-density functions including the time-function factor are $$\ell = 0$$

$$\rho(r,\theta,\phi,t) = \frac{e}{8\pi r^2}[\delta(r-r_n)][Y_0^0(\theta,\phi) + Y_\ell^m(\theta,\phi)]$$

$$\ell \neq 0$$

$$\rho(r,\theta,\phi,t) = \frac{e}{4\pi r^2}[\delta(r-r_n)][Y_0^0(\theta,\phi) + \text{Re}\{Y_\ell^m(\theta,\phi)e^{i\omega_n t}\}]$$

where $Y_\ell^m(\theta,\phi)$ are the spherical harmonic functions that spin about the z-axis with angular frequency $\omega_n$ with $Y_0^0(\theta,\phi)$ the constant function;

Re $\{Y_\ell^m(\theta,\phi)e^{i\omega_n t}\}=P_\ell^m(\cos\theta)\cos(m\phi+\omega_n t)$ where to keep the form of the spherical harmonic as a traveling wave about the z-axis, $\omega_n'=m\omega_n$.

13. The system of claim 12, wherein the spin and angular moment of inertia, I, angular momentum, L, and energy, E, for quantum number l are given by $$\ell = 0$$

$$I_z = I_{spin} = \frac{m_e r_n^2}{2}$$

$$L_z = I\omega i_z = \pm\frac{\hbar}{2}$$

$$E_{rotational} =$$

$$E_{rotational,spin} = \frac{1}{2}\left[I_{spin}\left(\frac{\hbar}{m_e r_n^2}\right)^2\right] = \frac{1}{2}\left[\frac{m_e r_n^2}{2}\left(\frac{\hbar}{m_e r_n^2}\right)^2\right] = \frac{1}{4}\left[\frac{\hbar^2}{2I_{spin}}\right]$$

$$\ell \neq 0$$

$$I_{orbital} = m_e r_n^2 \left[\frac{\ell(\ell+1)}{\ell^2+\ell+1}\right]^{\frac{1}{2}}$$

$$L_z = m\hbar$$

$$L_{z\,total} = L_{z\,spin} + L_{z\,orbital}$$

$$E_{rotational,orbital} = \frac{\hbar^2}{2I}\left[\frac{\ell(\ell+1)}{\ell^2+2\ell+1}\right]$$

$$T = \frac{\hbar^2}{2m_e r_n^2}$$

$$\langle E_{rotational,orbital}\rangle = 0.$$

14. The system of claim 1, wherein the initial force balance equation for one-electron atoms and ions before excitation is $$\frac{m_e}{4\pi r_1^2}\frac{v_1^2}{r_1} = \frac{e}{4\pi r_1^2}\frac{Ze}{4\pi\varepsilon_o r_1^2} - \frac{1}{4\pi r_1^2}\frac{\hbar^2}{m_p r_n^3}$$

$$r_1 = \frac{a_H}{Z}$$

where $a_H$ is the radius of the hydrogen atom.

15. The system of claim 14, wherein from Maxwell's equations, the potential energy V, kinetic energy T, electric energy or binding energy $E_{ele}$ are $$V = \frac{-Ze^2}{4\pi\varepsilon_o r_1} = \frac{-Z^2 e^2}{4\pi\varepsilon_o a_H} = -Z^2 \times 4.3675 \times 10^{-18} J = -Z^2 \times 27.2\,eV$$

$$T = \frac{Z^2 e^2}{8\pi\varepsilon_o a_H} = Z^2 \times 13.59\,eV$$

$$T = E_{ele} = -\frac{1}{2}\varepsilon_o \int_\infty^{r_1} E^2 dv \text{ where } E = -\frac{Ze}{4\pi\varepsilon_o r^2}$$

$$E_{ele} = -\frac{Z^2 e^2}{8\pi\varepsilon_o a_H} = -Z^2 \times 2.1786 \times 10^{-18} J = -Z^2 \times 13.598\,eV.$$

16. The system of claim 1, wherein the initial force balance equation solution before excitation of two-electron atoms is a central force balance equation with the nonradiation condition given by $$\frac{m_e}{4\pi r_2^2}\frac{v_2^2}{r_2} = \frac{e}{4\pi r_2^2}\frac{(Z-1)e}{4\pi\varepsilon_o r_2^2} + \frac{1}{4\pi r_2^2}\frac{\hbar^2}{Zm_e r_2^3}\sqrt{s(s+1)}$$

which gives the radius of both electrons as $$r_2 = r_1 = a_0\left(\frac{1}{Z-1} - \sqrt{\frac{s(s+1)}{Z(Z-1)}}\right); \quad s = \frac{1}{2}.$$

17. The system of claim 16, wherein the ionization energy for helium, which has no electric field beyond $r_1$ is given by Ionization Energy(He)=−E(electric)+E(magnetic)

where, $$E(\text{electric}) = -\frac{(Z-1)e^2}{8\pi\varepsilon_o r_1}$$

$$E(\text{magnetic}) = \frac{2\pi\mu_0 e^2 \hbar^2}{m_e^2 r_1^3}$$

For $3 \leq Z$

Ionization Energy = −Electric Energy − $\frac{1}{Z}$Magnetic Energy.

18. The system of claim 1, wherein the electrons of excited states of one and multielectron atoms all exist as orbitspheres of discrete radii which are given by $r_n$ of the radial Dirac delta function, $\delta(r-r_n)$.

19. The system of claim 18, wherein the electrons of excited states of one and multielectron atoms all exist as orbitspheres of discrete radii which are given by $r_n$ of the radial Dirac delta function, $\delta(r-r_n)$ that serve as resonator cavities and trap electromagnetic radiation of discrete resonant frequencies.

20. The system of claim 19, wherein photon absorption occurs as an excitation of a resonator mode.

21. The system of claim 20, wherein the free space photon also comprises a radial Dirac delta function, and the angular momentum of the photon given by $$m = \int \frac{1}{8\pi c} \text{Re}[r \times (E \times B^*)] dx^4 = \hbar$$

is conserved for the solutions for the resonant photons and excited state electron functions.

22. The system of claim 21, wherein the change in angular frequency of the electron is equal to the angular frequency of the resonant photon that excites the resonator cavity mode corresponding to the transition, and the energy is given by Planck's equation.

23. The system of claim 22, wherein for each multipole state with a single m value the relationship between the angular momentum $M_z$, energy U, and angular frequency $\omega$ is given by:

$$\frac{dM_z}{dr} = \frac{m}{\omega} \frac{dU}{dr}$$

independent of r where m is an integer such that the ratio of the square of the angular momentum, $M^2$, to the square of the energy, $U^2$, for a pure (l, m) multipole is given by $$\frac{M^2}{U^2} = \frac{m^2}{\omega^2}.$$

24. The system of claim 23, wherein the radiation from such a multipole of order (l, m) carries off $m\hbar$ units of the z component of angular momentum per photon of energy $\hbar\omega$.

25. The system of claim 24, wherein the photon and the electron can each posses only $\hbar$ of angular momentum which requires that the radiation field contain m photons.

26. The system of claim 25, wherein during excitation the spin, orbital, or total angular momentum of the orbitsphere can change by zero or $\pm\hbar$.

27. The system of claim 26, wherein the selection rules for multipole transitions between quantum states arise from conservation of the photon's multipole moment and angular momentum of $\hbar$.

28. The system of claim 27, wherein in an excited state, the time-averaged mechanical angular momentum and rotational energy associated with the traveling charge-density wave on the orbitsphere is zero, and the angular momentum of $\hbar$ of the photon that excites the electronic state is carried by the fields of the trapped photon.

29. The system of claim 28, wherein the amplitudes of the rotational moment of inertia, angular momentum, and energy that couple to external magnetic and electromagnetic fields are given $$\text{by } I_{orbital} = m_e r_n^2 \left[\frac{\ell(\ell+1)}{\ell^2 + 2\ell + 1}\right]^{\frac{1}{2}} = m_e r_n^2 \sqrt{\frac{\ell}{\ell+1}},$$

$$L = I\omega i_z = I_{orbital}\omega i_z = m_e r_n^2 \left[\frac{\ell(\ell+1)}{\ell^2 + 2\ell + 1}\right]^{\frac{1}{2}}\omega i_z = m_e r_n^2 \frac{\hbar}{m_e r_n^2}\sqrt{\frac{\ell}{\ell+1}} = \hbar\sqrt{\frac{\ell}{\ell+1}}, \text{ and}$$

$$E_{rotational\ orbital} = \frac{\hbar^2}{2I}\left[\frac{\ell(\ell+1)}{\ell^2 + 2\ell + 1}\right] = \frac{\hbar^2}{2I}\left[\frac{\ell}{\ell+1}\right] = \frac{\hbar^2}{2m_e r_n^2}\left[\frac{\ell}{\ell+1}\right],$$

respectively.

30. The system of claim 29, wherein the electron charge-density waves are nonradiative due to the angular motion, but excited states are radiative due to a radial dipole that arises from the presence of the trapped photon.

31. The system of claim 30, wherein the total number of multipoles, $N_{l,s}$, of an energy level corresponding to a principal quantum number n where each multipole corresponds to an l and $m_l$ quantum number is $$N_{\ell,s} = \sum_{\ell=0}^{n-1} \sum_{m_\ell=-\ell}^{+\ell} 1 = \sum_{\ell=0}^{n-1} 2\ell + 1 = (\ell+1)^2 = \ell^2 + 2\ell + 1 = n^2.$$

32. The system of claim 31, wherein the photon's electric field superposes that of the nucleus for $r_1 < r < r_2$ such that the radial electric field has a magnitude proportional to e/n at the electron 2 (the excited electron) where n=2,3, 4, . . . for excited states such that U is decreased by the factor of $1/n^2$.

33. The system of claim 32, wherein the "trapped photon" of the excited state is a "standing electromagnetic wave" which actually is a traveling wave that propagates on the surface around the z-axis, and its source current is only at the orbitsphere.

34. The system of claim 33, wherein the time-function factor, k(t), for the "standing wave" is identical to the time-function factor of the orbitsphere in order to satisfy the boundary (phase) condition at the orbitsphere surface such that the angular frequency of the "trapped photon" is identical to the angular frequency of the electron orbitsphere, $\omega_n$.

35. The system of claim 34, wherein the angular functions of the "trapped photon" are identical to the spherical harmonic angular functions of the electron orbitsphere.

36. The system of claim 35, wherein combining k(t) with the φ-function factor of the spherical harmonic gives $e^{i(m\phi-\omega_n t)}$ for both the electron and the "trapped photon" function.

37. The system of claim 36, wherein the photon "standing wave" in an excited electronic state is a solution of Laplace's equation in spherical coordinates with source currents matching those of the electron orbitsphere "glued" to the electron and phase-locked to the electron current density wave that travel on the surface with a radial electric field.

38. The system of claim 37, wherein the photon field is purely radial since the field is traveling azimuthally at the speed of light even though the spherical harmonic function has a velocity less than light speed.

39. The system of claim 38, wherein the photon field does not change the nature of the electrostatic field of the nucleus or its energy except at the position of the electron.

40. The system of claim 39, wherein the photon "standing wave" function comprises a radial Dirac delta function that "samples" the Laplace equation solution only at the position infinitesimally inside of the electron current-density function and superimposes with the proton field to give a field of radial magnitude corresponding to a charge of e/n where n=2,3, 4, . . . .

41. The system of claim 40, wherein the electric field of the nucleus for $r_1 < r_2$ is $$E_{nucleus} = \frac{e}{4\pi\varepsilon_o r^2}.$$

42. The system of claim 41, wherein the equation of the electric field of the "trapped photon" for $r=r_2$ where $r_2$ is the radius of electron 2, is $$E_{r\,photon\,n,l,m|r=r_2} =$$
$$\frac{e}{4\pi\varepsilon_o r_2^2}\left[-1 + \frac{1}{n}[Y_0^0(\theta,\phi) + \text{Re}\{Y_\ell^m(\theta,\phi)e^{i\omega_n t}\}]\right]\delta(r - r_n)$$

$$\omega_n = 0 \text{ for } m = 0$$

$$\omega_n = 0.$$

43. The system of claim 42, wherein the total central field for $r=r_2$ is given by the sum of the electric field of the nucleus and the electric field of the "trapped photon":

$$E_{total} = E_{nucleus} + E_{photon}.$$

44. The system of claim 43, wherein for $r_1 < r < r_2$, $$E_{r_{total}} = \frac{e}{4\pi\varepsilon_o r_1^2} + \frac{e}{4\pi\varepsilon_o r_2^2}$$
$$\left[-1 + \frac{1}{n}[Y_0^0(\theta,\phi) + \text{Re}\{Y_\ell^m(\theta,\phi)e^{i\omega_n t}\}]\right]\delta(r - r_n)$$
$$= \frac{1}{n}\frac{e}{4\pi\varepsilon_o r_2^2}[Y_0^0(\theta,\phi) + \text{Re}\{Y_\ell^m(\theta,\phi)e^{i\omega_n t}\}]\delta(r - r_n)$$

$$\omega_n = 0 \text{ for } m = 0.$$

45. The system of claim 44, wherein for $r=r_2$ and $m=0$, the total radial electric field is $$E_{r_{total}} = \frac{1}{n}\frac{e}{4\pi\varepsilon_o r^2}.$$

46. The system of claim 45, wherein the result is the same for the excited states of the one-electron atom in that the total radial electric field is $$E_{r_{total}} = \frac{1}{n}\frac{e}{4\pi\varepsilon_o r^2}.$$

47. The system of claim 45, wherein for $r_1 < r < r_2$, $$E_{r_{total}} = \frac{e}{4\pi\varepsilon_o r_1^2} + \frac{e}{4\pi\varepsilon_o r_2^2}$$
$$\left[-1 + \frac{1}{n}[Y_0^0(\theta,\phi) + \text{Re}\{Y_\ell^m(\theta,\phi)e^{i\omega_n t}\}]\right]\delta(r - r_n)$$
$$= \frac{1}{n}\frac{e}{4\pi\varepsilon_o r_2^2}[Y_0^0(\theta,\phi) + \text{Re}\{Y_\ell^m(\theta,\phi)e^{i\omega_n t}\}]\delta(r - r_n)$$

$$\omega_n = 0 \text{ for } m = 0.$$

48. The system of claim 47, wherein the radii of the excited-state electron is determined from the force balance of the electric, magnetic, and centrifugal forces that corresponds to the minimum of energy of the system.

49. The system of claim 48, wherein the excited-state energies are given by the electric energies at these radii.

50. The system of claim 49, wherein electron orbitspheres may be spin paired or unpaired depending on the force balance which applies to each electron wherein the electron configuration is a minimum of energy.

51. The system of claim 50, wherein the minimum energy configurations are given by solutions to Laplace's equation.

52. The system of claim 51, wherein the corresponding force balance of the central Coulombic, paramagnetic, and diamagnetic forces is derived for each n-electron atom that is solved for the radius of each electron.

53. The system of claim 52, wherein the central Coulombic force is that of a point charge at the origin since the electron charge-density functions are spherically symmetrical with a harmonic time dependence.

54. The system of claim 53, wherein the ionization energy of each electron is obtained using the calculated radii in the determination of the Coulombic and any magnetic energies.

55. The system of claim 53, wherein for the singlet-excited state with l=0, the electron source current in the excited state is a constant function that spins as a globe about the z-axis:

$$\rho(r,\theta,\phi,t) = \frac{e}{8\pi r^2}[\delta(r - r_n)][Y_0^0(\theta,\phi) + Y_\ell^m(\theta,\phi)].$$

56. The system of claim 54, wherein the balance between the centrifugal and electric and magnetic forces is given by:

$$\frac{m_e v^2}{r_2} = \frac{\hbar^2}{m_e r_2^3} = \frac{1}{n}\frac{e^2}{4\pi\varepsilon_o r_2^2} + \frac{2}{3}\frac{1}{n}\frac{\hbar^2}{2m_e r_2^3}\sqrt{s(s+1)}\,; s = \frac{1}{2}.$$

57. The system of claim 56, wherein $$r_2 = \left[n - \frac{\sqrt{\frac{3}{4}}}{3}\right]a_{He}$$

$n = 2, 3, 4, \ldots$ .

58. The system of claim 57, wherein the excited-state energy is the energy stored in the electric field, $E_{ele}$, which is the energy of the excited-state electron (electron 2) relative to the ionized electron at rest having zero energy:

$$E_{ele} = -\frac{1}{n}\frac{e^2}{8\pi\varepsilon_o r_2}.$$

59. The system of claim 56, wherein the forces on electron 2 due to the nucleus and electron 1 are radial/central, invariant of $r_1$, and independent of $r_1$ with the condition that $r_1 < r_2$, such that $r_2$ can be determined without knowledge of $r_1$.

60. The system of claim 56, wherein $r_1$ is solved using the equal and opposite magnetic force of electron 2 on electron 1 at the radius $r_2$ determined from the force balance equation for electron 2 and the central Coulombic force corresponding to the charge of the nucleus.

61. The system of claim 59, wherein the force balance between the centrifugal and electric and magnetic forces is $$\frac{m_e v^2}{r_1} = \frac{\hbar^2}{m_e r_1^3} = \frac{1}{n}\frac{2e^2}{4\pi\varepsilon_o r_1^2} - \frac{1}{3}\frac{1}{n}\frac{\hbar^2}{2m_e r_2^3}\sqrt{s(s+1)}\,;\, s=\frac{1}{2}$$

such that with $$s=\frac{1}{2},$$

$$r_1^3 - \left(\frac{12n}{\sqrt{3}}r_2^3\right)r_1 + \frac{6n}{\sqrt{3}}r_2^3 = 0$$

$$n = 2, 3, 4, \ldots$$

$$r_1 = r_{13} = -\sqrt{\frac{2}{3}g}\left(\cos\frac{\theta}{3} - \sqrt{3}\sin\frac{\theta}{3}\right)$$

where $r_1$ and $r_2$ are in units of $a_{He}$.

62. The system of claim 54, wherein for the triplet-excited state with $l \neq 0$, time-independent charge-density waves corresponding to the source currents travel on the surface of the orbitsphere of electron 2 about the z-axis.

63. The system of claim 54, wherein in the triplet state, the spin-spin force is paramagnetic and twice that of the singlet state.

64. The system of claim 63, wherein the force balance between the centrifugal and electric and magnetic forces is:

$$\frac{m_e v^2}{r_2} = \frac{\hbar^2}{m_e r_2^3} = \frac{1}{n}\frac{e^2}{4\pi\varepsilon_o r_2^2} + \frac{4}{3}\frac{1}{n}\frac{\hbar^2}{2m_e r_2^3}\sqrt{s(s+1)}\,.$$

65. The system of claim 64, wherein $$r_2 = \left[n - \frac{\sqrt[2]{\frac{3}{4}}}{3}\right]a_{He}$$

$$n = 2, 3, 4, \ldots\,.$$

66. The system of claim 65, wherein the excited-state energy is the energy stored in the electric field, $E_{ele}$, which is the energy of the excited-state electron (electron 2) relative to the ionized electron at rest having zero energy:

$$E_{ele} = -\frac{1}{n}\frac{e^2}{8\pi\varepsilon_o r_2}.$$

67. The system of claim 64, wherein using $r_2$, $r_1$ is be solved using the equal and opposite magnetic force of electron 2 on electron 1 and the central Coulombic force corresponding to the nuclear charge such that the force balance between the centrifugal and electric and magnetic forces is $$\frac{m_e v^2}{r_1} = \frac{\hbar^2}{m_e r_1^3} = \frac{1}{n}\frac{2e^2}{4\pi\varepsilon_o r_1^2} - \frac{2}{3}\frac{1}{n}\frac{\hbar^2}{m_e r_2^3}\sqrt{s(s+1)}$$

and with $$s = \frac{1}{2},$$

$$r_1^3 - \left(\frac{6n}{\sqrt{3}}r_2^3\right)r_1 + \frac{3n}{\sqrt{3}}r_2^3 = 0$$

$$n = 2, 3, 4, \ldots$$

$$r_1 = r_{13} = -\sqrt{\frac{2}{3}g}\left(\cos\frac{\theta}{3} - \sqrt{3}\sin\frac{\theta}{3}\right)$$

where $r_1$ and $r_2$ are in units of $a_{He}$.

68. The system of claim 54, wherein for the singlet-excited state with $l \neq 0$, the electron source current in the excited state is the sum of constant and time-dependent functions where the latter, given by $$\rho(r, \theta, \phi, t) = \frac{e}{4\pi r^2}[\delta(r - r_n)][Y_0^0(\theta, \phi) + \text{Re}\{Y_\ell^m(\theta, \phi)e^{i\omega_n t}\}]$$

that travels about the z-axis.

69. The system of claim 68, wherein the current due to the time dependent term corresponding to p, d, f, etc. orbitals is $$J = \frac{\omega_n}{2\pi}\frac{e}{4\pi r_n^2}N[\delta(r - r_n)]\text{Re}\{Y_\ell^m(\theta, \phi)\}[u(t) \times r]$$

$$= \frac{\omega_n}{2\pi}\frac{e}{4\pi r_n^2}N'[\delta(r - r_n)](P_\ell^m(\cos\theta)\cos(m\phi + \omega_n' t))[u \times r]$$

$$= \frac{\omega_n}{2\pi}\frac{e}{4\pi r_n^2}N'[\delta(r - r_n)](P_\ell^m(\cos\theta)\cos(m\phi + \omega_n' t))\sin\theta\hat{\phi}$$

where to keep the form of the spherical harmonic as a traveling wave about the z-axis, $\omega_n' = m\omega_n$ and N and N' are normalization constants; the vectors are defined as $$\hat{\phi} = \frac{\hat{u} \times \hat{r}}{|\hat{u} \times \hat{r}|} = \frac{\hat{u} \times \hat{r}}{\sin\theta};$$

$$\hat{u} = \hat{z} = \text{orbital axis}$$

$$\hat{\theta} = \hat{\phi} \times \hat{r}$$

"^" denotes the unit vectors $$\hat{u} \equiv \frac{u}{|u|},$$

non-unit vectors are designed in bold, and the current function is normalized.

70. The system of claim 69, wherein the general multipole field solution to Maxwell's equations in a source-free region of empty space with the assumption of a time dependence $e^{i\omega_n t}$ (cgs units) is $$B = \sum_{\ell,m} \left[ a_E(\ell, m) f_\ell(kr) X_{\ell,m} - \frac{i}{k} a_M(\ell, m) \nabla \times g_\ell(kr) X_{\ell,m} \right]$$

$$E = \sum_{\ell,m} \left[ \frac{i}{k} a_E(\ell, m) \nabla \times f_\ell(kr) X_{\ell,m} + a_M(\ell, m) g_\ell(kr) X_{\ell,m} \right];$$

the radial functions $f_\ell(kr)$ and $g_\ell(kr)$ are of the form:

$g_\ell(kr) = A_\ell^{(1)} h_\ell^{(1)} + A_\ell^{(2)} h_\ell^{(2)}$, and $X_{\ell,m}$ is the vector spherical harmonic defined by $$X_{\ell,m}(\theta, \phi) = \frac{1}{\sqrt{\ell(\ell+1)}} L Y_{\ell,m}(\theta, \phi) \text{ where}$$

$$L = \frac{1}{i}(r \times \nabla).$$

71. The system of claim 70, wherein the coefficients $a_E(l, m)$ and $a_M(l,m)$ specify the amounts of electric (l,m) multipole and magnetic (l,m) multipole fields, and are determined by sources and boundary conditions as are the relative proportions in $g_\ell(kr)$.

72. The system of claim 71, wherein the electric and magnetic coefficients from the sources is $$a_E(\ell, m) = \frac{4\pi k^2}{i\sqrt{\ell(\ell+1)}}$$

$$\int Y_\ell^{m*} \left\{ \rho \frac{\delta}{\delta r}[rj_\ell(kr)] + \frac{ik}{c}(r \cdot J) j_\ell(kr) - ik \nabla \cdot (r \times M) j_\ell(kr) \right\} d^3 x$$

and $$a_M(\ell, m) = \frac{-4\pi k^2}{\sqrt{\ell(\ell+1)}} \int j_\ell(kr) Y_\ell^{m*} L \cdot \left( \frac{J}{c} + \nabla \times M \right) d^3 x$$

respectively, where the distribution of charge $\rho(x,t)$, current $J(x,t)$, and intrinsic magnetization $M(x,t)$ are harmonically varying sources: $\rho(x)e^{-i\omega_n t}$, $J(x)e^{-i\omega_n t}$, and $M(x)e^{-i\omega_n t}$.

73. The system of claim 72, wherein the charge and intrinsic magnetization terms are zero.

74. The system of claim 73, wherein since the source dimensions are very small compared to a wavelength ($kr_{max} \ll 1$), the small argument limit can be used to give the magnetic multipole coefficient $\alpha_M(l,m)$ as $$a_m(\ell, m) = \frac{-4\pi k^{\ell+2}}{(2\ell+1)!!} \left( \frac{\ell+1}{\ell} \right)^{1/2} (M_{\ell m} + M'_{\ell m})$$

where the magnetic multipole moments are $$M_{\ell m} = -\frac{1}{\ell+1} \int r^\ell Y_{\ell m}^* \nabla \cdot \left( \frac{r \times J}{c} \right) d^3 x$$

$$M'_{\ell m} = -\int r^\ell Y_{\ell m}^* \nabla \cdot M d^3 x.$$

75. The system of claim 74, wherein the geometrical factor of the surface current-density function of the orbitsphere about the z-axis is $$\left( \frac{2}{3} \right)^{-1}.$$

76. The system of claim 75, wherein the multipole coefficient $\alpha_{Mag}(l,m)$ of the magnetic force is $$\alpha_{Mag}(\ell, m) = \frac{\frac{3}{2}}{(2\ell+1)!!} \frac{1}{\ell+2} \left( \frac{\ell+1}{\ell} \right)^{1/2}.$$

77. The system of claim 76, wherein for singlet states with $l \neq 0$, a minimum energy is achieved with conservation of the photon's angular momentum of $\hbar$ when the magnetic moments of the corresponding angular momenta relative to the electron velocity and corresponding Lorentzian forces superimpose negatively such that the spin component is radial ($i_r$-direction) and the orbital component is central ($-i_r$-direction).

78. The system of claim 77, wherein the amplitude of the orbital angular momentum $L_{rotational\ orbital}$, is $$L = I\omega i_z = \hbar \left[ \frac{\ell(\ell+1)}{\ell^2 + 2\ell+1} \right]^{\frac{1}{2}} = \hbar \sqrt{\frac{\ell}{\ell+1}}.$$

79. The system of claim 78, wherein the magnetic force between the two electrons is $$F_{mag} = \frac{1}{n} \frac{\frac{3}{2}}{(2\ell+1)!!} \frac{1}{\ell+2} \left( \frac{\ell+1}{\ell} \right)^{1/2} \frac{1}{2} \frac{\hbar^2}{m_e r^3} \left( \sqrt{s(s+1)} - \sqrt{\frac{\ell}{\ell+1}} \right) i_r.$$

80. The system of claim 79, wherein the force balance equation which achieves the condition that the sum of the mechanical momentum and electromagnetic momentum is $$\frac{m_e v^2}{r_2} = \frac{\hbar^2}{m_e r_2^3} = \frac{1}{n} \frac{e^2}{4\pi\varepsilon_o r_2^2} -$$

$$\frac{1}{n} \frac{\frac{3}{2}}{(2\ell+1)!!} \left(\frac{\ell+1}{\ell}\right)^{1/2} \frac{1}{\ell+2} \frac{1}{2} \frac{\hbar^2}{m_e r^3} \left( \sqrt{s(s+1)} - \sqrt{\frac{\ell}{\ell+1}} \right);$$

$$s = \frac{1}{2}.$$

81. The system of claim 80, wherein $$r_2 = \left[ n + \frac{\frac{3}{4}}{(2\ell+1)!!} \frac{1}{\ell+2} \left(\frac{\ell+1}{\ell}\right)^{1/2} \left( \sqrt{\frac{3}{4}} - \sqrt{\frac{\ell}{\ell+1}} \right) \right] a_{He}$$

$$n = 2, 3, 4, \ldots.$$

82. The system of claim 81, wherein the excited-state energy is the energy stored in the electric field, $E_{ele}$, which is the energy of the excited-state electron (electron 2) relative to the ionized electron at rest having zero energy:

$$E_{ele} = -\frac{1}{n} \frac{e^2}{8\pi\varepsilon_o r_2}.$$

83. The system of claim 80, wherein using $r_2$, $r_1$ can be solved using the equal and opposite magnetic force of electron 2 on electron 1 and the central Coulombic force corresponding to the nuclear charge.

84. The system of claim 83, wherein the force balance between the centrifugal and electric and magnetic forces is $$\frac{m_e v^2}{r_1} = \frac{\hbar^2}{m_e r_1^3} =$$

$$\frac{2e^2}{4\pi\varepsilon_o r_1^2} + \frac{1}{n} \frac{\frac{3}{2}}{(2\ell+1)!!} \left(\frac{\ell+1}{\ell}\right)^{1/2} \frac{1}{\ell+2} \frac{1}{2} \frac{\hbar^2}{m_e r_2^3} \left( \sqrt{s(s+1)} - \sqrt{\frac{\ell}{\ell+1}} \right)$$

such that with $$s = \frac{1}{2},$$

$$r_1^3 + \frac{n 8 r_1 r_2^3}{3\left( \sqrt{\frac{3}{4}} - \sqrt{\frac{\ell}{\ell+1}} \right)} (2\ell+1)!! \left(\frac{\ell}{\ell+1}\right)^{1/2} (\ell+2) -$$

$$\frac{n 4 r_2^3}{3\left( \sqrt{\frac{3}{4}} - \sqrt{\frac{\ell}{\ell+1}} \right)} (2\ell+1)!! \left(\frac{\ell}{\ell+1}\right)^{1/2} (\ell+2) = 0$$

-continued $$n = 2, 3, 4, \ldots$$

$$r_1 = r_{11} = \sqrt[3]{\frac{g}{2}} \left\{ \sqrt[3]{1 + \sqrt{1 - \frac{32}{27}g}} - \sqrt[3]{\sqrt{1 - \frac{32}{27}g} - 1} \right\}$$

where $r_1$ and $r_2$ are in units of $a_{He}$.

85. The system of claim 80, wherein for the triplet-excited state with $l \neq 0$, a minimum energy is achieved with conservation of the photon's angular momentum of $\hbar$ when the magnetic moments of the corresponding angular momenta superimpose negatively such that the spin component is central and the orbital component is radial.

86. The system of claim 85, wherein the spin is doubled such that the force balance equation is given by $$\frac{m_e v^2}{r_2} = \frac{\hbar^2}{m_e r_2^3} = \frac{1}{n} \frac{e^2}{4\pi\varepsilon_o r_2^2} +$$

$$\frac{1}{n} \frac{\frac{3}{2}}{(2\ell+1)!!} \left(\frac{\ell+1}{\ell}\right)^{1/2} \frac{1}{\ell+2} \frac{1}{2} \frac{\hbar^2}{m_e r^3} \left( 2\sqrt{s(s+1)} - \sqrt{\frac{\ell}{\ell+1}} \right);$$

$$s = \frac{1}{2}.$$

87. The system of claim 86, wherein $$r_2 = \left[ n - \frac{\frac{3}{4}}{(2\ell+1)!!} \frac{1}{\ell+2} \left(\frac{\ell+1}{\ell}\right)^{1/2} \left( 2\sqrt{\frac{3}{4}} - \sqrt{\frac{\ell}{\ell+1}} \right) \right] a_{He}$$

$$n = 2, 3, 4, \ldots.$$

88. The system of claim 87, wherein the excited-state energy is the energy stored in the electric field, $E_{ele}$, which is the energy of the excited-state electron (electron 2) relative to the ionized electron at rest having zero energy:

$$E_{ele} = -\frac{1}{n} \frac{e^2}{8\pi\varepsilon_0 r_2}.$$

89. The system of claim 86, wherein using $r_2$, $r_1$ can be solved using the equal and opposite magnetic force of electron 2 on electron 1 and the central Coulombic force corresponding to the nuclear charge.

90. The system of claim 89, wherein the force balance between the centrifugal and electric and magnetic forces is $$\frac{m_e v^2}{r_1} = \frac{\hbar^2}{m_e r_1^3} =$$

$$\frac{2e^2}{4\pi\varepsilon_o r_1^2} - \frac{1}{n} \frac{\frac{3}{2}}{(2\ell+1)!!} \left(\frac{\ell+1}{\ell}\right)^{1/2} \frac{1}{\ell+2} \frac{1}{2} \frac{\hbar}{m_e r_2^3} \left( 2\sqrt{s(s+1)} - \sqrt{\frac{\ell}{\ell+1}} \right)$$

such that with $$s = \frac{1}{2},$$

$$r_1^3 - \frac{n 8 r_1 r_2^3}{3\left(\sqrt{\frac{3}{4}} - \sqrt{\frac{\ell}{\ell+1}}\right)}(2\ell+1)!!\left(\frac{\ell}{\ell+1}\right)^{1/2}(\ell+2) +$$

$$\frac{n 4 r_2^3}{3\left(\sqrt{\frac{3}{4}} - \sqrt{\frac{\ell}{\ell+1}}\right)}(2\ell+1)!!\left(\frac{\ell}{\ell+1}\right)^{1/2}(\ell+2) = 0$$

$$n = 2, 3, 4, \ldots$$

$$r_1 = r_{13} = -\sqrt{\frac{2}{3}g}\left(\cos\frac{\theta}{3} - \sqrt{3}\sin\frac{\theta}{3}\right)$$

where $r_1$ and $r_2$ are in units of $a_{He}$.

91. The system of claim 87, wherein the spin-orbital coupling force is used in the force balance equation wherein the corresponding energy $E_{s/o}$ is given by $$E_{s/o} = 2\frac{\alpha}{2\pi}\left(\frac{e\hbar}{2m_e}\right)\frac{\mu_0 e\hbar}{2(2\pi m_e)\left(\frac{r}{2\pi}\right)^3}\sqrt{\frac{3}{4}} = \frac{\alpha\pi\mu_0 e^2 \hbar^2}{m_e^2 r^3}\sqrt{\frac{3}{4}}.$$

92. The system of claim 91, wherein the force balance also includes a term corresponding to the frequency shift derived after that of the Lamb shift.

93. The system of claim 92, wherein with $\Delta m_\ell = -1$ is included and the energy, $E_{FS}$, for the $^2P_{3/2} \to {}^2P_{1/2}$ transition called the fine structure splitting is given by:

$$E_{FS} = \frac{\alpha^5(2\pi)^2}{8}m_e c^2 \sqrt{\frac{3}{4}} + \left(13.5983 \text{ eV}\left(1 - \frac{1}{2^2}\right)\right)^2$$

$$\left[\frac{\left(\frac{3}{4\pi}\left(1 - \sqrt{\frac{3}{4}}\right)\right)^2}{2\mu_e c^2} + \frac{\left(1 + \left(1 - \sqrt{\frac{3}{4}}\right)\right)^2}{2m_H c^2}\right]$$

$$= 4.5190 \times 10^{-5} \text{ eV} + 1.75407 \times 10^{-7} \text{ eV}$$

$$= 4.53659 \times 10^{-5} \text{ eV}$$

where the first term corresponds to $E_{s/o}$ expressed in terms of the mass energy of the electron and the second and third terms correspond to the electron recoil and atom recoil, respectively.

94. A method comprising:
  inputting the electron functions that obey Maxwell's equations;
  determining the corresponding centrifugal, Coulombic, diamagnetic and paramagnetic forces for a given set of quantum numbers corresponding to a solution of Maxwell's equations for at least one photon and one electron of the excited state;
  forming the force balance equation comprising the centrifugal force equal to the sum of the Coulombic, diamagnetic and paramagnetic forces;
  solving the force balance equation for the electron radii;
  calculating the energy of the electrons using the radii and the corresponding electric and magnetic energies, and
  outputting the calculated energy of the electrons,
  wherein the electron functions are given by at least one of the group comprsing:

$\ell = 0$ $$\rho(r, \theta, \phi, t) = \frac{e}{8\pi r^2}[\delta(r - r_n)][Y_0^0(\theta, \phi) + Y_\ell^m(\theta, \phi)]$$

$\ell \neq 0$ $$\rho(r, \theta, \phi, t) = \frac{e}{4\pi r^2}[\delta(r - r_n)][Y_0^0(\theta, \phi) + \text{Re}\{Y_\ell^m(\theta, \phi)e^{i\omega_n t}\}]$$

where $Y_\ell^m(\theta,\phi)$ are the spherical harmonic functions that spin about the z-axis with angular frequency $\omega_n$ with $Y_0^0(\theta,\phi)$ the constant function; $\text{Re}\{Y_\ell^m(\theta,\phi)e^{i\omega t}\} = P_\ell^m(\cos\theta)\cos(m\phi + \omega_n t)$ where to keep the form of the spherical harmonic as a traveling wave about the z-axis, $\omega_n' = m\omega_n$.

95. The method according to claim 94, wherein the force balance equation is given by at least one of the group comprising:

$$\frac{m_e v^2}{r_2} = \frac{\hbar^2}{m_e r_2^3} = \frac{1}{n}\frac{e^2}{4\pi\varepsilon_0 r_2^2} + \frac{2}{3}\frac{1}{n}\frac{\hbar^2}{2m_e r_2^3}\sqrt{s(s+1)}$$

$$\frac{m_e v^2}{r_1} = \frac{\hbar^2}{m_e r_1^3} = \frac{1}{n}\frac{2e^2}{4\pi\varepsilon_0 r_1^2} - \frac{1}{3}\frac{1}{n}\frac{\hbar^2}{2m_e r_2^3}\sqrt{s(s+1)}$$

$$\frac{m_e v^2}{r_2} = \frac{\hbar^2}{m_e r_2^3} = \frac{1}{n}\frac{e^2}{4\pi\varepsilon_0 r_2^2} + \frac{4}{3}\frac{1}{n}\frac{\hbar^2}{2m_e r_2^3}\sqrt{s(s+1)}$$

$$\frac{m_e v^2}{r_1} = \frac{\hbar^2}{m_e r_1^3} = \frac{1}{n}\frac{2e^2}{4\pi\varepsilon_0 r_1^2} - \frac{2}{3}\frac{1}{n}\frac{\hbar^2}{m_e r_2^3}\sqrt{s(s+1)}$$

$$\frac{m_e v^2}{r_2} = \frac{\hbar^2}{m_e r_2^3} = \frac{1}{n}\frac{e^2}{4\pi\varepsilon_0 r_2^2} - \frac{1}{n}\frac{\frac{3}{2}}{(2\ell+1)!!}\left(\frac{\ell+1}{\ell}\right)^{1/2}$$

$$\frac{1}{\ell+2}\frac{1}{2}\frac{\hbar^2}{m_e r^3}\left(\sqrt{s(s+1)} - \sqrt{\frac{\ell}{\ell+1}}\right)$$

$$\frac{m_e v^2}{r_1} = \frac{\hbar^2}{m_e r_1^3} = \frac{2e^2}{4\pi\varepsilon_0 r_1^2} + \frac{1}{n}\frac{\frac{3}{2}}{(2\ell+1)!!}\left(\frac{\ell+1}{\ell}\right)^{1/2}$$

$$\frac{1}{\ell+2}\frac{1}{2}\frac{\hbar^2}{m_e r_2^3}\left(\sqrt{s(s+1)} - \sqrt{\frac{\ell}{\ell+1}}\right)$$

$$\frac{m_e v^2}{r_2} = \frac{\hbar^2}{m_e r_2^3} = \frac{1}{n}\frac{e^2}{4\pi\varepsilon_0 r_2^2} + \frac{1}{n}\frac{\frac{3}{2}}{(2\ell+1)!!}\left(\frac{\ell+1}{\ell}\right)^{1/2}$$

$$\frac{1}{\ell+2}\frac{1}{2}\frac{\hbar^2}{m_e r^3}\left(2\sqrt{s(s+1)} - \sqrt{\frac{\ell}{\ell+1}}\right)$$

$$\frac{m_e v^2}{r_1} = \frac{\hbar^2}{m_e r_1^3} = \frac{2e^2}{4\pi\varepsilon_0 r_1^2} - \frac{1}{n}\frac{\frac{3}{2}}{(2\ell+1)!!}\left(\frac{\ell+1}{\ell}\right)^{1/2}$$

$$\frac{1}{\ell+2}\frac{1}{2}\frac{\hbar^2}{m_e r_2^3}\left(2\sqrt{s(s+1)} - \sqrt{\frac{\ell}{\ell+1}}\right)$$

wherein $$s = \frac{1}{2}.$$

96. The method according to claim 95, wherein the radii are given by at least one of the group comprising:

$$r_2 = \left[n - \frac{\sqrt{\frac{3}{4}}}{3}\right]a_{He} \quad n = 2, 3, 4, \ldots$$

$$r_1 = r_{13} = -\sqrt{\frac{2}{3}g}\left(\cos\frac{\theta}{3} - \sqrt{3}\sin\frac{\theta}{3}\right)$$

$$r_2 = \left[n - \frac{2\sqrt{\frac{3}{4}}}{3}\right]a_{He} \quad n = 2, 3, 4, \ldots$$

$$r_1 = r_{13} = -\sqrt{\frac{2}{3}}g\left(\cos\frac{\theta}{3} - \sqrt{3}\sin\frac{\theta}{3}\right)$$

$$r_2 = \left[n + \frac{\frac{3}{4}}{(2\ell+1)!!}\frac{1}{\ell+2}\left(\frac{\ell+1}{\ell}\right)^{1/2}\left(\sqrt{\frac{3}{4}} - \sqrt{\frac{\ell}{\ell+1}}\right)\right]a_{He}$$
$$n = 2, 3, 4, \ldots$$

$$r_1 = r_{11} = \sqrt[3]{-\frac{g}{2}}\left\{\sqrt[3]{1 + \sqrt{1 - \frac{32}{27}g}} - \sqrt[3]{\sqrt{1 - \frac{32}{27}g} - 1}\right\}$$

$$r_2 = \left[n - \frac{\frac{3}{4}}{(2\ell+1)!!}\frac{1}{\ell+2}\left(\frac{\ell+1}{\ell}\right)^{1/2}\left(2\sqrt{\frac{3}{4}} - \sqrt{\frac{\ell}{\ell+1}}\right)\right]a_{He}$$
$$n = 2, 3, 4, \ldots$$

$$r_1 = r_{13} = -\sqrt{\frac{2}{3}g}\left(\cos\frac{\theta}{3} - \sqrt{3}\sin\frac{\theta}{3}\right)$$

where $r_1$ and $r_2$ are in units of $a_{He}$.

97. The method according to claim 96, wherein the electric energy of each electron of radius $r_n$ is given by:

$$E_{ele} = -\frac{1}{n}\frac{e^2}{8\pi\varepsilon_o r_2}.$$

* * * * *

UNITED STATES PATENT AND TRADEMARK OFFICE
CERTIFICATE OF CORRECTION

PATENT NO. : 7,689,367 B2  
APPLICATION NO. : 11/596218  
DATED : March 30, 2010  
INVENTOR(S) : Randell L. Mills Page 1 of 1

It is certified that error appears in the above-identified patent and that said Letters Patent is hereby corrected as shown below:

Claim 2, col. 57, line 4, delete space between "L1" and "M0".

Claim 2, col. 57, line 44, delete space between "L1" and "MY".

Claim 2, col. 58, line 57, "[pbi]" should read -- [phi] --.

Claim 3, col. 59, line 9, "PointSize[0.0]" should read -- PointSize [0.01] --.

Claim 3, col. 59, line 28, delete space between "L1" and "MX".

Claim 3, col. 59, line 32, "V30" should read -- √30 --.

Claim 3, col. 59, line 33, "V30" should read -- √30 --.

Claim 12, col. 61, line 20, "$i^{\omega nj}$" should read -- $i^{\omega nt}$ --.

Claim 25, col. 63, line 40, "posses" should read -- possess --.

Claim 67, col. 68, line 12, "is be solved" should read -- is solved --.

Signed and Sealed this

Twenty-fourth Day of August, 2010

David J. Kappos
*Director of the United States Patent and Trademark Office*